(12) United States Patent
Gaddam et al.

(10) Patent No.: US 6,528,507 B1
(45) Date of Patent: Mar. 4, 2003

(54) POLYMORPHIC FORMS OF AN ANTIDIABETIC AGENT: PROCESS FOR THEIR PREPARATION AND A PHARMACEUTICAL COMPOSITION CONTAINING THEM

(75) Inventors: Om Reddy Gaddam; Ra jender Kumar Potlapally; Ra ju Sirisilla; Vyas Krishnamurthi; Sreenivasa Rao Dharmaraja; Ramabhadra Sarma Mamillapalli, all of Hyderabad (IN)

(73) Assignee: Dr. Reddy's Laboratories Limited, Hyderabad (IN)

( * ) Notice: Subject to any disclaimer, the term of this patent is extended or adjusted under 35 U.S.C. 154(b) by 0 days.

(21) Appl. No.: 09/550,862

(22) Filed: Apr. 17, 2000

(51) Int. Cl.[7] ................... C07D 265/38; A61K 31/538; A61P 3/04; A61P 3/10
(52) U.S. Cl. ..................................... 514/229.8; 544/102
(58) Field of Search ...................... 544/102; 514/229.8

(56) References Cited

U.S. PATENT DOCUMENTS

| | | | |
|---|---|---|---|
| 5,248,699 A | | 9/1993 | Sysko .................. 514/647 |
| 5,700,820 A | | 12/1997 | Vyas et al. ............. 514/369 |
| 6,054,453 A | * | 4/2000 | Lohray et al. ........... 514/226.2 |

FOREIGN PATENT DOCUMENTS

| | | |
|---|---|---|
| WO | 9119702 | 12/1991 |
| WO | 9727191 | 7/1997 |
| WO | 9731907 | 9/1997 |
| WO | 9733878 | 9/1997 |
| WO | 9919313 | 4/1999 |
| WO | 9920614 | 4/1999 |
| WO | 9938850 | 8/1999 |

OTHER PUBLICATIONS

Giron, D. "Thermal Analysis and Calorimetric Methods In The Characterisation of Polymorphs."Thermochimica Acta, vol. 248, No. 248 (1995/pp1–59).

Threlfall, T.L "Analysis of Organic Polymorphs. "Analyst, vol. 120, No. 120 (1995) pp 2435–2460.

\* cited by examiner

Primary Examiner—Mark L. Berch
Assistant Examiner—Kahsay Habte
(74) Attorney, Agent, or Firm—Ladas & Parry

(57) ABSTRACT

This invention relates to novel polymorphic/ pseudopolymorphic forms of arginine salt of 3-[4-[2-(phenoxazin-10-yl)ethoxy]phenyl]-2-ethoxypropanoic acid, having the formula I shown below. The invention also relates to a pharmaceutical composition comprising the novel polymorphic form or their mixture and a pharmaceutically acceptable carrier. The polymorphic forms of the present invention are more active, as antidiabetic and hypolipidemic agent, than the novel 3-[4-[2-(phenoxazin-10-yl) ethoxy]phenyl]-2-ethoxypropanoic acid.

(I)

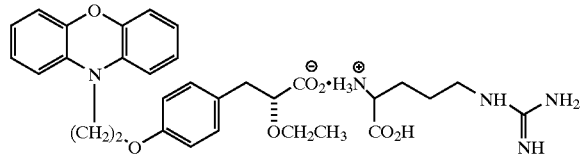

101 Claims, 36 Drawing Sheets

POLYMORPHIC FORMS OF AN ANTIDIABETIC AGENT: PROCESS FOR THEIR PREPARATION AND A PHARMACEUTICAL COMPOSITION CONTAINING THEM

BACKGROUND OF THE INVENTION

This invention relates to novel polymorphic/pseudopolymorphic forms of arginine salt of 3-[4-[2-(phenoxazin-10-yl)ethoxy]phenyl]-2-ethoxypropanoic acid, preferably, L-arginine salt of (2S) 3-[4-[2-(phenoxazin-10-yl)ethoxy]phenyl]-2-ethoxypropanoic acid, having the formula I shown below. The invention also relates to a pharmaceutical composition comprising the novel polymorphic form or their mixture and a pharmaceutically acceptable carrier. The polymorphic forms of the present invention are more active, as antidiabetic and hypolipidemic agent, than the novel 3-[4-[2-(phenoxazin-10-yl)ethoxy]phenyl]-2-ethoxypropanoic acid.

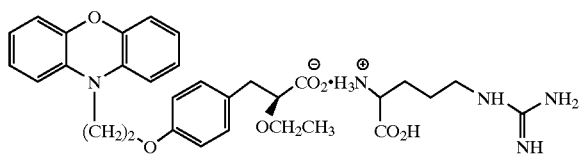

The present invention also relates to a process for the preparation of novel polymorphic/pseudopolymorphic Forms of arginine salt of 3-[4-[2-(phenoxazin-10-yl)ethoxy] phenyl]-2-ethoxypropanoic acid, having the formula (I).

The polymorphic Forms of arginine salt of 3-[4-[2-(phenoxazin-10-yl)ethoxy]phenyl]-2-ethoxypropanoic acid, of formula (I) defined above of the present invention lower total cholesterol (TC); increase high density lipoprotein (HDL) and decrease low density lipoprotein (LDL), which have a beneficial effect on coronary heart disease and atherosclerosis.

The novel polymorphic Forms of arginine salt of 3-[4-[2-(phenoxazin-10-yl)ethoxy]phenyl]-2-ethoxypropanoic acid, of formula (I) defined above of the present invention are useful in reducing body weight and for the treatment and/or prophylaxis of. diseases such as hypertension, coronary heart disease, atherosclerosis, stroke, peripheral vascular diseases and related disorders. These novel polymorphic Forms compounds are useful for the treatment of familial hypercholesterolemia, hypertriglyceridemia, lowering of atherogenic lipoproteins, VLDL (very low density lipoprotein) and LDL. The novel polymorphic Forms of arginine salt of 3-[4-[2-(phenoxazin-10-yl)ethoxy]phenyl]-2-ethoxypropanoic acid, of formula (I) of the present invention can be used for the treatment of certain renal diseases including glomerulonephritis, glomerulosclerosis, nephrotic syndrome, hypertensive nephrosclerosis and nephropathy. The novel polymorphic Forms of arginine salt of 3-[4-[2-(phenoxazin-10-yl)ethoxy]phenyl]-2-ethoxypropanoic acid, of formula (I) are also useful for the treatment and/or prophylaxis of insulin resistance (type diabetes), leptin resistance, impaired glucose tolerance, dyslipidemia, disorders related to syndrome X such as hypertension, obesity, insulin resistance, coronary heart disease and other cardiovascular disorders. These novel polymorphic Forms of arginine salt of 3-[4-[2-(phenoxazin-10-yl)ethoxy]phenyl]-2-ethoxypropanoic acid, of formula (I) may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, retinopathy, xanthoma, inflammation and for the treatment of cancer. The novel polymorphic Forms of arginine salt of 3-[4-[2-(phenoxazin-10-yl)ethoxy]phenyl]-2-ethoxypropanoic acid, of formula (I) of the present invention are useful in the treatment and/or prophylaxis of the above said diseases in combination/con-comittant with one or more HMG CoA reductase inhibitors, hypolipidemic/hypolipoproteinemic agents such as fibric acid derivatives, nicotinic acid, cholestyramine, colestipol, probucol.

BACKGROUND OF THE INVENTION

Atherosclerosis and other peripheral vascular diseases are the major causes effecting the quality of life of millions of people. Therefore, considerable attention has been directed towards understanding the etiology of hypercholesterolemia and hyperlipidemia and development of effective therapeutic strategies.

Hypercholesterolemia has been defined as plasma cholesterol level that exceeds arbitrarily defined value called "normal" level. Recently, it has been accepted that "ideal" plasma levels of cholesterol are much below the "normal" level of cholesterol in the general population and the risk of coronary artery disease (CAD) increases as cholesterol level rises above the "optimum" (or "ideal") value. There is clearly a definite cause and effect-relationship between hypercholesterolemia and CAD, particularly for individuals with multiple risk factors. Most of the cholesterol is present in the esterified forms with various lipoproteins such as Low density lipoprotein (LDL), intermediate density lipoprotein (IDL), High density lipoprotein (HDL) and partially as Very low density lipoprotein (VLDL). Studies clearly indicate that there is an inverse correlationship between CAD and atherosclerosis with serum HDL-cholesterol concentrations. (Stampfer et al., *N. Engl. J. Med.*, 325 (1991), 373–381) and the risk of CAD increases with increasing levels of LDL and VLDL.

In CAD, generally "fatty streaks" in carotid, coronary and cerebral arteries, are found which are primarily free and esterified cholesterol. Miller et al., (Br. *Med. J.*, 282 (1981), 1741–1744) have shown that increase in HDL-particles may decrease the number of sites of stenosis in coronary arteries of human, and high level of HDL-cholesterol may protect against the progression of atherosclerosis. Picardo et al., (*Arteriosclerosis* 6 (1986) 434–441) have shown by in vitro experiment that HDL is capable of removing cholesterol from cells. They suggest that HDL may deplete tissues of excess free cholesterol and transfer it to liver (Macikinnon et al., *J. Biol. Chem.* 261 (1986), 2548–2552). Therefore, agents that increase HDL cholesterol would have therapeutic significance for the treatment of hypercholesterolemia and coronary heart diseases (CHD).

Obesity is a disease highly prevalent in affluent societies and in the developing world and is a major cause of morbidity and mortality. It is a state of excess body fat accumulation. The causes of obesity are unclear. It is believed to be of genetic origin or promoted by an interaction between the genotype and environment. Irrespective of the cause, the result is fat deposition due to imbalance between the energy intake versus energy expenditure. Dieting, exercise and appetite suppression have been a part of obesity treatment. There is a need for efficient therapy to fight this disease since it may lead to coronary heart disease, diabetes, stroke, hyperlipidemia, gout, osteoarthritis, reduced fertility and many other psychological and social problems.

Diabetes and insulin resistance is yet another disease which severely effects the quality of a large population in the world. Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (J. Clin. Invest., (1985) 75: 809–817; N. Engl. J. Med. (1987) 317: 350–357; J. Clin. Endocrinol. Metab., (1988) 66: 580–583; J. Clin. Invest., (1975) 68: 957–969) and other renal complications (See Patent Application No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X Hyperlipidemia is the primary cause for cardiovascular (CVD) and other peripheral vascular diseases. High risk of CVD is related to the higher LDL (Low Density Lipoprotein) and VLDL (Very Low Density Lipoprotein) seen in hyperlipidemia. Patients having glucose intolerance/insulin resistance in addition to hyperlipidemia have higher risk of CVD. Numerous studies in the past have shown that lowering of plasma triglycerides and total cholesterol, in particular LDL and VLDL and increasing HDL cholesterol help in preventing cardiovascular diseases.

Peroxisome proliferator activated receptors (PPAR) are members of the nuclear receptor super family. The gamma (γ), isoform of PPAR (PPARγ) has been implicated in regulating differentiation of adipocytes (Endocrinology, (1994) 135: 798–800) and energy homeostasis (Cell, (1995) 83: 803–812), whereas the alpha (α) isoform of PPAR (PPARα) mediates fatty acid oxidation (Trend. Endocrin. Metab., (1993) 4: 291–296) thereby resulting in reduction of circulating free fatty acid in plasma (Current Biol. (1995) 5: 618–621). PPARα agonists have been found useful for the treatment of obesity (WO 97/36579). It has been recently disclosed that there exists synergism for the molecules which are agonists for both PPARα and PPARγ and suggested to be useful for the treatment of syndrome X (WO 97/25042). Similar synergism between the insulin sensitizer (PPARγ agonist) and HMG CoA reductase inhibitor has been observed which may be useful for the treatment of atherosclerosis and xanthoma (EP 0 753 298).

It is known that PPARγ plays an important role in adipocyte differentiation (Cell, (1996) 87, 377–389). Ligand activation of PPAR is sufficient to cause complete terminal differentiation (Cell, (1994) 79, 1147–1156) including cell cycle withdrawal. PPARγ is consistently expressed in certain cells and activation of this nuclear receptor with PPARγ agonists would stimulate the terminal differentiation of adipocyte precursors and cause morphological and molecular changes characteristics of a more differentiated, less malignant state (Molecular Cell, (1998), 465–470; Carcinogenesis, (1998), 1949–53; Proc. Natl. Acad. Sci., (1997) 94, 237–241) and inhibition of expression of prostate cancer tissue (Cancer Research (1998) 58:3344–3352). This would be useful in the treatment of certain types of cancer, which express PPARγ and could lead to a quite nontoxic chemotherapy.

Leptin resistance is a condition wherein the target cells are unable to respond to leptin signal. This may give rise to obesity due to excess food intake and reduced energy expenditure and cause impaired glucose tolerance, type 2 diabetes, cardiovascular diseases and such other interrelated complications. Kallen et al (Proc. Natl. Acad. Sci. (1996) 93, 5793–5796) have reported that insulin sensitizers which perhaps due to the PPAR agonist expression and therefore lower plasma leptin concentrations. However, it has been recently disclosed that compounds having insulin sensitizing property also possess leptin sensitization activity. They lower the circulating plasma leptin concentrations by improving the target cell response to leptin (WO/98/02159). The latest trend that has, of late, crept into the pharmaceutical industry is the studies on polymorphism in drugs and the difference in the activity of different polymorphic forms of a given drug. By the term polymorphism we mean to include different physical forms, crystal forms, crystalline/liquid crystalline/non-crystalline (amorphous) forms. This has especially become very interesting after observing that many antibiotics, antibacterials, tranquilizers etc., exhibit polymorphism and some/one of the polymorphic forms of a given drug exhibit superior bio-availability and consequently show much higher activity compared to other polymorphs. Sertraline, Frentizole, Ranitidine, Sulfathiazole, Indomethacine etc. are some of the important examples of pharmaceuticals which exhibit polymorphism. Polymorphism in drugs is a topic of current interest and is evident from the host of patents being granted. To cite a few, U.S. Pat. No. 5,700,820 discloses six polymorphic forms of Troglitazone, U.S. Pat. No. 5,248,699 discusses about five polymorphic forms of Sertraline hydrochloride while EP 014590 describes four polymorphic forms of Frentizole. EP 490648 and EP 022527 also deal with the subject of polymorphism in drugs.

SUMMARY OF THE INVENTION

With an objective to develop novel polymorphic forms for lowering cholesterol and reducing body weight with beneficial effects in the treatment and/or prophylaxis of diseases related to increased levels of lipids, atherosclerosis, coronary artery diseases, Syndrome-X, impaired glucose tolerance, insulin resistance, insulin resistance leading to type 2 diabetes and diabetes complications thereof, for the treatment of diseases wherein insulin resistance is the pathophysiological mechanism and for the treatment of hypertension, with better efficacy, potency and lower toxicity, we focussed our research to develop new polymorphic forms effective in the treatment of the above mentioned diseases. Effort in this direction has led to polymorphic forms having the formula (I).

Another objective of the present invention is to provide polymorphic forms of arginine salt of 3-[4-[2-(phenoxazin-10-yl)ethoxy]phenyl]-2-ethoxypropanoic acid, their stereoisomers, their pharmaceutically acceptable solvates and pharmaceutical compositions containing them or their mixtures which may have agonist activity against PPARα and/or PPARγ, and optionally inhibit HMG CoA reductase, in addition to having agonist activity against PPARα and/or PPARγ.

Another objective of the present invention is to provide novel polymorphic forms of arginine salt of 3-[4-[2-(phenoxazin-10-yl)ethoxy]phenyl]-2-ethoxypropanoic acid, their stereoisomers, pharmaceutically acceptable solvates and pharmaceutical compositions containing them or their mixtures having enhanced activities, without toxic effect or with reduced toxic effect.

Yet another objective of the present invention to provide a process for the preparation of novel polymorphic forms of arginine salt of 3-[4-[2-(phenoxazin-10-yl)ethoxy]phenyl]-2-ethoxypropanoic acid, acid, their stereoisomers, pharmaceutically acceptable solvates.

Still another objective of the present invention is to provide pharmaceutical compositions containing novel polymorphic forms of arginine salt of 3-[4-[2-(phenoxazin-10-yl)ethoxy]phenyl]-2-ethoxypropanoic acid, their stereoisomers, solvates or their mixtures in combination with suitable carriers, solvents, diluents and other media normally employed in preparing such compositions.

In our PCT publication No. WO 99/19313 we have described novel β-aryl α-oxy substituted alkylcarboxylic acids of the general formula (a),

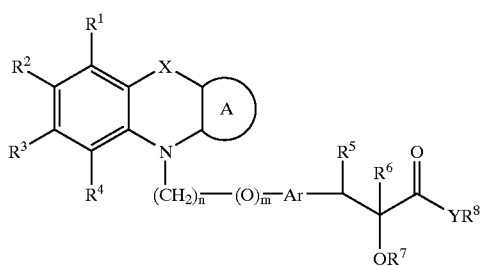

(a)

their pharmaceutically salts, their pharmaceutically solvated and their pharmaceutically acceptable compositions containing them. The pharmaceutical salts of the compounds of the general formula (a) includes salts of the organic bases such as guanine, arginine, guanidine, diethylamine, choline, and the like. Particularly the compounds disclosed include 3-[4-[2-(phenoxazin-10-yl)ethoxy]phenyl]-2-ethoxypropanoic acid. The current interest in the field of polymorphism in drugs prompted us to take up the investigation as to the possibility of polymorphism in such compounds particularly the arginine salt of 3-[4-[2-(phenoxazin-10-yl)ethoxy]phenyl]-2-ethoxypropanoic acid. Our observations and results form the subject matter of the present invention. We have, due to our sustained research directed towards finding out effective antidiabetic drugs, observed that arginine salt of 3-[4-[2-(phenoxazin-10-yl)ethoxy]phenyl]-2-ethoxypropanoic acid, exists in different polymorphic forms possessing enhanced anti-diabetic activity. Accordingly we have, in the course of research, prepared and studied at least eleven polymorphic forms of arginine salt of 3-[4-[2-(phenoxazin-10-yl)ethoxy]phenyl]-2-ethoxypropanoic acid. These polyrmorphs have been designated, by us, as Forms I, II, III, IV, V, VI, VII, VIII, IX, X and the mixture.

DETAILED DESCRIPTION OF THE INVENTION

The present invention relates to an observation that arginine salt of 3-[4-[2-(phenoxazin-10-yl)ethoxy]phenyl]-2-ethoxypropanoic acid. exhibits polymorphism, which has not been reported till date. The polymorphic Forms I, II, III, IV and V are obtained from different solvents like isopropyl alcohol, acetone, 1,4-dioxane, dimethylsulphoxide, and dimethylformamide respectively. Form VI is obtained by dissolving any form (Form IV) in water and freeze drying. Similarly Form VII is obtained by dissolving any form (Form I–V) in methanol and quick evaporation of the solvent under reduced pressure at 40–60° C. Form VIII is obtained by refluxing Form-I in 1,4-dioxane. Form-IX is obtained by refluxing Form-VIII in isopropyl alcohol. Form X is prepared by heating Form I to 185° C. and cooling it to room temperature. Form XI is prepared by heating Form X to 175° C. and cooling it to room temperature.

From powder X-ray diffraction studies Forms I, II, III, IV, V, VIII, IX and XI are found to be crystalline in nature. Forms VI, VII and X did not give any peaks in X-ray diffraction due to amorphous nature.

DSC of the polymorphic Form I shows melting endotherm at 181° C. In the mixture of polymorphic Forms I and X there is an indication to one of the endotherm at 185° C. and 181° C. Form II displays endotherms at 131° C., 166° C., 178° C., 214° C. and 276° C. and exotherms at 169° C. Form III exhibits melting endotherm 182° C. in addition to an exotherm at 168° C. Form IV exhibits endotherms at 149° C., 164° C. and 185° C. and an exotherm at 171° C. Form V exhibits endotherms at 119° C., 164° C., 172° C. and 185° C. in addition to a melting exotherm at 173° C. Form VI exhibits exotherm at 157° C. and endotherms at 179° C. and 183° C. Form VII exhibit exotherm at 132° C. and, endotherms at 176° C. and 184° C. Form VIII there was a similar exotherm of Form VI at 158° C. and the melting endotherm at 178° C., whereas in Form IX there was only one sharp melting endotherm at 176° C. Form X displays an exotherm at 163° C. and melting endotherm at 184° C. Form XI exhibits a melting endotherm at 184° C.

All these polymorphic forms were proved to be identical in solution as evident from Nuclear Magnetic Resonance (NMR), Ultra Violet (UV) & Mass spectral data. On the other hand, solid state techniques like Differential Scanning Calorimetry (DSC), Powder X-Ray Diffractometry (XRD) and Infra Red spectroscopy (IR) revealed the difference among these forms.

BRIEF DESCRIPTION OF THE FIGURES

X-ray powder diffraction pattern has been obtained on a Rigaku D/Max 2200 model diffractometer equiped with horizontal gonimometer in Θ/2Θ geometry. The copper K α (λ=1.5418A) radiation was used and the sample was scanned between 3–45 degrees

Differential scanning calorimeter was performed on a Shimadzu DSC-50 equipped with a controller. The data was collected on to a Pentium PC using a Shimadzu TA-50 software. The samples weighed in aluminum cells were heated from room temperature to 220° C. at a heating rate of 5° C./min. The empty aluminum cell was used as a reference. Dry nitrogen gas was purged through DSC cell continuously throughout the analysis at a flow of 30 ml/min.

Figure 13:
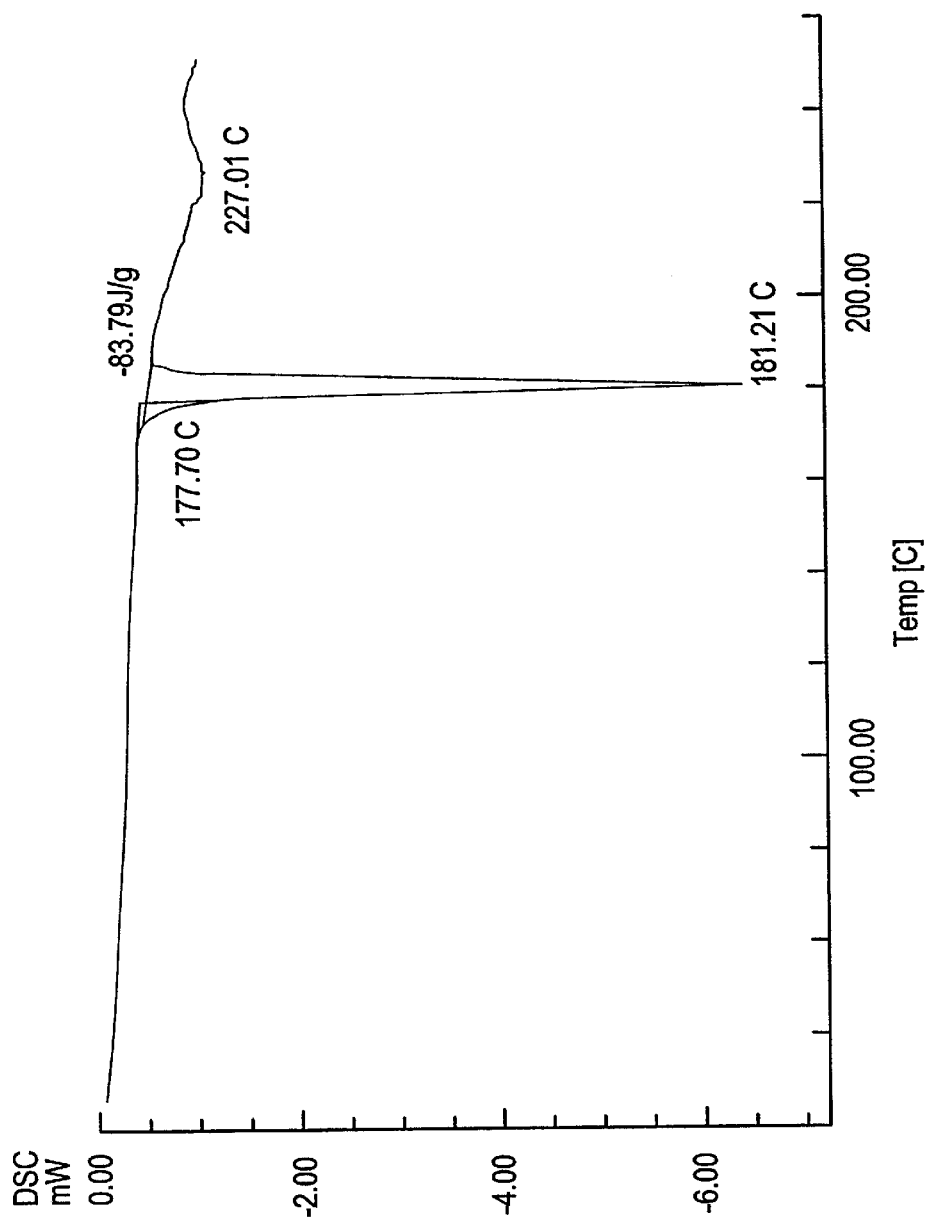

FIG. 13 is a characteristic differential scanning calorimetric thermogram of Form I.

Figure 14:
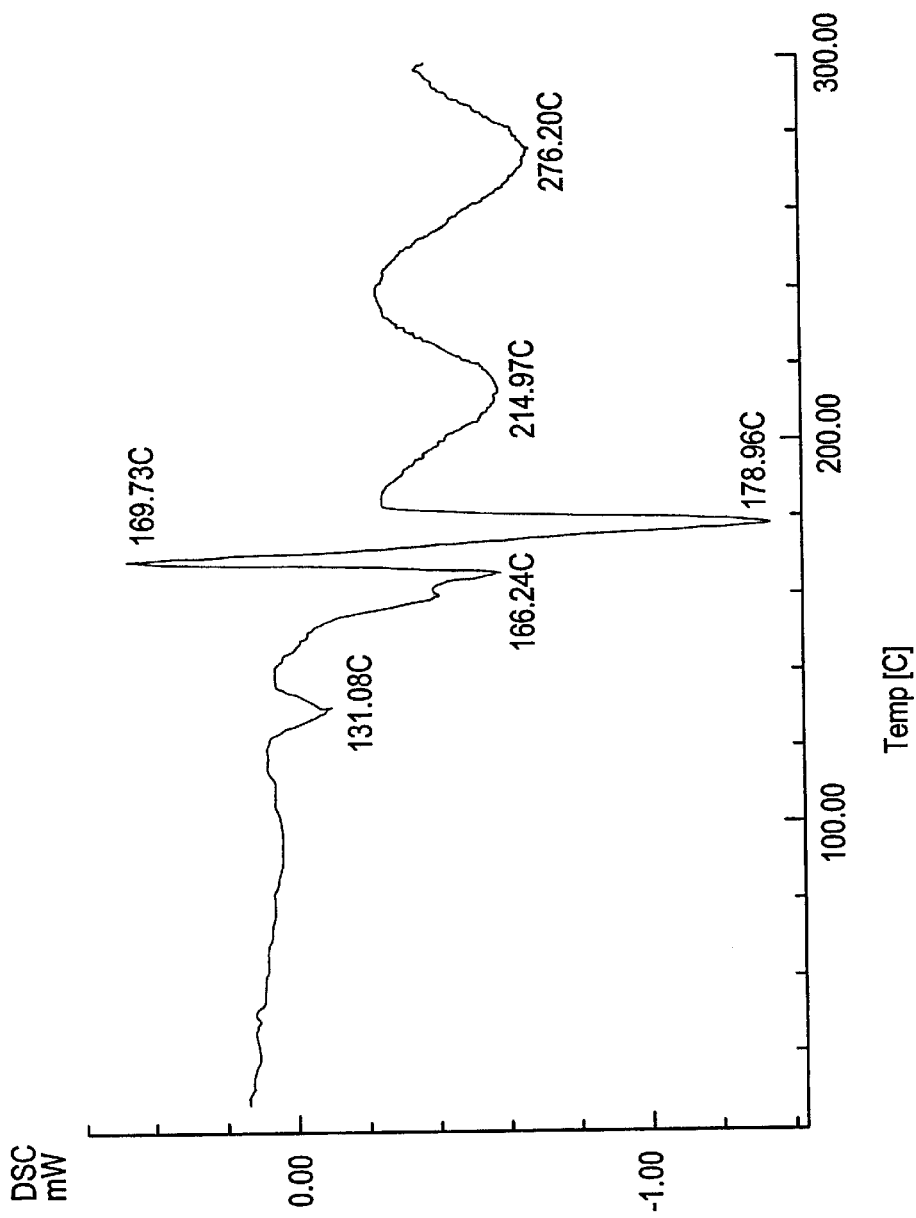

FIG. 14 is a characteristic differential scanning calorimetric thermogram of Form II.

Figure 15:
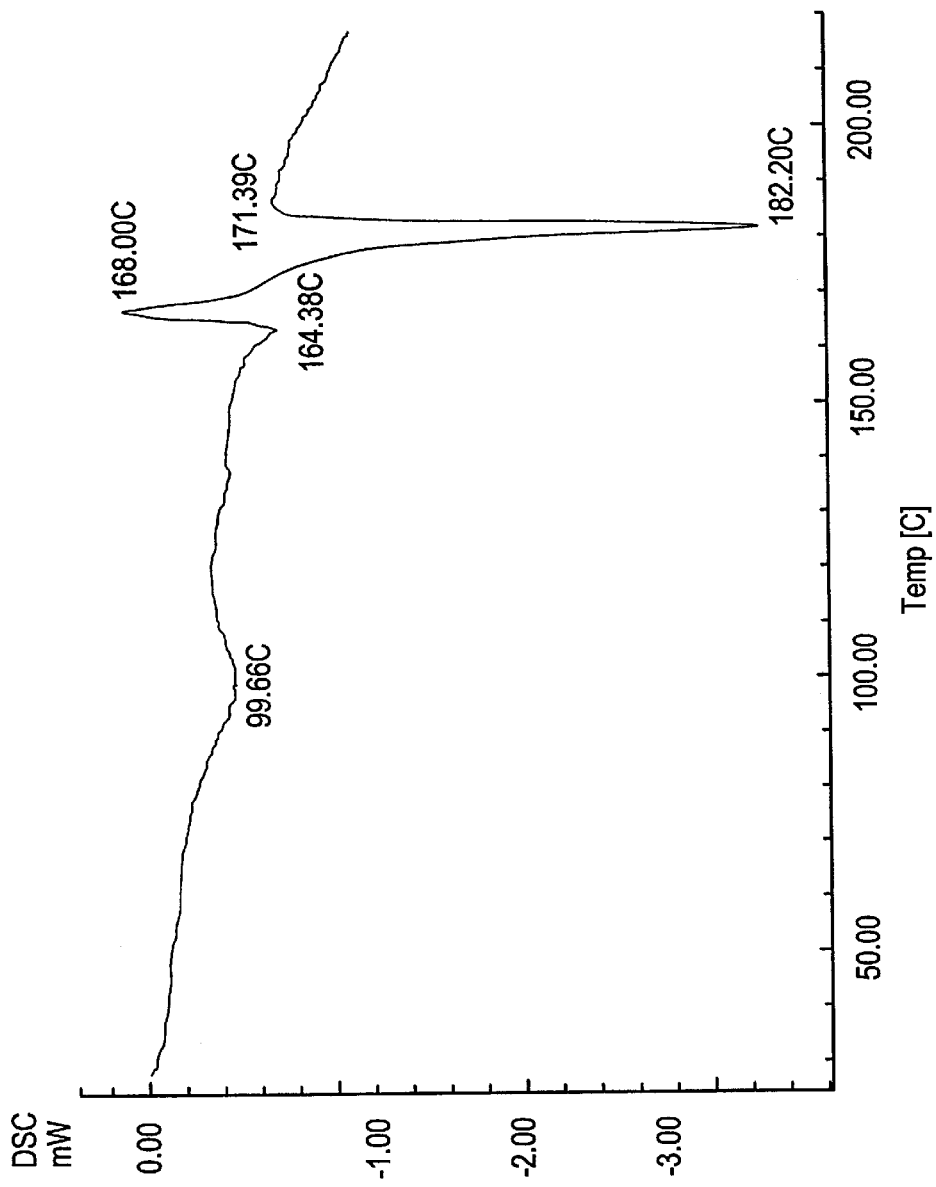

FIG. 15 is a characteristic differential scanning calorimetric thermogram of Form III.

Figure 16:
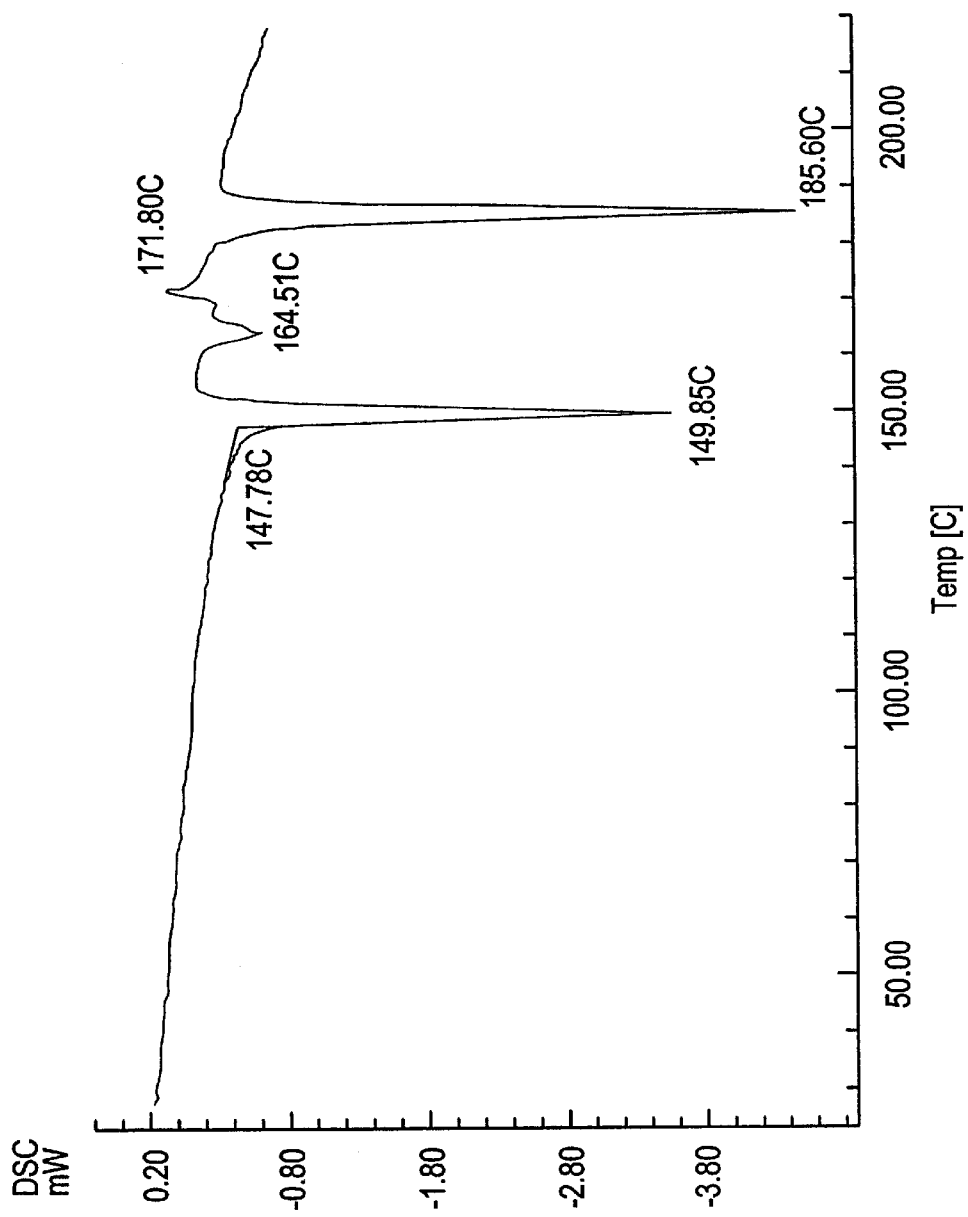

FIG. 16 is a characteristic differential scaring calorimetric thermogram of Form IV.

Figure 17:
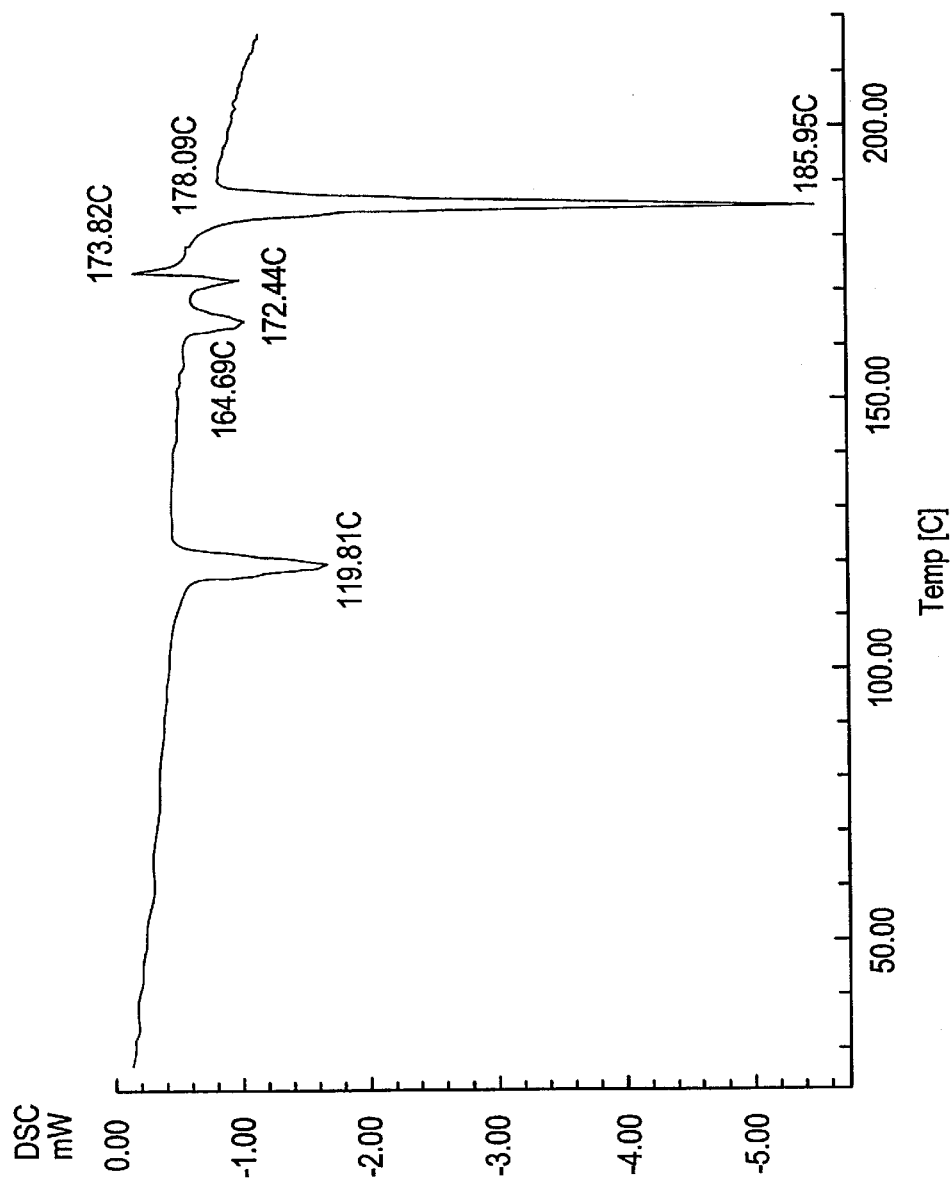

FIG. 17 is a characteristic differential scanning calorimetric thermogram of Form V.

Figure 18:
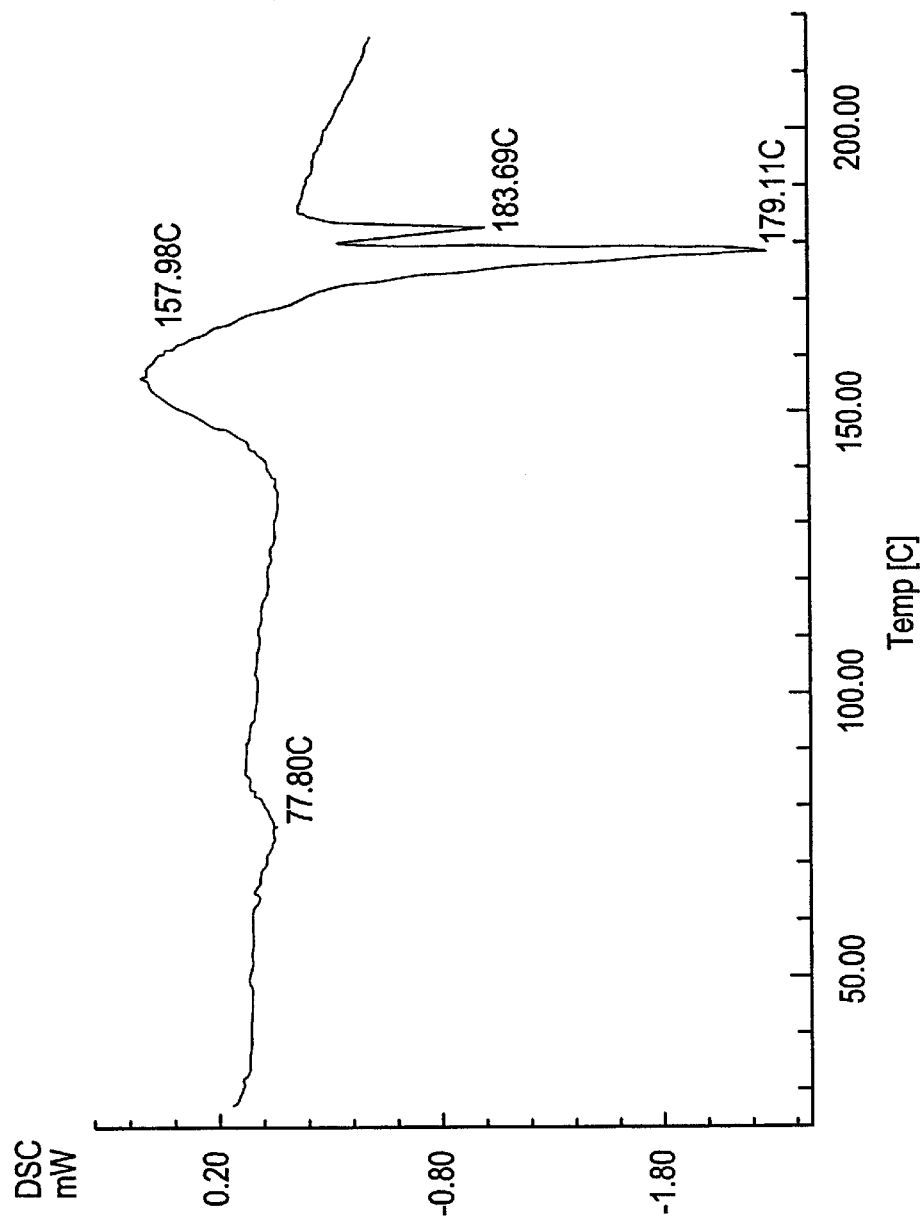

FIG. 18 is a characteristic differential scanning calorimetric thermogram of Form VI.

Figure 19:
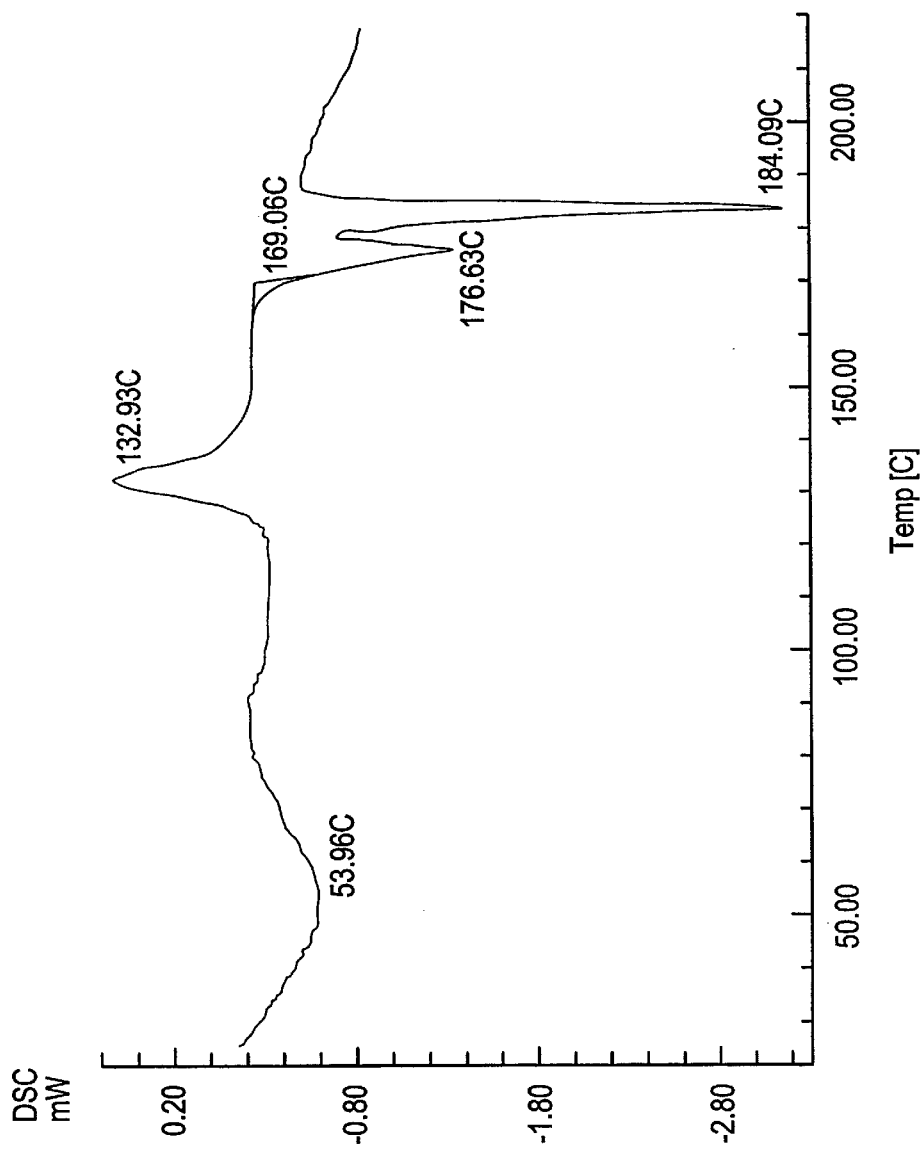

FIG. 19 is a characteristic differential scanning calorimetric thermogram of Form VII.

Figure 20:
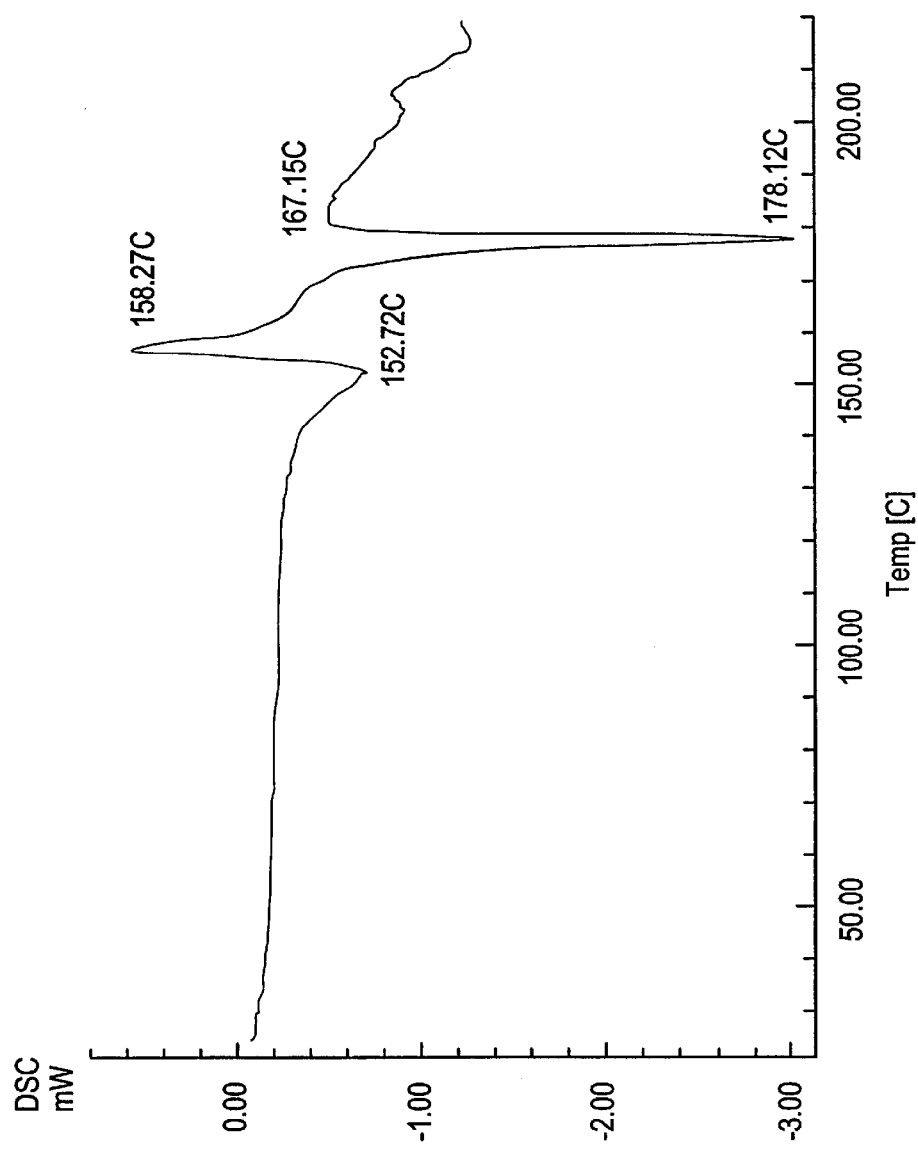

FIG. 20 is a characteristic differential scanning calorimetric thermogram of Form VIII.

Figure 21:
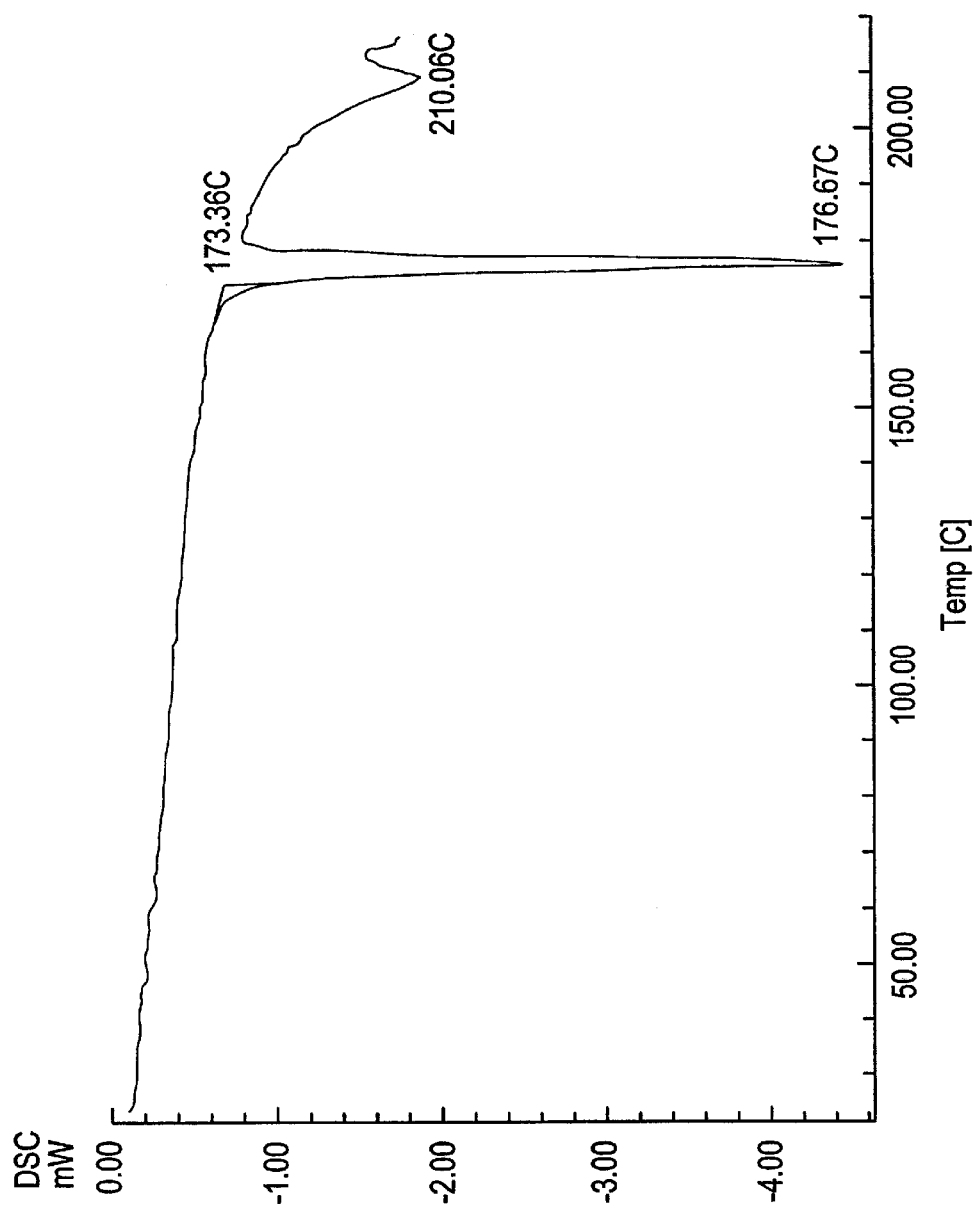

FIG. 21 is a characteristic differential scanning calorimetric thermogram of Form IX.

Figure 22:
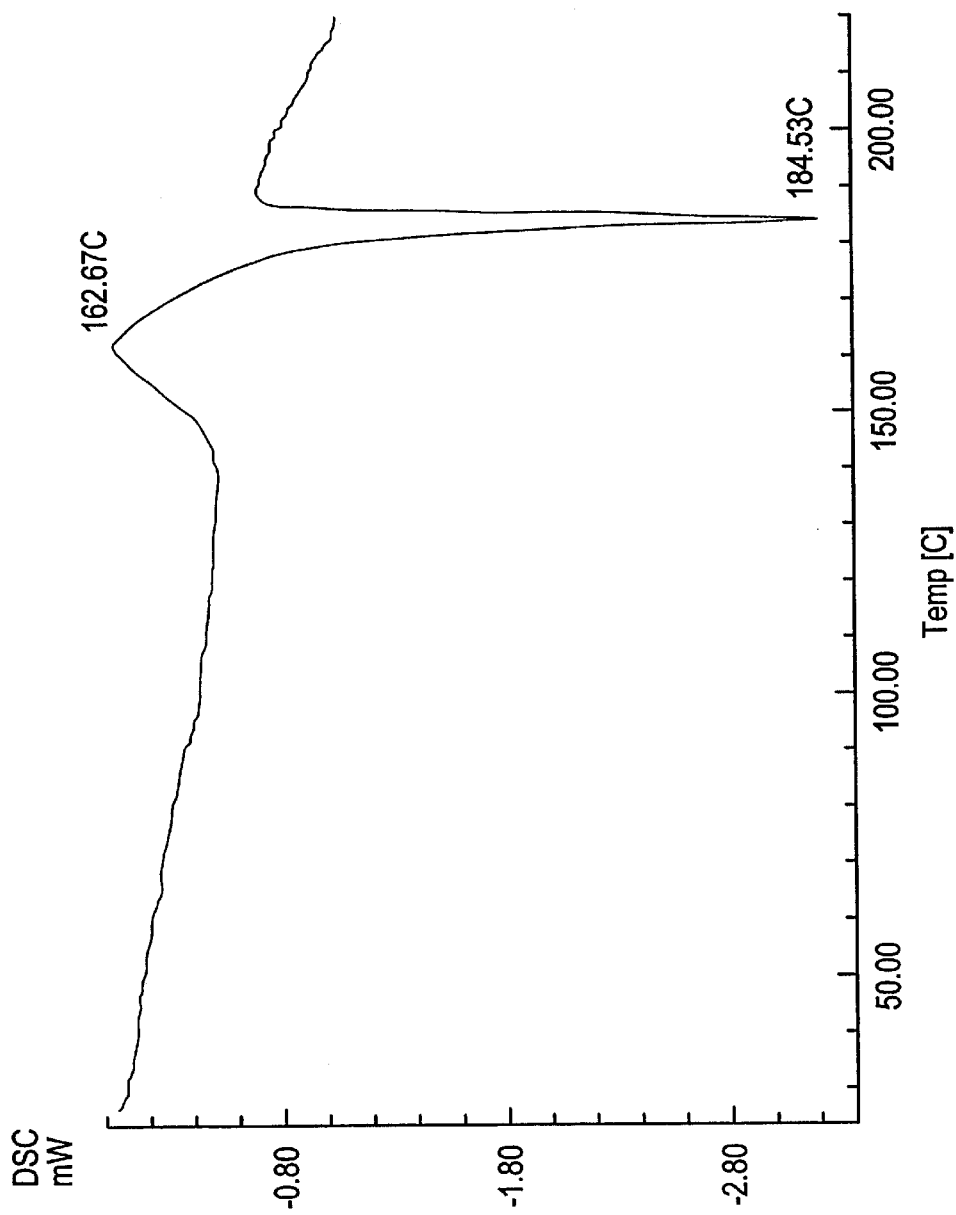

FIG. 22 is a characteristic differential scanning calorimetric thermogram of Form X.

Figure 23:
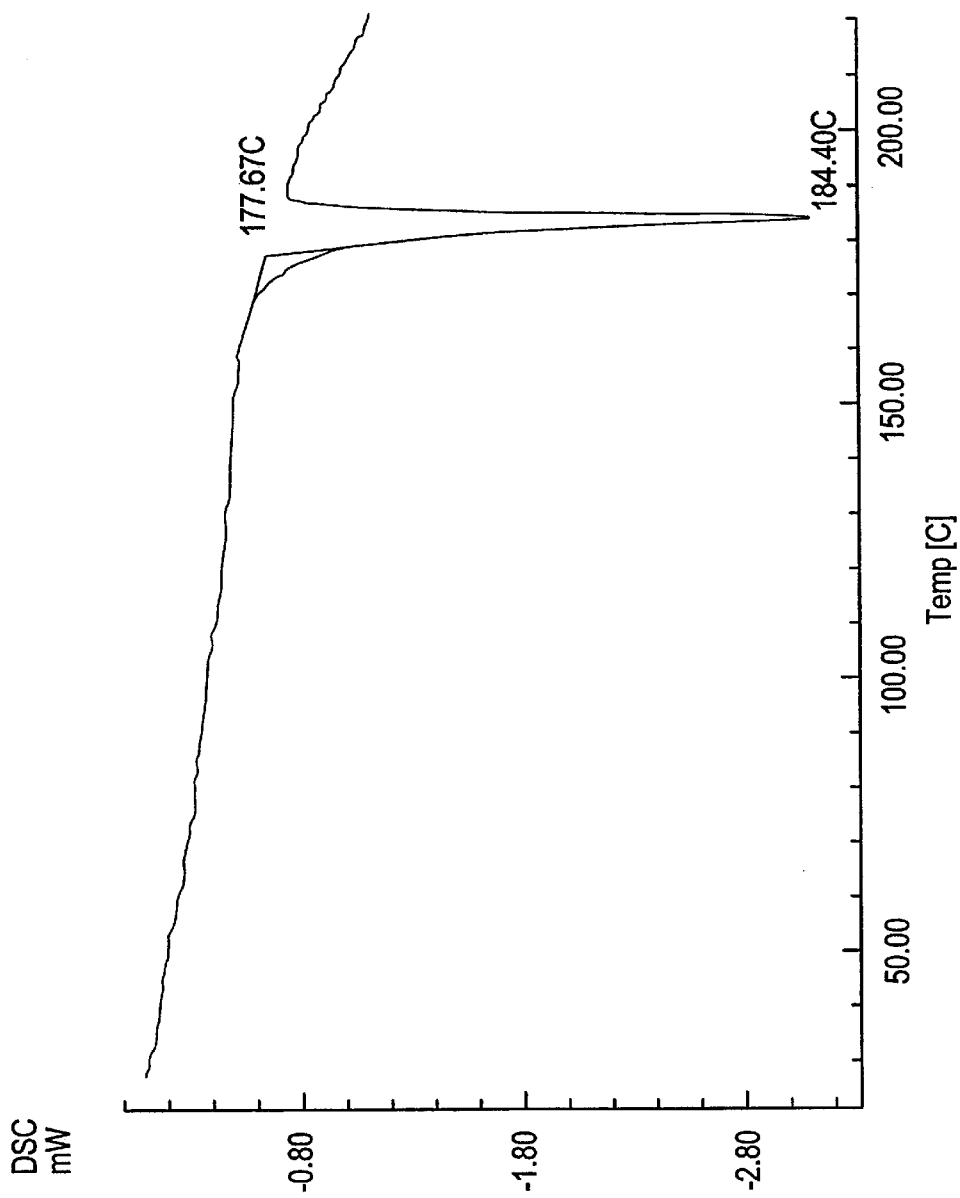

FIG. 23 is a characteristic differential scanning calorimetric thermogram of Form XI.

Figure 24:
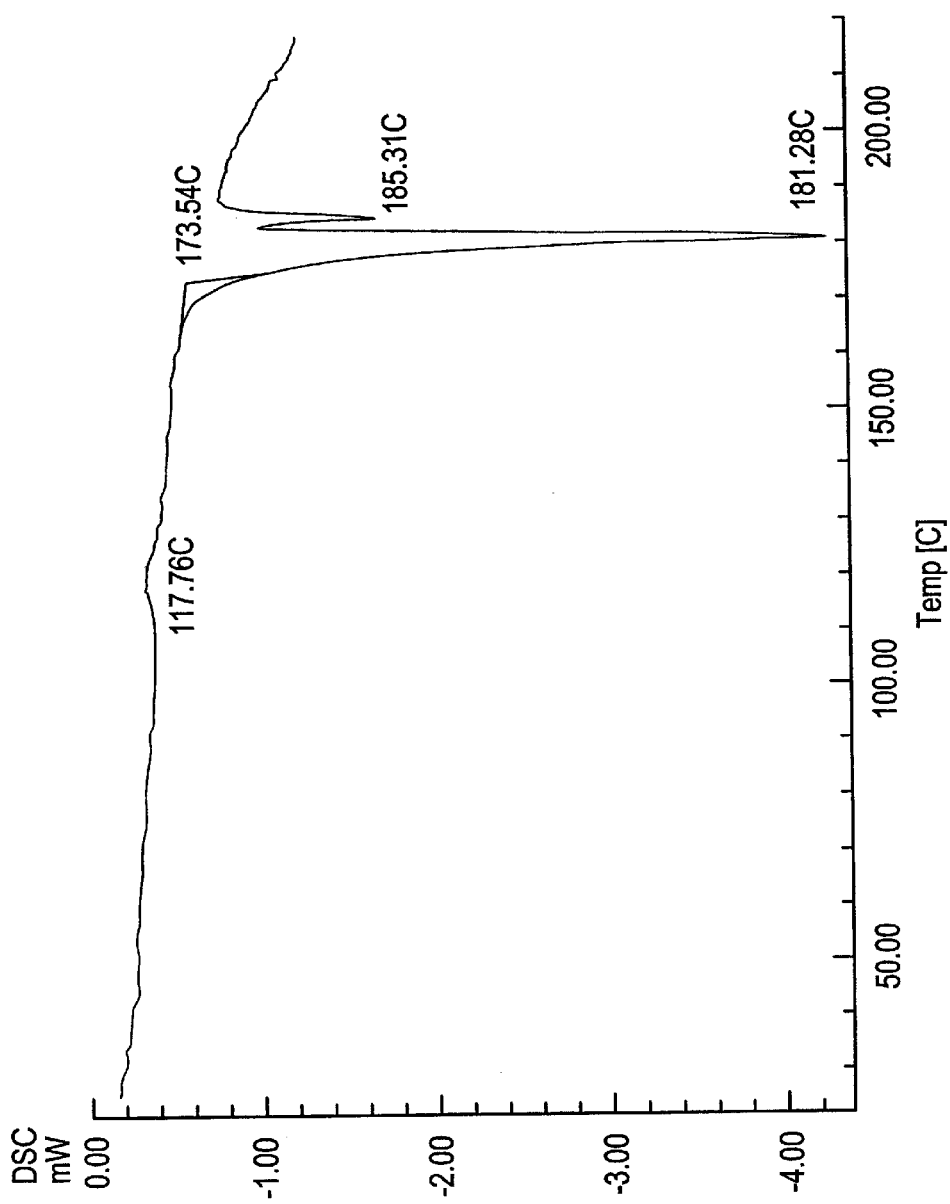

FIG. 24 is a characteristic differential scanning calorimetric thermogram of polymorphic form mixture.

FT-IR Spectrum was recorded in solid state as KBr dispersion using Perkin-Elmer 1650 FT-IR Spectrophotometer.

Figure 25:
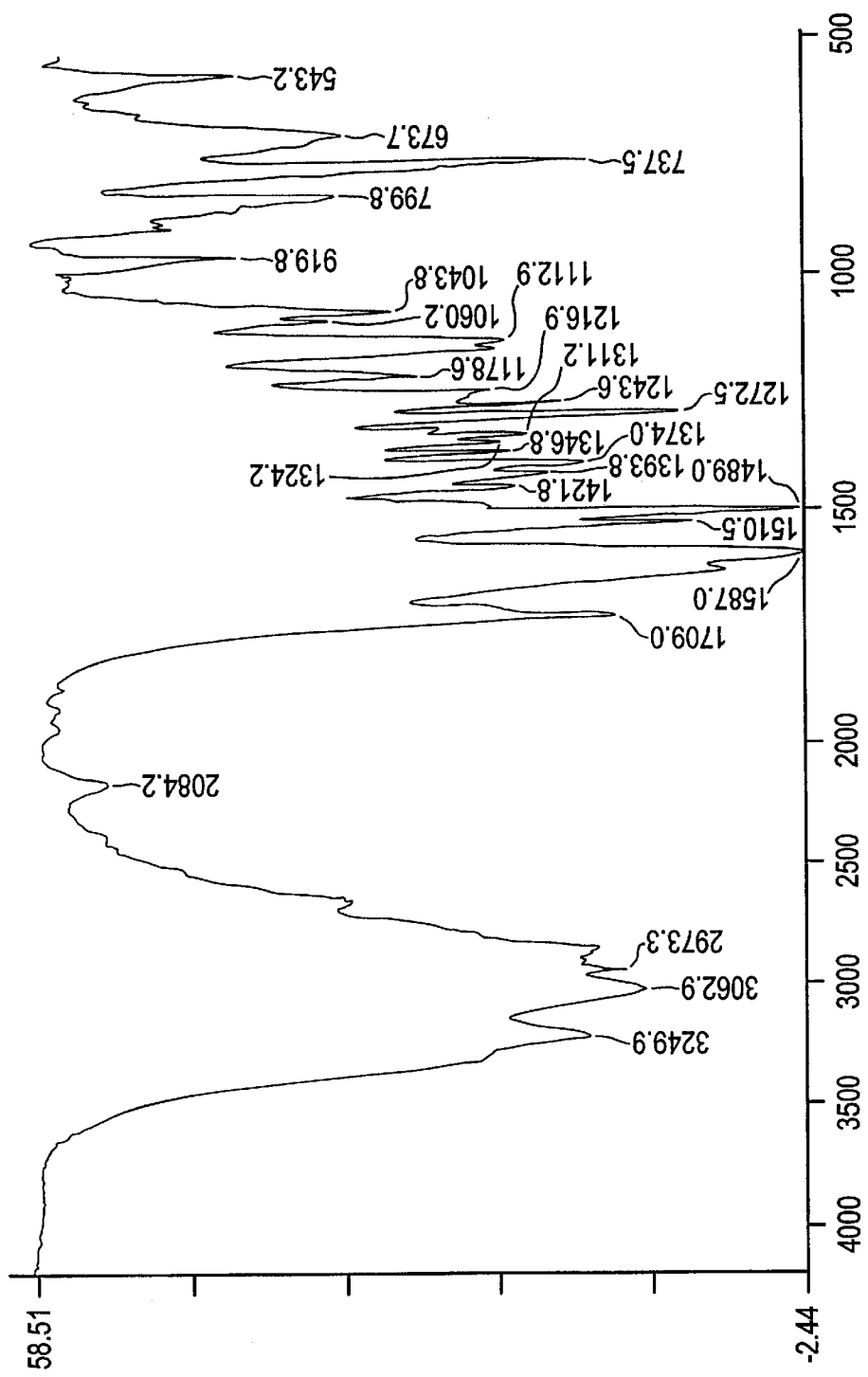

FIG. 25 is a characteristic infrared absorption spectrum of Form I in KBr.

Figure 26:
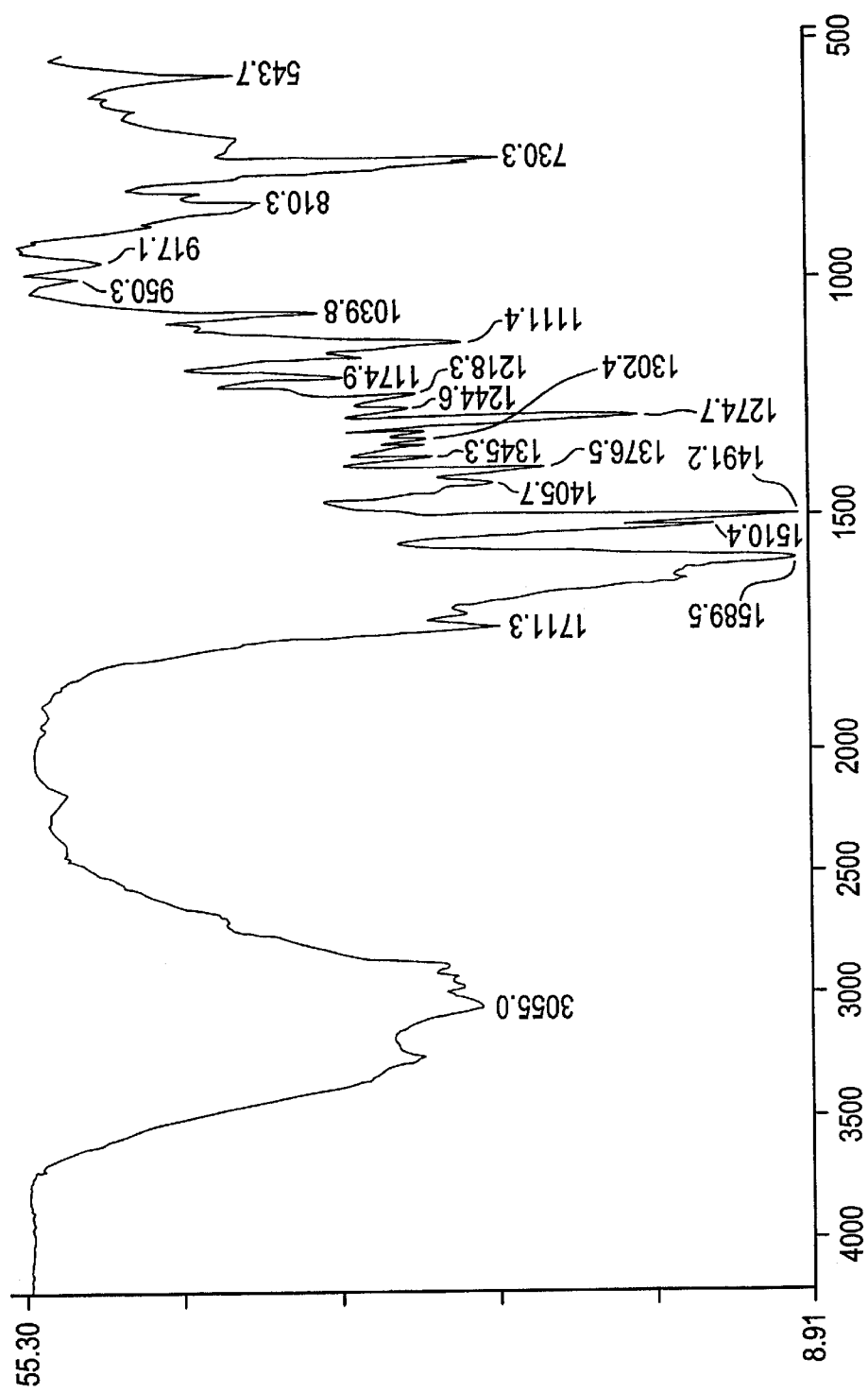

FIG. 26 is a characteristic infrared absorption spectrum of Form II in KBr.

Figure 27:
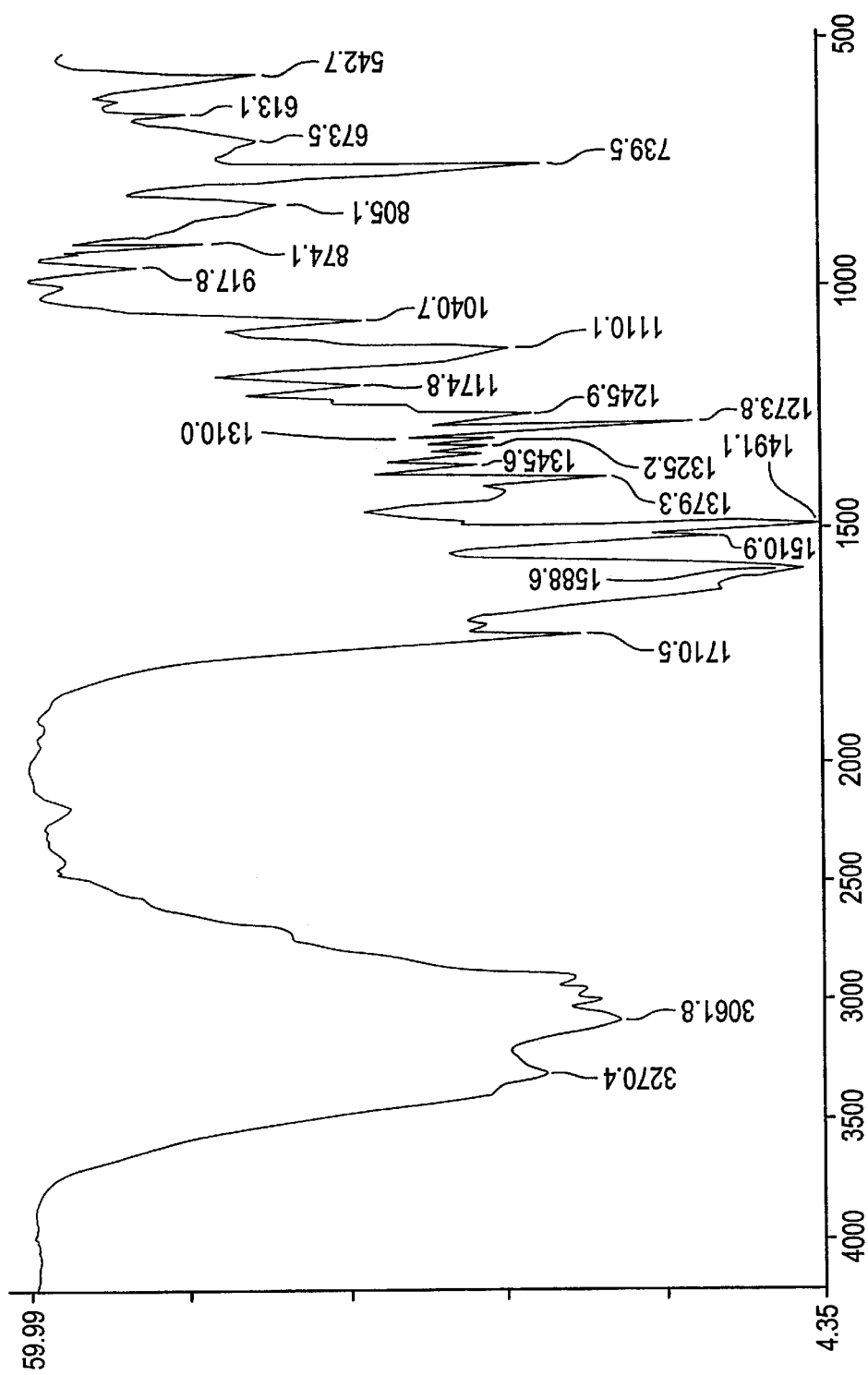

FIG. 27 is a characteristic infrared absorption spectrum of Form III in KBr.

Figure 28:
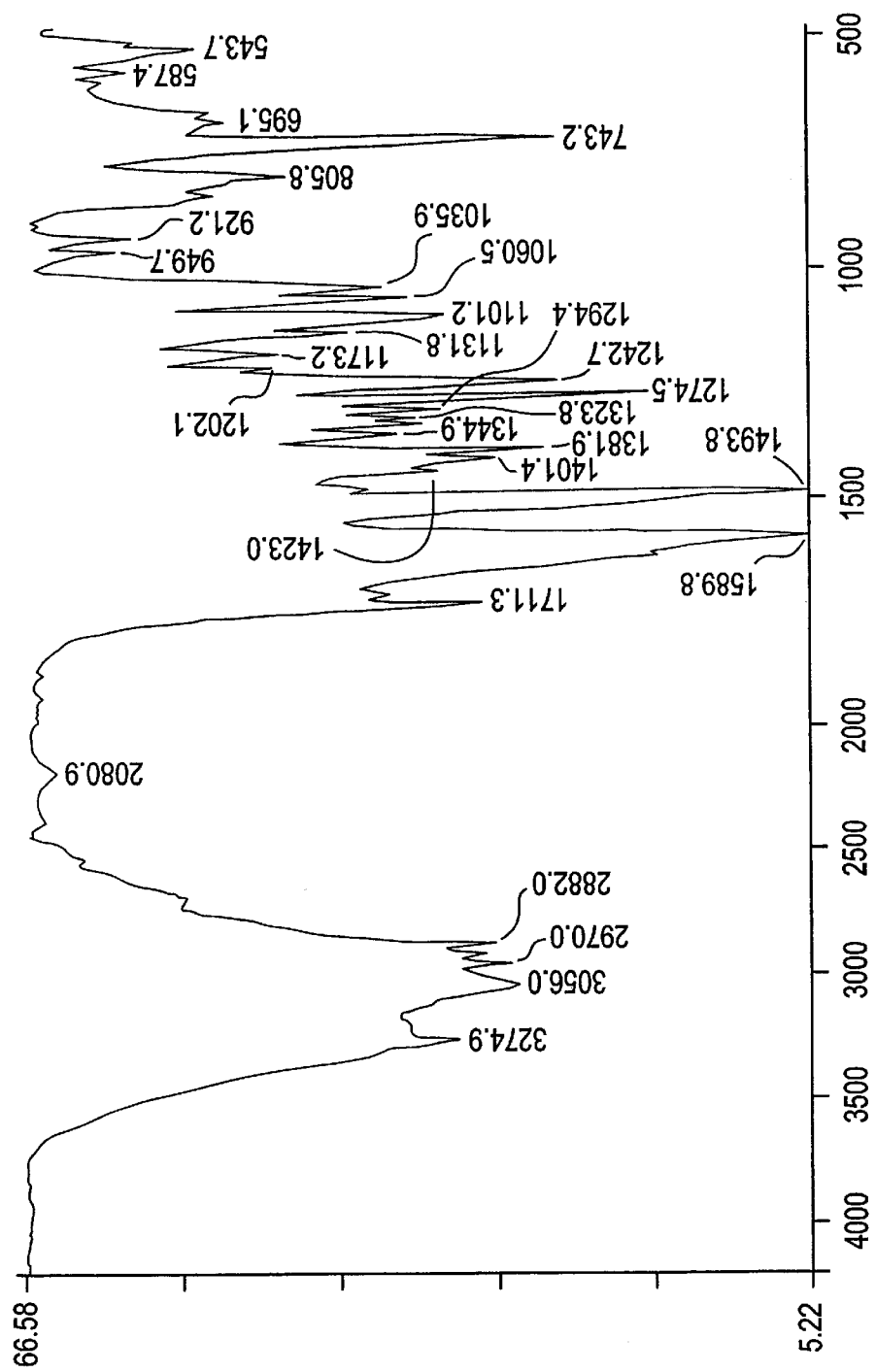

FIG. 28 is a characteristic infrared absorption spectrum of Form IV in KBr.

Figure 29:
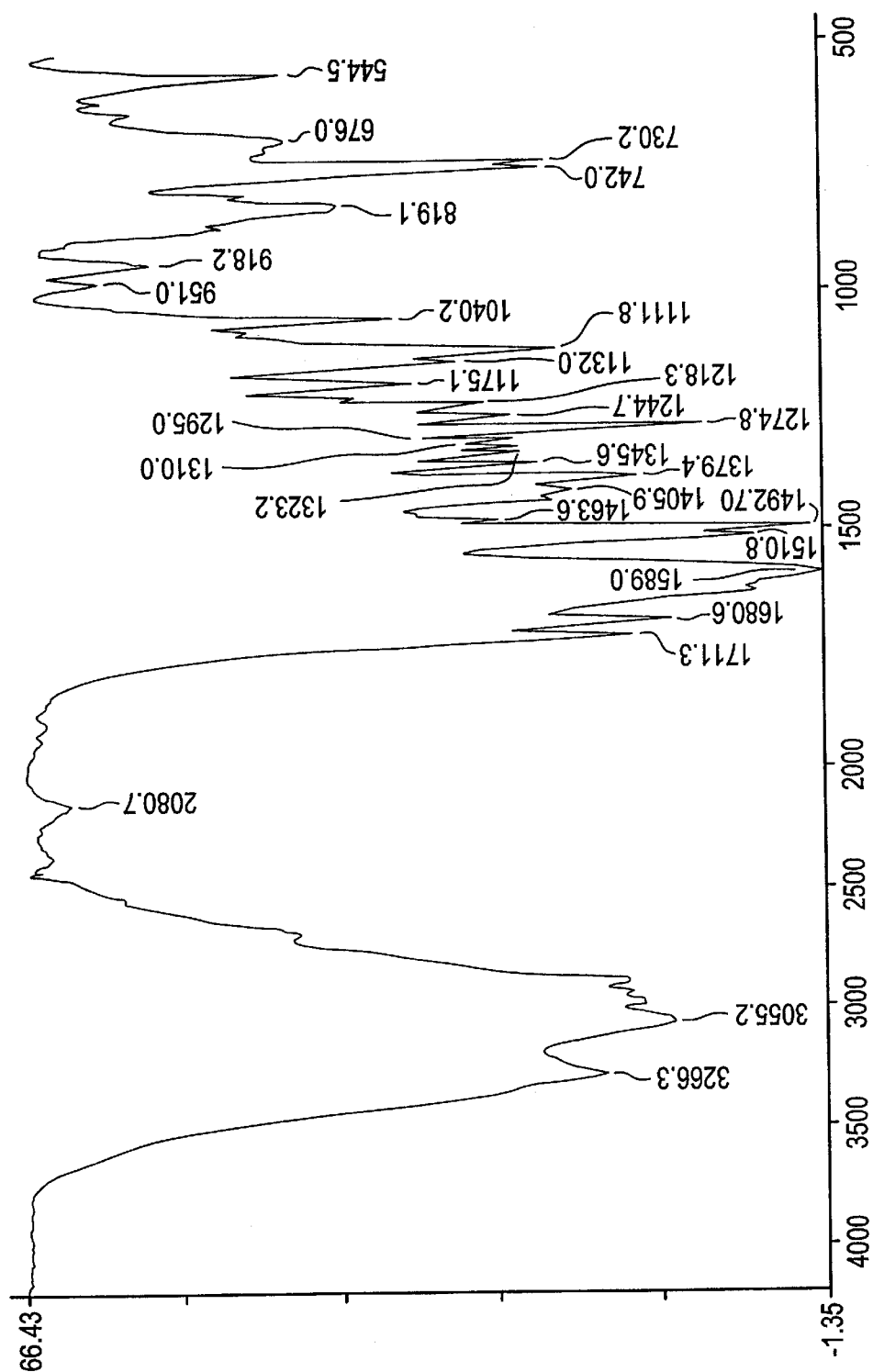

FIG. 29 is a characteristic infrared absorption spectrum of Form V in KBr.

Figure 30:
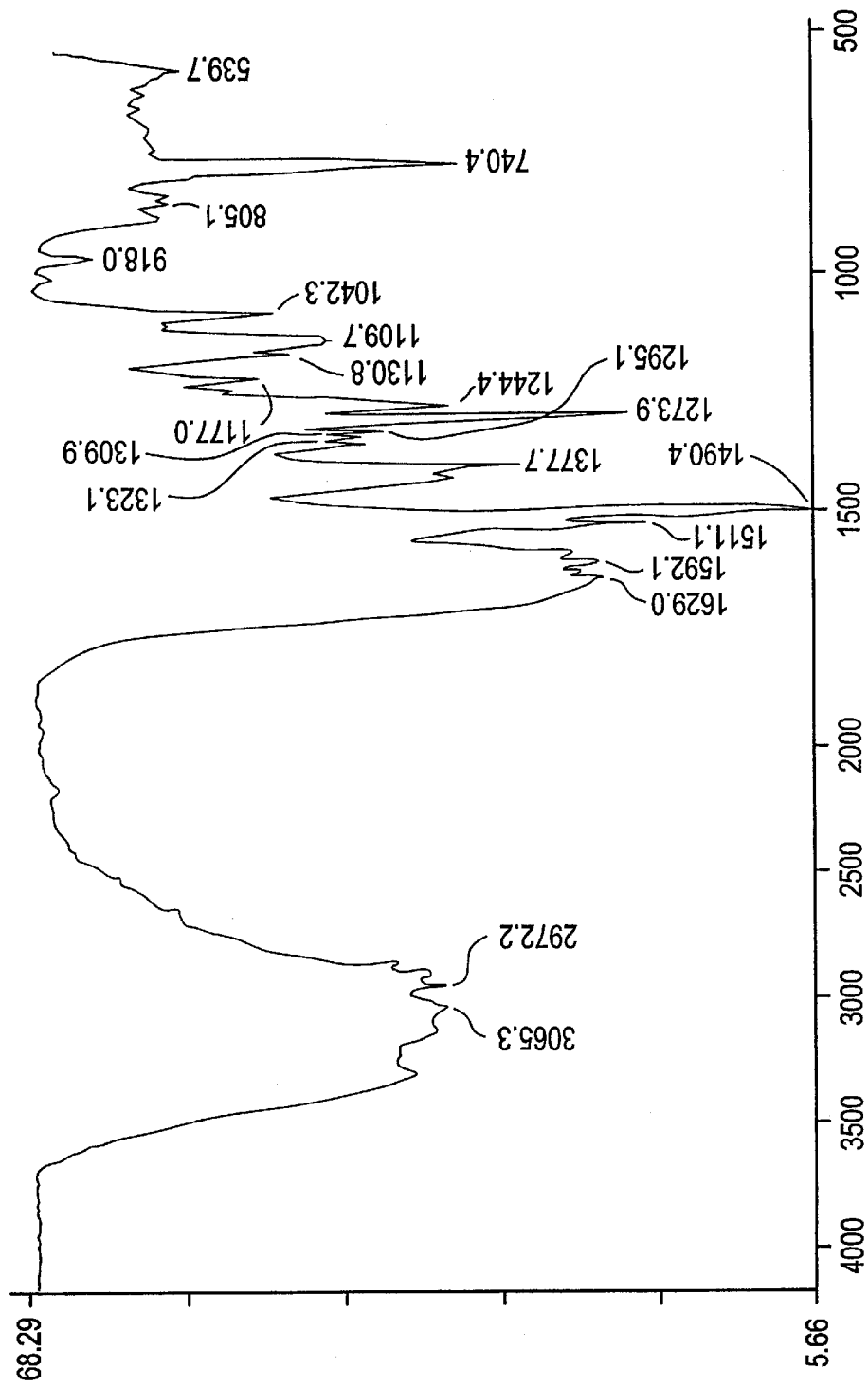

FIG. 30 is a characteristic infrared absorption spectrum of Form VI in KBr.

Figure 31:
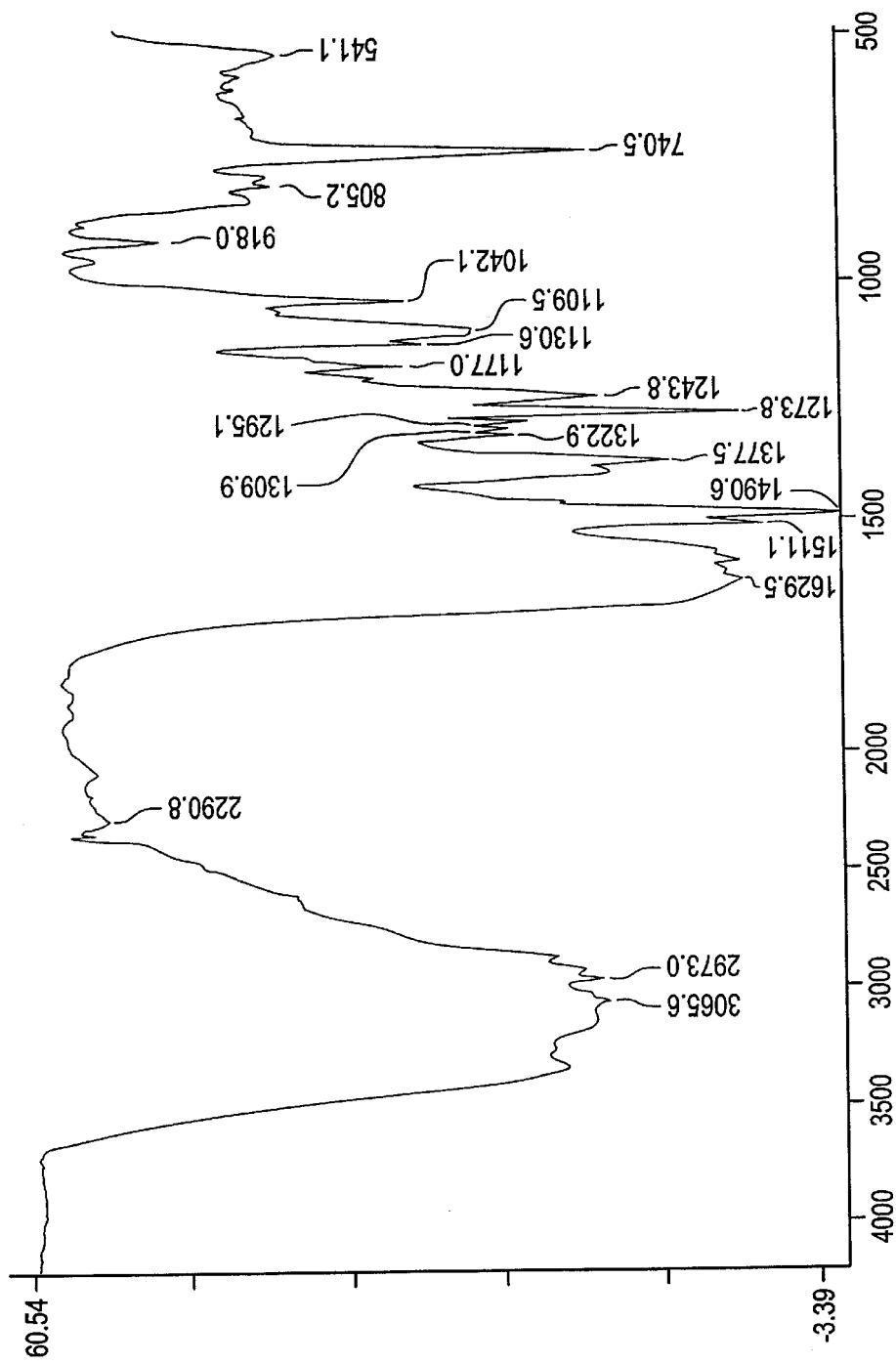

FIG. 31 is a characteristic infrared absorption spectrum of Form VII in KBr.

Figure 32:
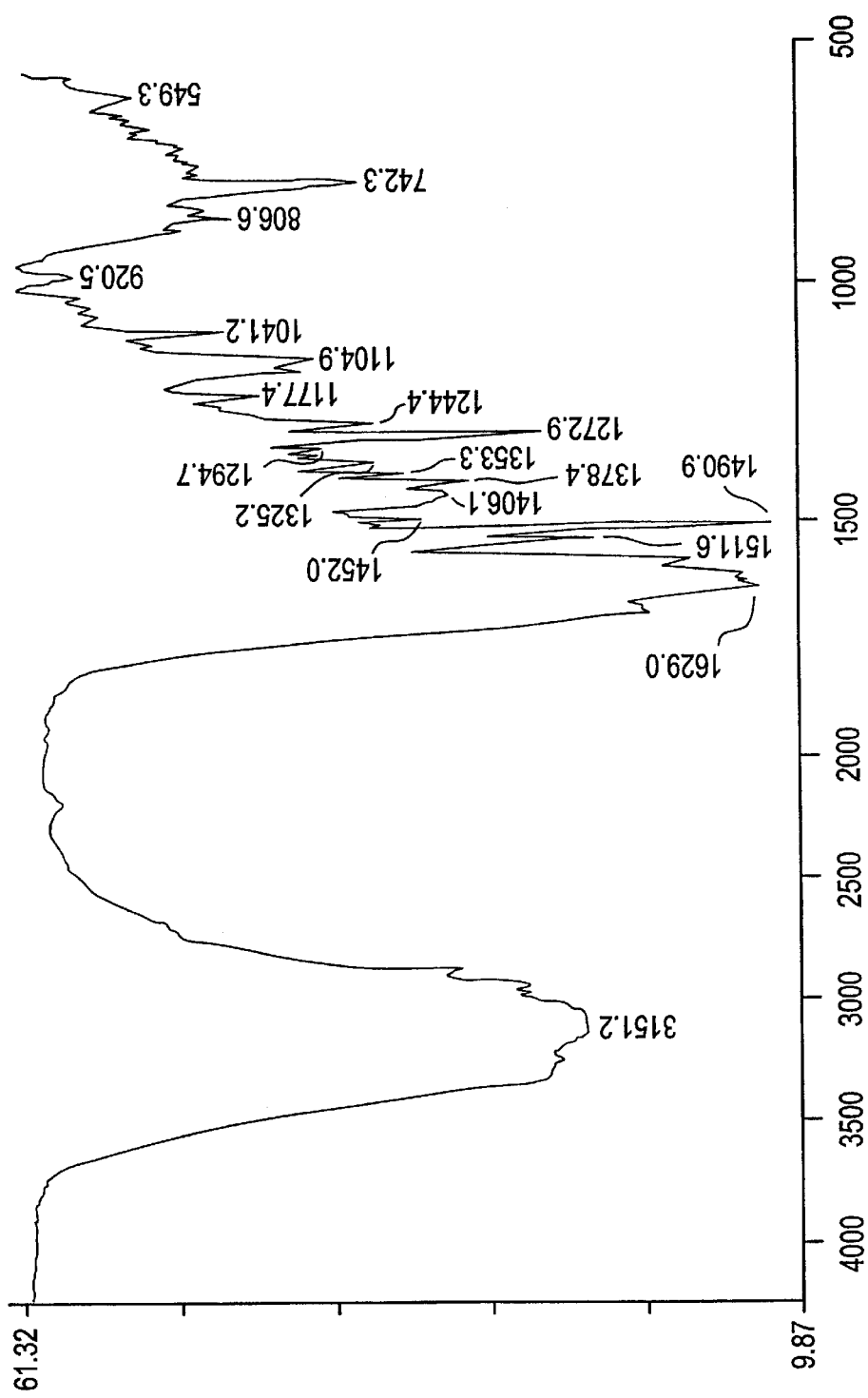

FIG. 32 is a characteristic infrared absorption spectrum of Form VIII in KBr.

Figure 33:
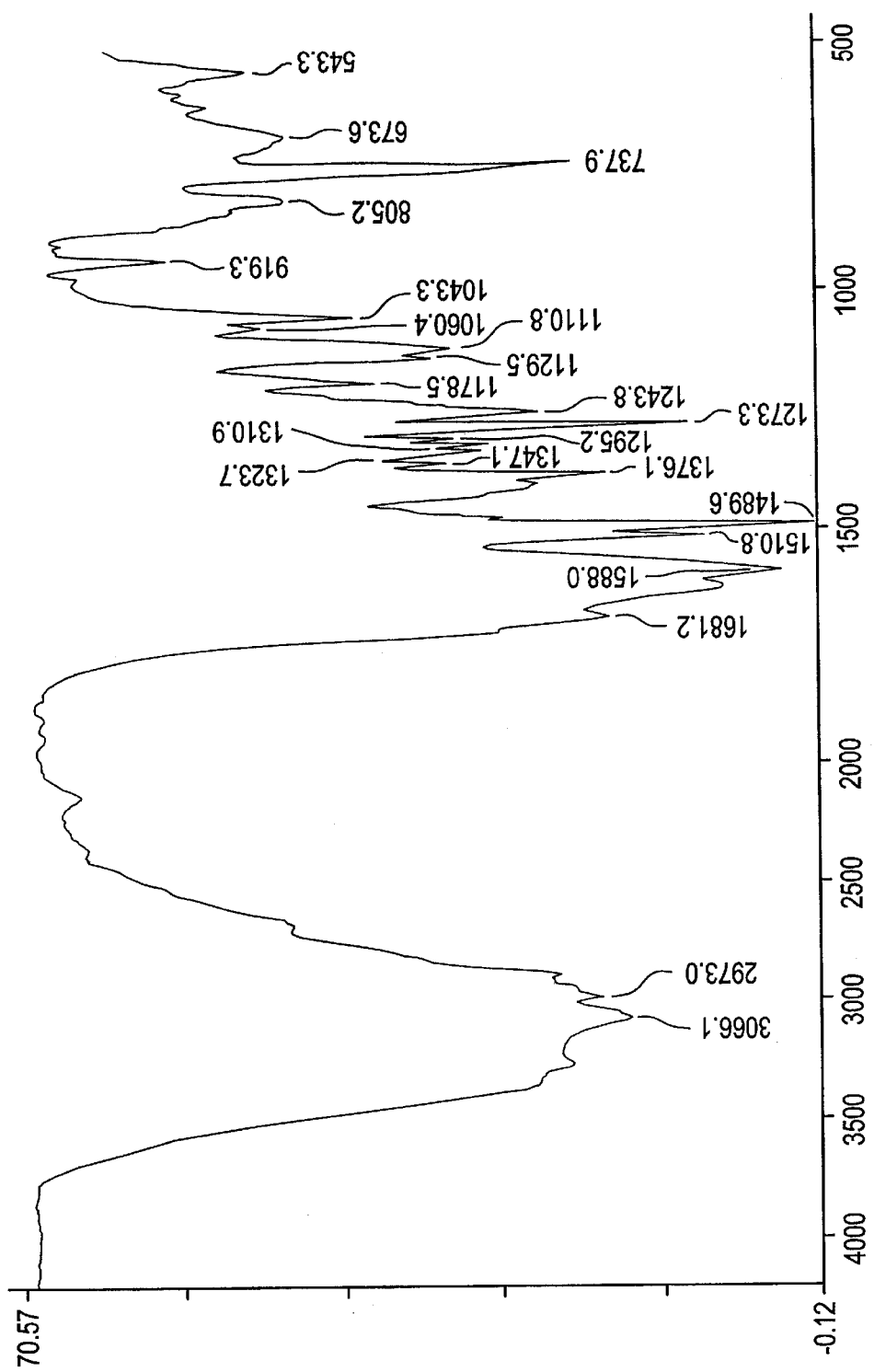

FIG. 33 is a characteristic infrared absorption spectrum of Form IX in KBr.

Figure 34:
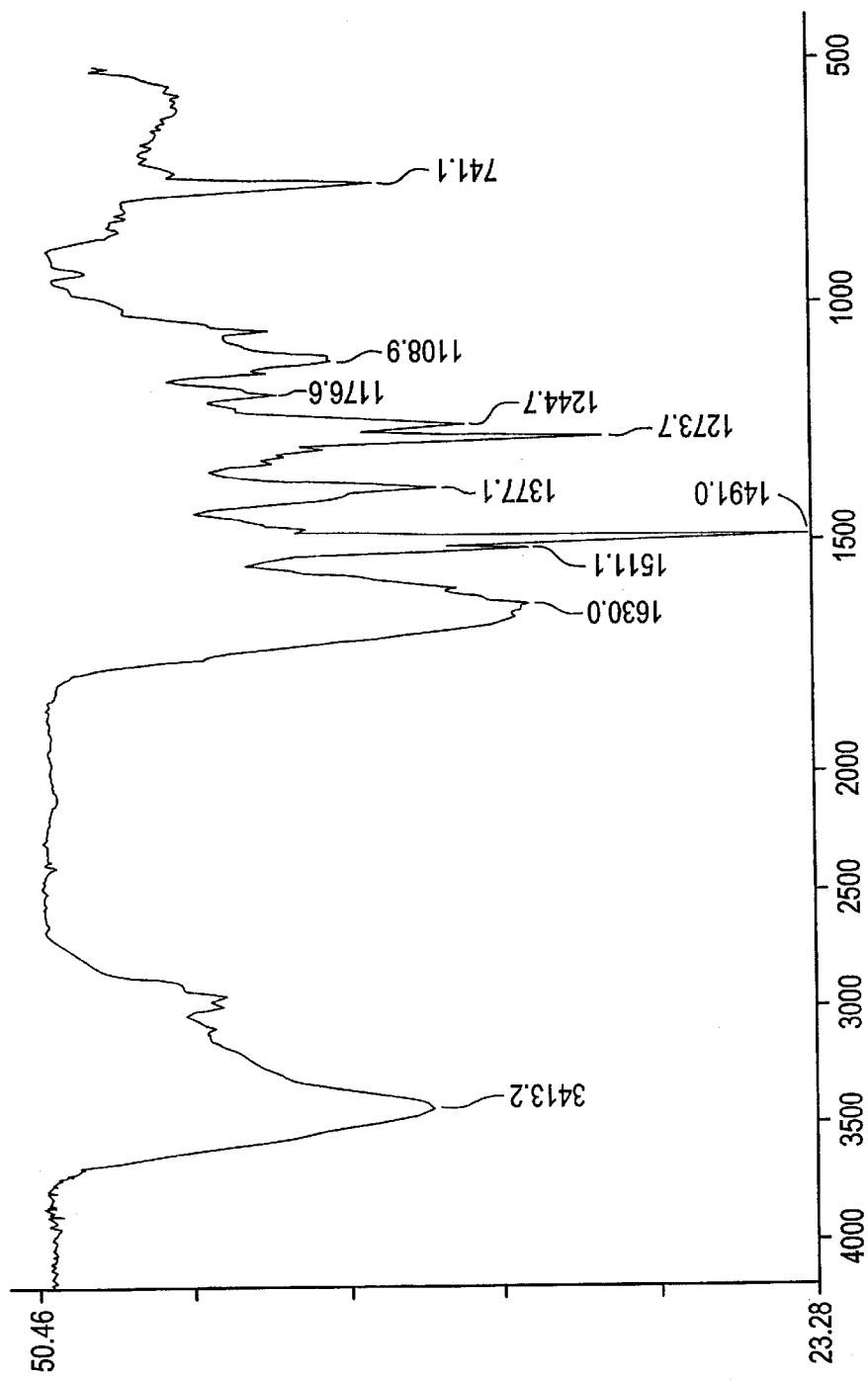

FIG. 34 is a characteristic infrared absorption spectrum of Form X in KBr.

Figure 35:
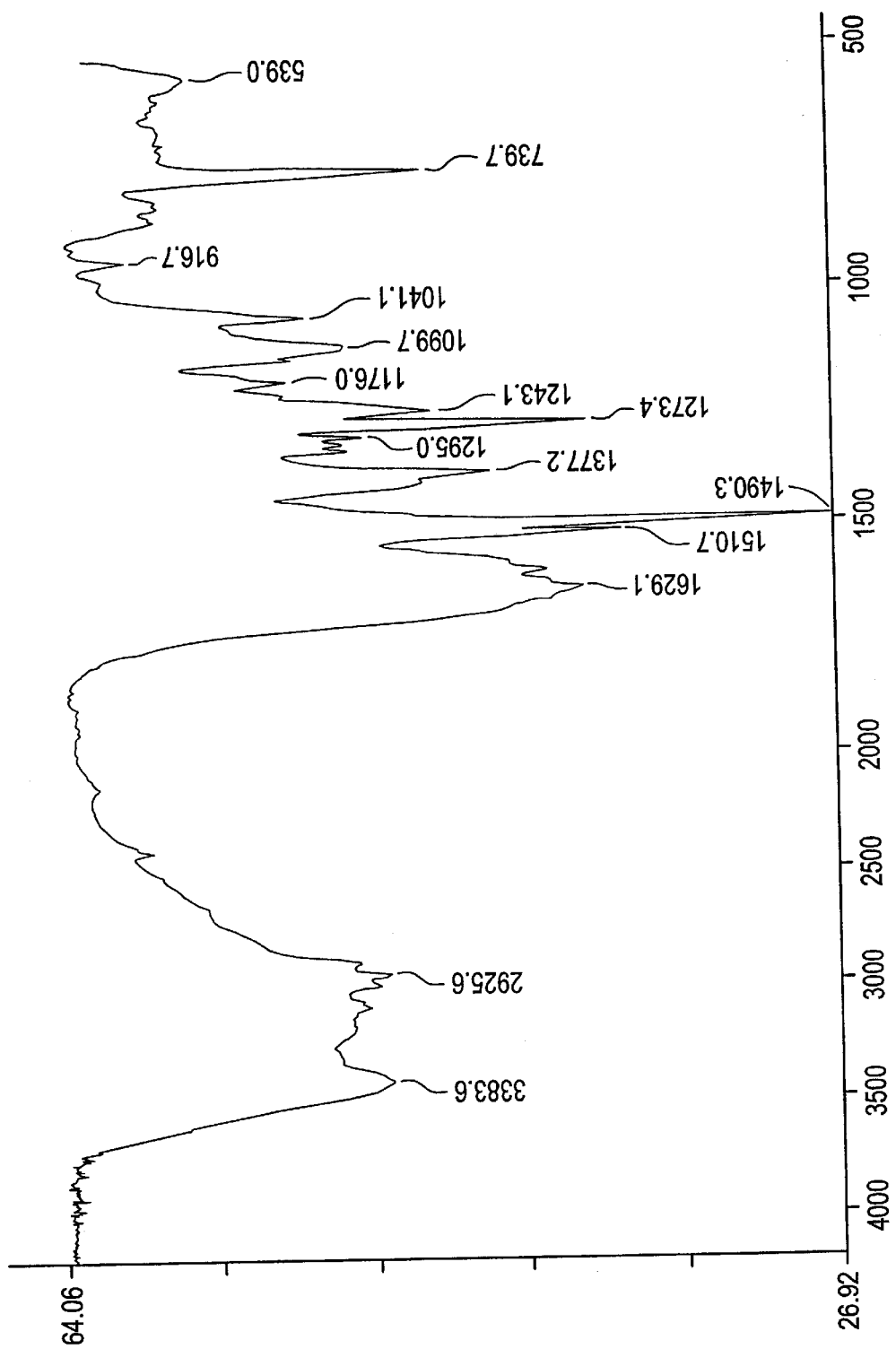

FIG. 35 is a characteristic infrared absorption spectrum of Form XI in KBr.

Figure 36:
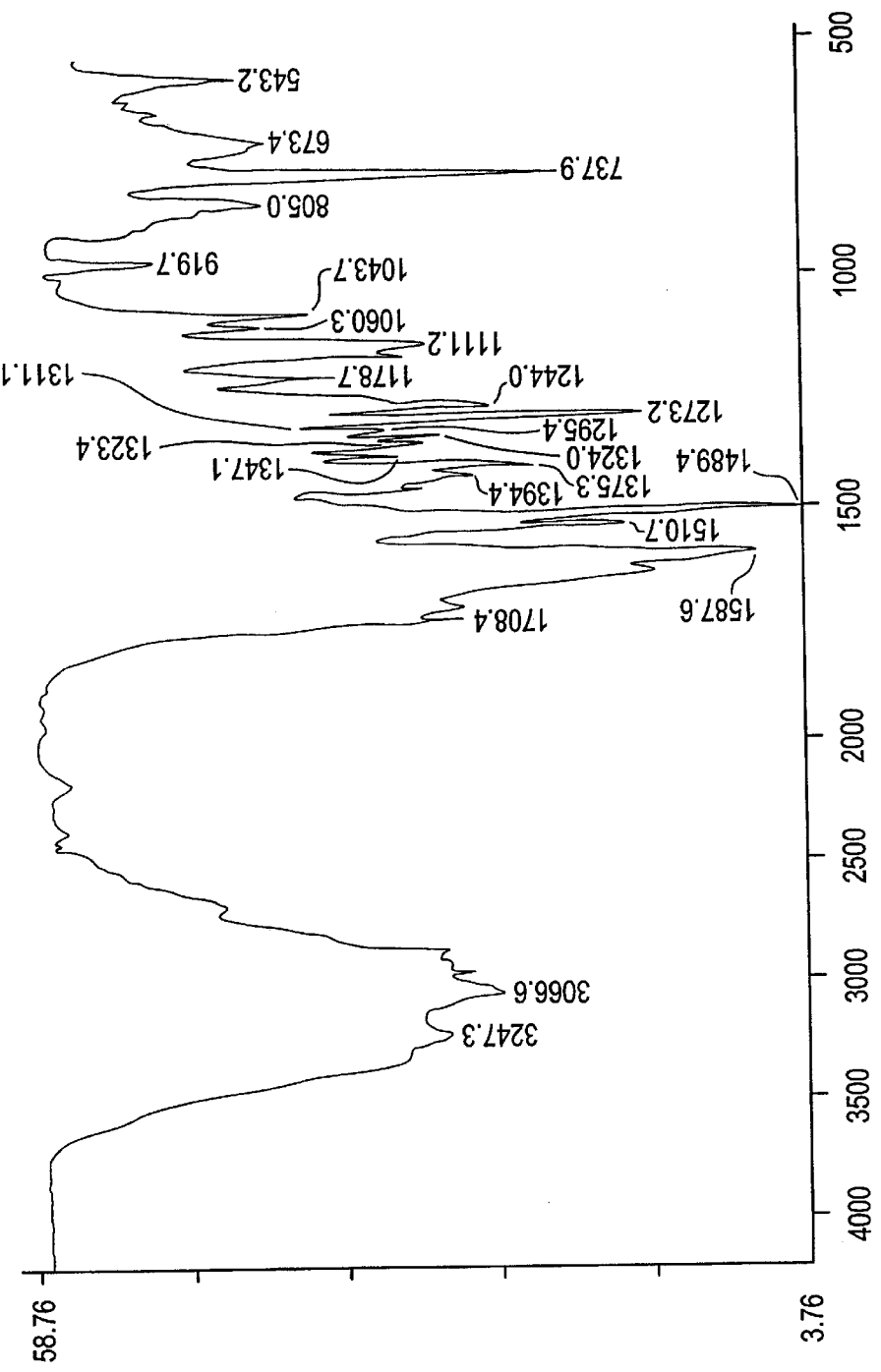

FIG. 36 is a characteristic infrared absorption spectrum of polymorphic form mixture in KBr.

According to a feature of the present invention, there is provided a novel polymorphic Form-I of L-arginine salt of (2S) 3-[4-[2-(phenoxazin-10-yl)ethoxy]phenyl]-2-ethoxypropanoic acid, having the formula I which is characterized by the following data DSC Endotherms at 181.21° C. (onset at 177.70° C.) (FIG. 13)

Figure 1:
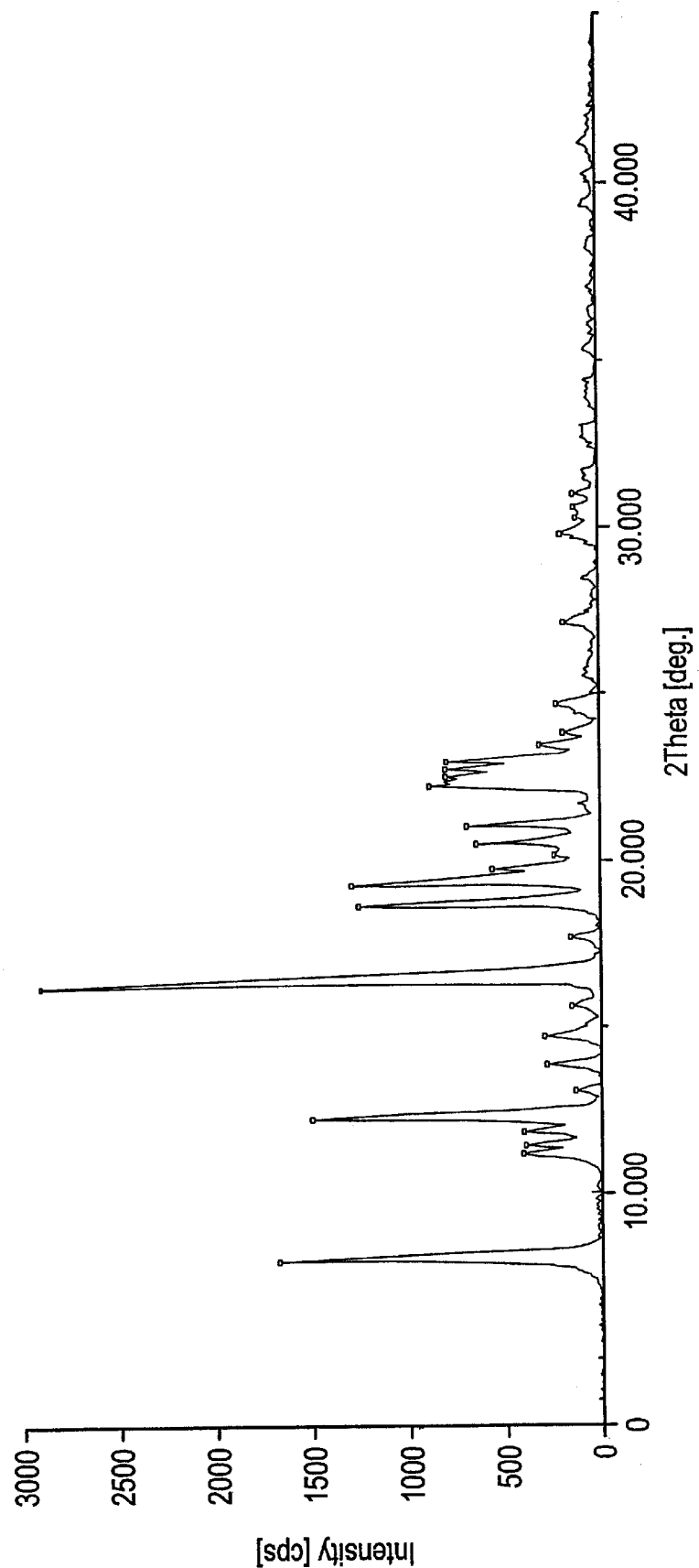
FIG. 1 is a characteristic X-ray powder diffraction pattern of Form I.

X-ray powder diffraction ($2\theta$): 8.18, 12.40, 16.66, 18.80, 19.44, 22.32, 22.84, is 23.10, 23.50, 24.72, 29.84, (FIG. 1)

Infrared absorption bands ($cm^{-1}$): 3249, 3062, 1709, 1587, 1489, 1374, 1272, 1243, 1112, 1043, 9–19, 737, 673, 543, (FIG. 25)

According to another feature of the present invention, there is provided a novel polymorphic Form-II of L-arginine salt of (2S) 3-[4-[2-(phenoxazin-10-yl)ethoxy]phenyl]-2-ethoxypropanoic acid, having the formula I which is characterized by the following data:

DSC: Endotherms at 131° C. 166.24° C. and 178.96° C. (FIG. 14)

Exotherm at 169.73° C.

Figure 2:
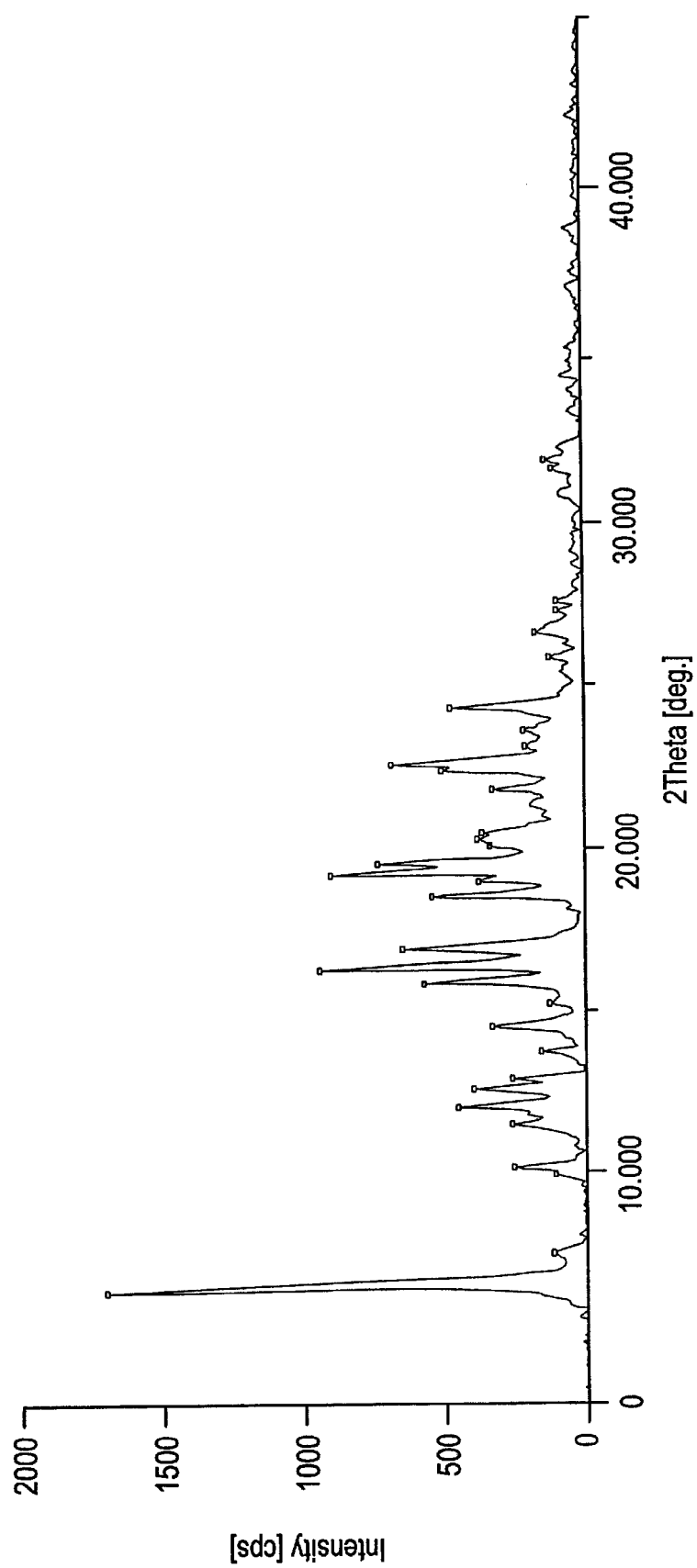
FIG. 2 is a characteristic X-ray powder diffraction pattern of Form II.

X-ray powder diffraction ($2\theta$) 6.78, 11.5, 12.08, 16.44, 19.34, 22.30, 22.72, 24.40, 26.66 (FIG. 2)

Infrared absorption bands ($cm^{-1}$): 3055, 1711, 1589, 1510, 1491, 1376, 1274, 1111, 1039, 810, 730, 543, (FIG. 26)

According to yet another feature of the present invention, there is provided a novel polymorphic Form-III of L-arginine salt of (2S) 3-[4-[2-(phenoxazin-10-yl)ethoxy] phenyl]-2-ethoxypropanoic acid, having the formula I which is characterized by the following data:

DSC: Endotherm at 182.20° C. (onset at 171° C.) (FIG. 15)

Small endotherms at 99.66° C., 164.38° C.

Exotherm at 168.00° C.

Figure 3:
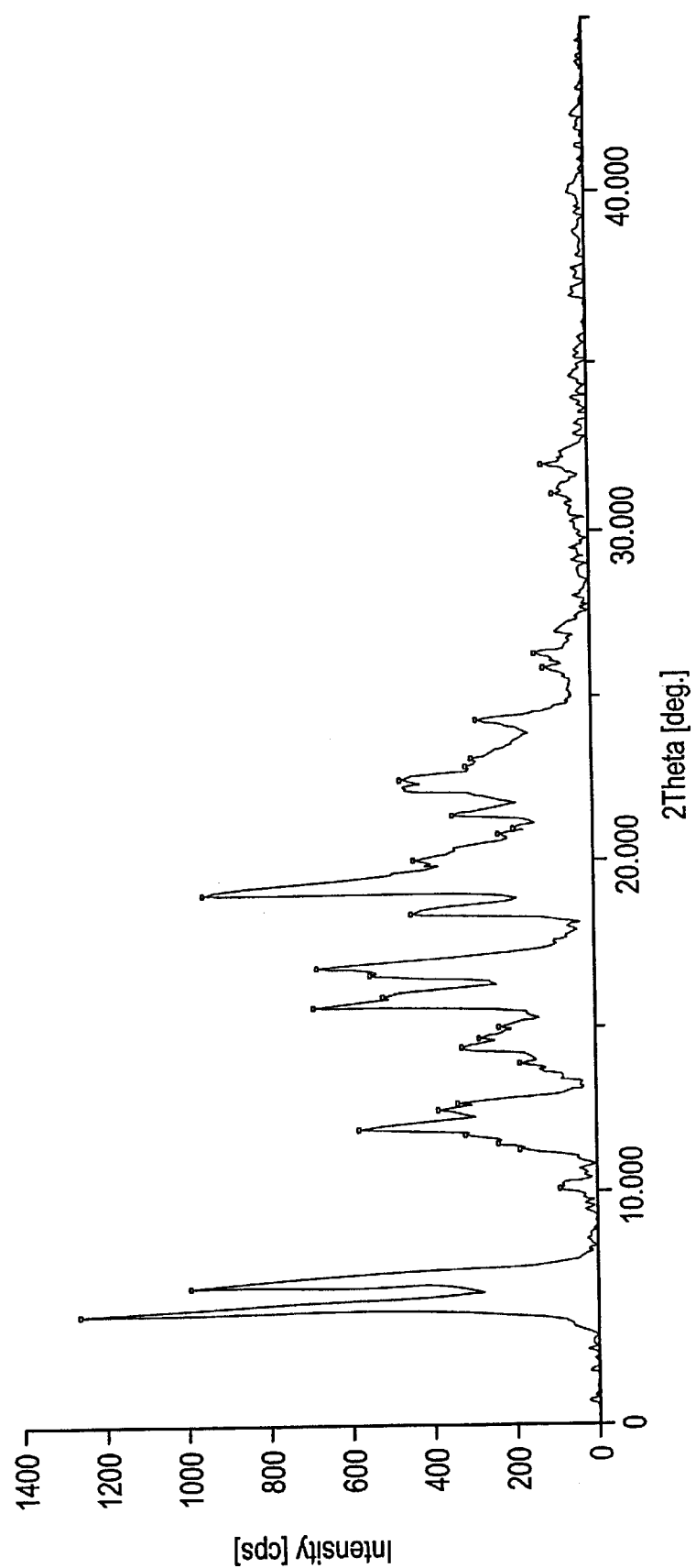
FIG. 3 is a characteristic X-ray powder diffraction pattern of Form III.

X-ray powder diffraction ($2\theta$): 6.80, 12.10, 15.84, 17.02, 19–40, 22.32, 22.68, 24.38, 26.36, (FIG. 3).

Infrared absorption bands ($cm^{-1}$): 3061, 1710, 1588, 1510, 1491, 1379, 1273, 1110, 1040, 805, 739, and 543, (FIG. 27)

According to yet another feature of the present invention, there is provided a novel polymorphic Form-IV of L-arginine salt of (2S) 3-[4-[2-(phenoxazin-10-yl)ethoxy] phenyl]-2-ethoxypropanoic acid, having the formula I which is characterized by the following data:

DSC: Endotherms at 149.85° C., 185.60° C. (onset at 147.78° C.) (FIG. 16)

Small Endotherm at 164.51° C.

Small Exotherm at 171.80° C.

Figure 4:
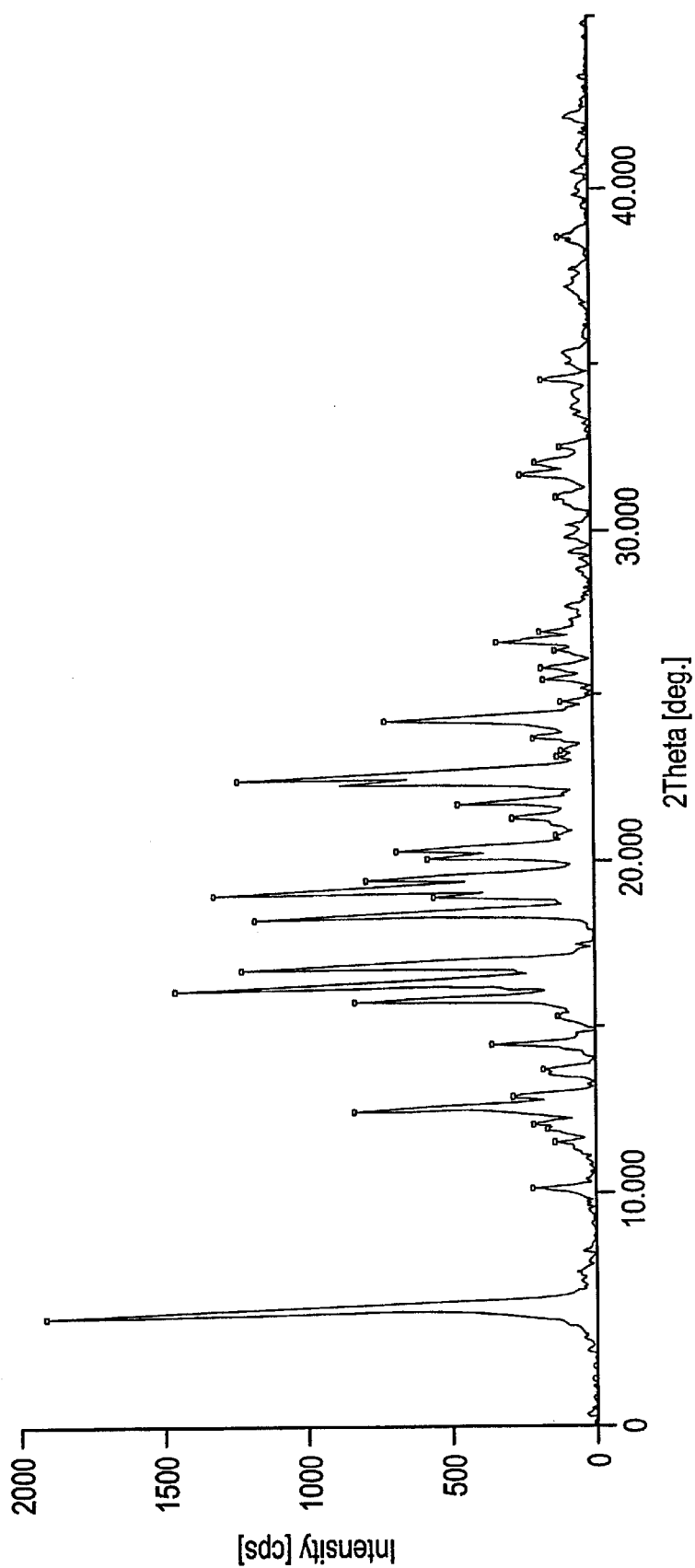
FIG. 4 is a characteristic X-ray powder diffraction pattern of Form IV.

X-ray powder diffraction ($2\theta$): 6.78, 12.66, 15.96, 16.54, 19.34, 22.78, 24.42, 26.70, 31.70, (FIG. 4)

Infrared absorption bands ($cm^{-1}$): 3056, 1711, 1589, 1493, 1381, 1274, 1242, 1101, 1060, 805, 743, and 543.7, (FIG. 28)

According to yet another feature of the present invention, there is provided a novel polymorphic Form-V of L-arginine salt of (2S) 3-[4-[2-(phenoxazin-10-yl)ethoxy]phenyl]-2-ethoxypropanoic acid, having the formula I which is characterized by the following data:

DSC: Endotherm at 185.95° C., (onset at 178.09° C.) (FIG. 17)

Small endotherms at 119.81° C., 164.69° C., 172.44° C.

Small exotherm at 173.82° C.

Figure 5:
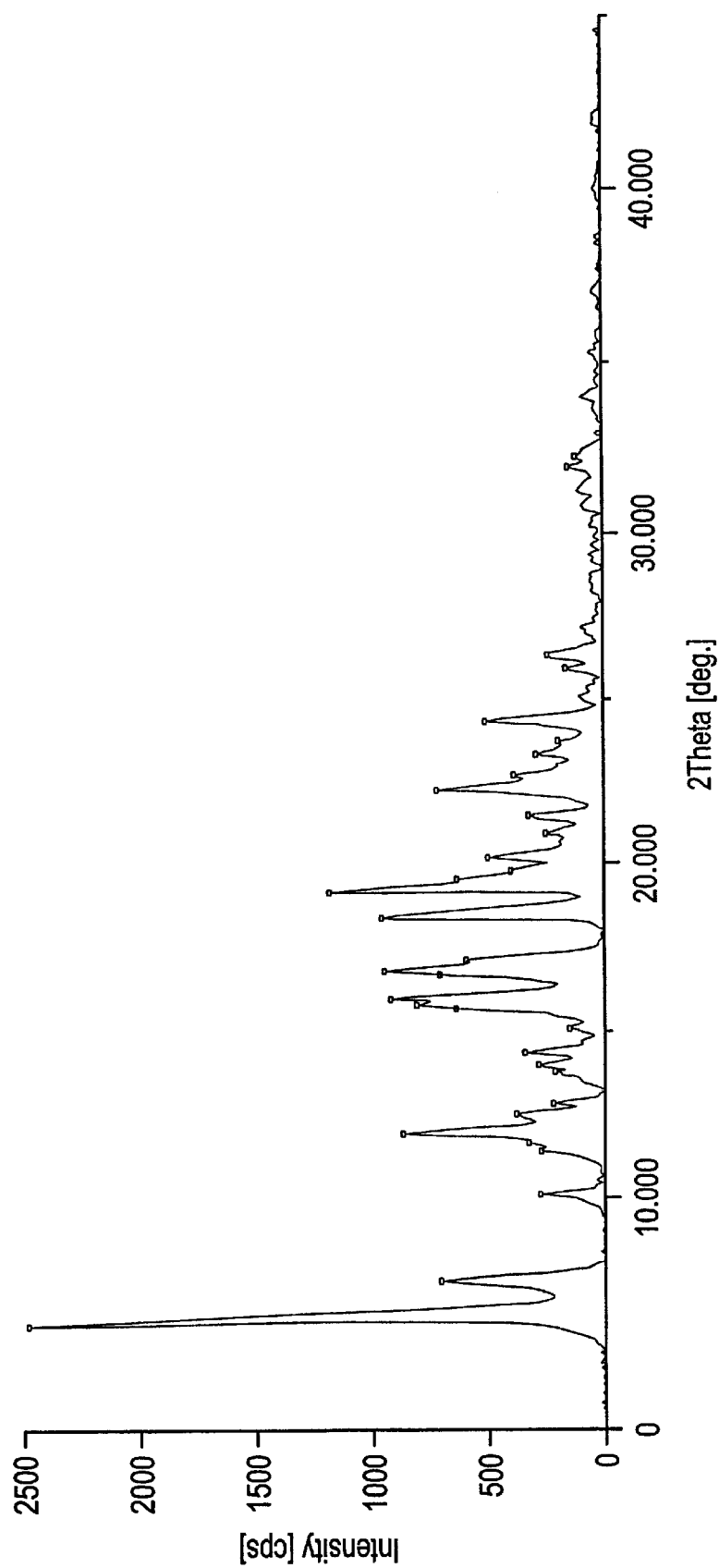
FIG. 5 is a characteristic X-ray powder diffraction pattern of Form V.

X-ray powder diffraction ($2\theta$): 6.76, 12.10, 15.96, 17.00, 18.50, 19.40, 22.38, 22.44, 24.44, 26.30, (FIG. 5)

Infrared absorption bands ($cm^{-1}$): 3266, 3055, 1711, 1589, 1510, 1492, 1379, 1274, 1175, 1111, 1040, 918, 819, 730, 676, 544, (FIG. 29)

According to yet another feature of the present invention, there is provided a novel polymorphic Form-VI of L-arginine salt of (2S) 3-[4-[2-(phenoxazin-10-yl)ethoxy]phenyl]-2-ethoxypropanoic acid, having the formula I which is characterized by the following data:

DSC: Endotherms at 179.11° C. and 183.69° C. (onset at 157.98° C.), (FIG. 18)

Small endotherm at 77.80° C.

Figure 6:
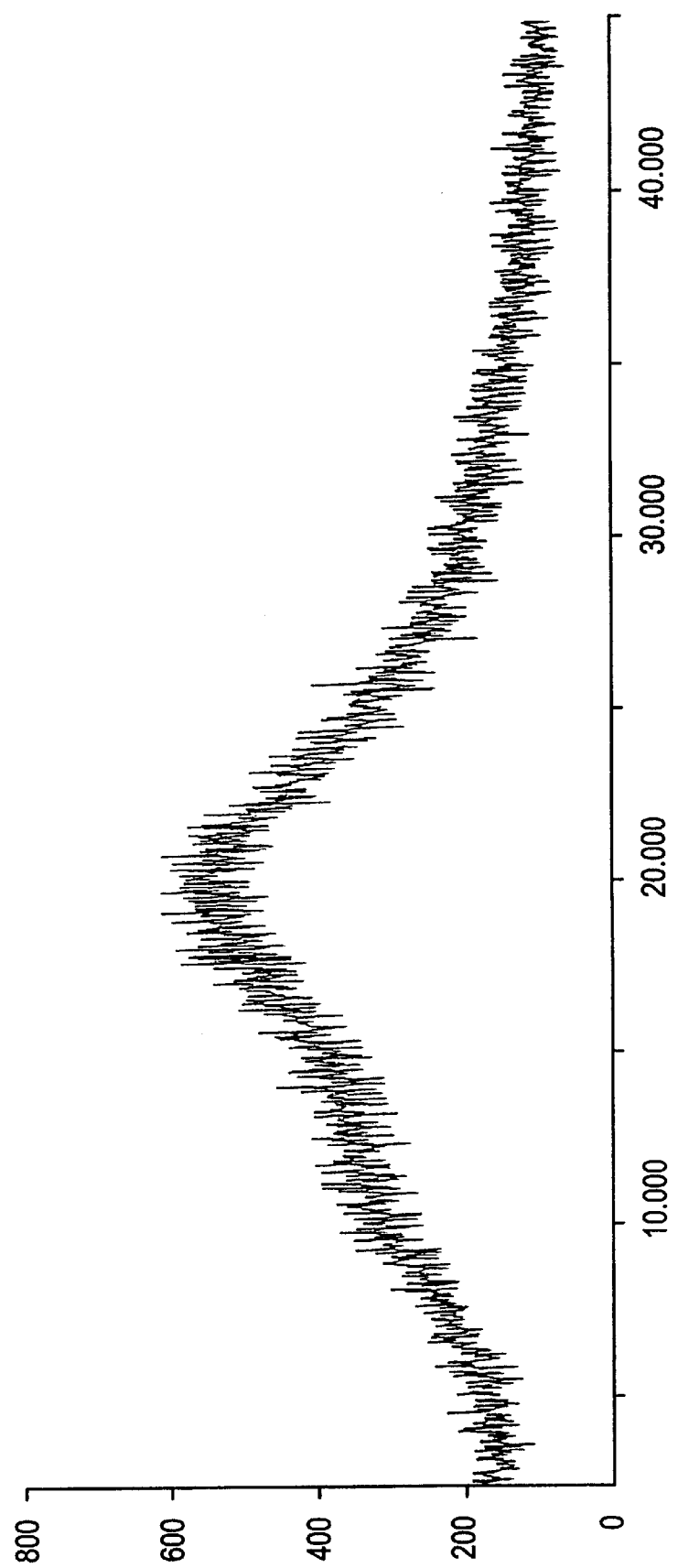
FIG. 6 is a characteristic X-ray powder diffraction pattern of Form VI.

Exotherm at 157.98° C.,

X-ray powder diffraction (2θ): No diffraction peaks due to its amorphous nature (FIG. 6)

Infrared absorption bands (cm$^{-1}$): 3065, 1629, 1490, 1377, 1273, 1244, 1109, 1042, 805, 740, 539, (FIG. 30)

According to yet another feature of the present invention, there is provided a novel polymorphic Form-VII of L-arginine salt of (2S) 3-[4-[2-(phenoxazin-10-yl)ethoxy]phenyl]-2-ethoxypropanoic acid, having the formula I which is characterized by the following data:

DSC: Endotherms at 176.63° C. (onset at 169.06° C.) and 184.09° C. (FIG. 19)

Figure 7:
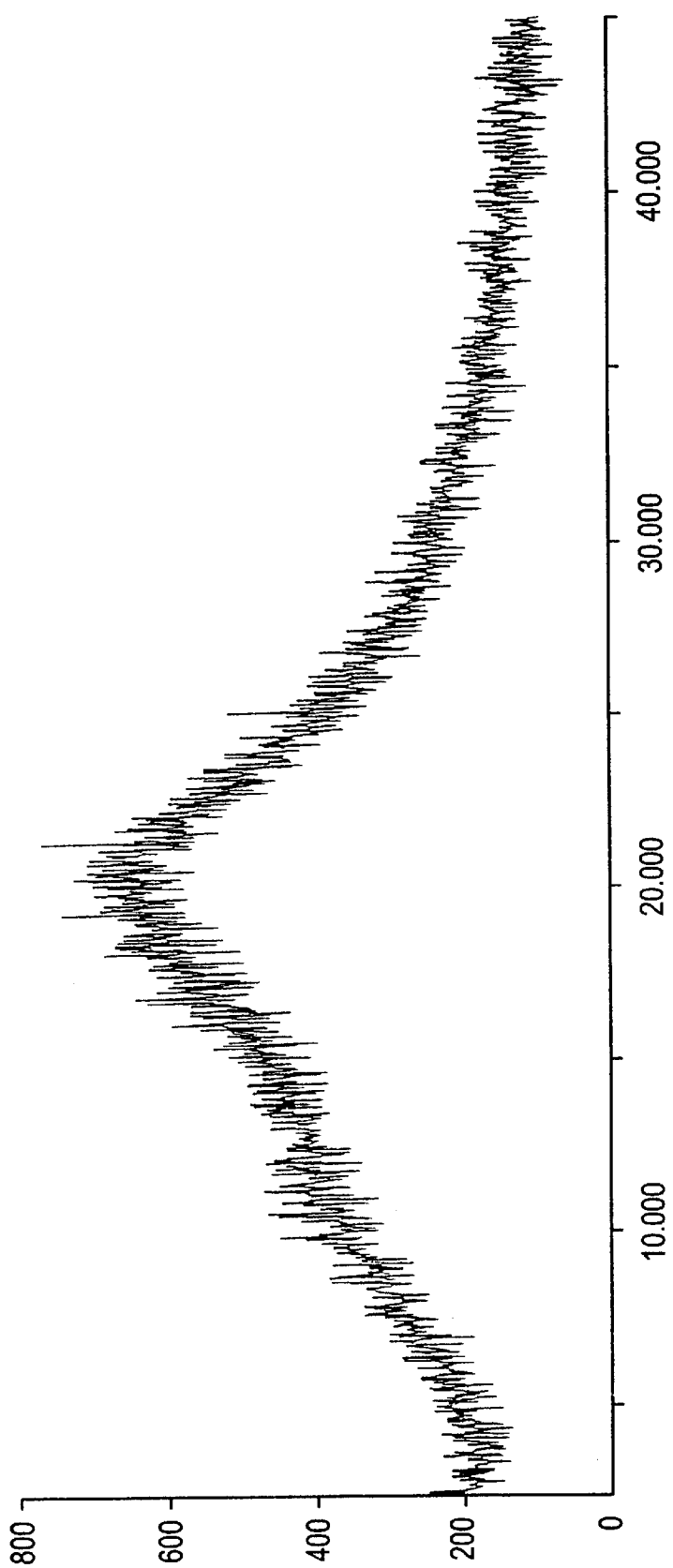
FIG. 7 is a characteristic X-ray powder diffraction pattern of Form VII.

Exotherm at 132.93° C.,

X-ray powder diffraction (2θ): No diffraction peaks due to its amorphous nature, (FIG. 7)

Infrared absorption bands (cm$^{-1}$): 3065, 1629, 1490, 1377, 1273, 1109, 1042, 740, 541, (FIG. 31)

According to yet another feature of the present invention, there is provided a novel polymorphic Form-VIII of L-arginine salt of (2S) 3-[4-[2-(phenoxazin-10-yl)ethoxy]phenyl]-2-ethoxypropanoic acid, having the formula I which is characterized by the following data:

DSC:. Endotherm at 178.12° C. (onset at 167.15° C.), (FIG. 20)

Small Endotherm at 152.72° C.

Exotherm at 158.27° C.

Figure 8:
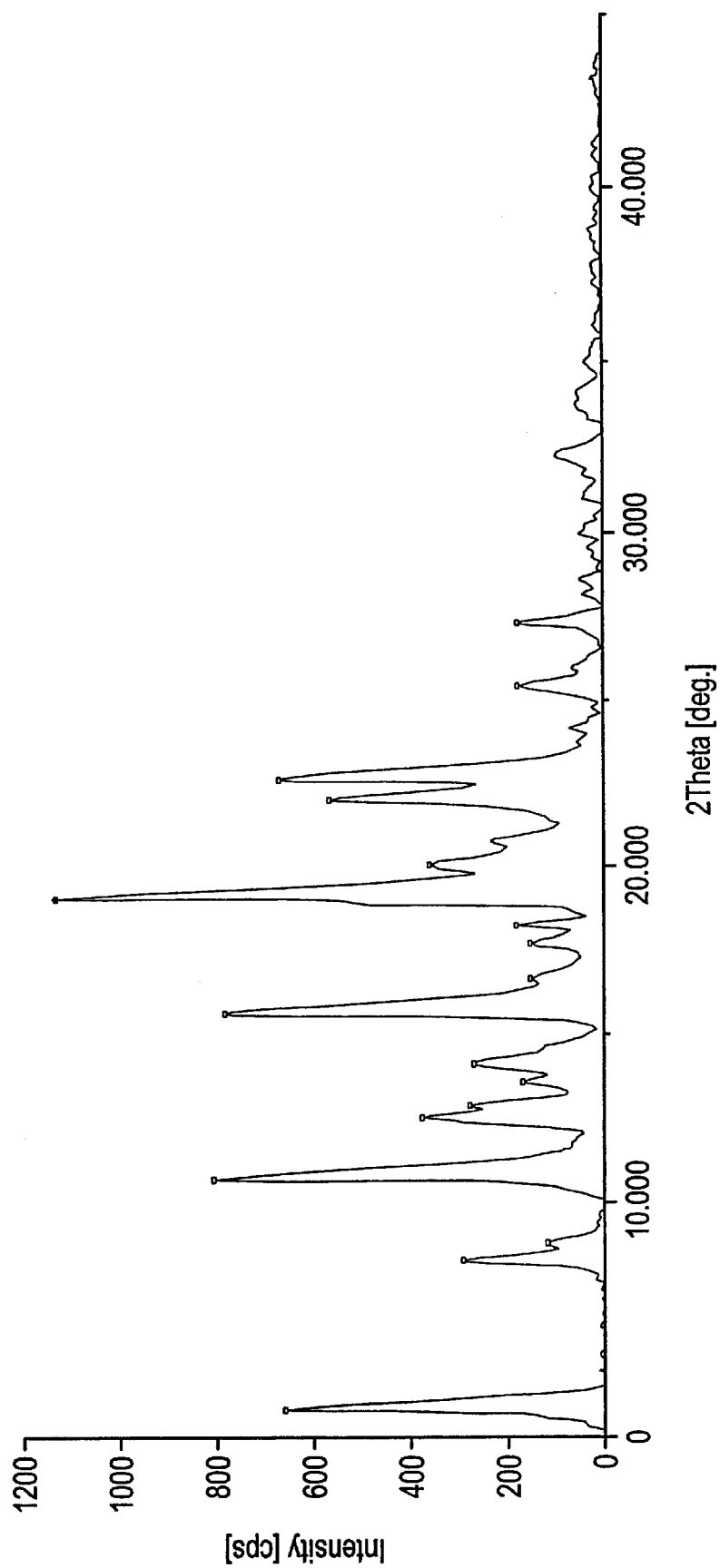
FIG. 8 is a characteristic X-ray powder diffraction pattern of Form VIII.

X-ray powder diffraction (2θ): 4.16, 11.02, 15.94, 19.50, 20.22, 22.22, 27.38, (FIG. 8)

Infrared absorption bands (cm$^{-1}$), 3151, 1629, 1490, 1378, 1272, 1244, 1104, 1041, 742, 549, (FIG. 32)

Figure 9:
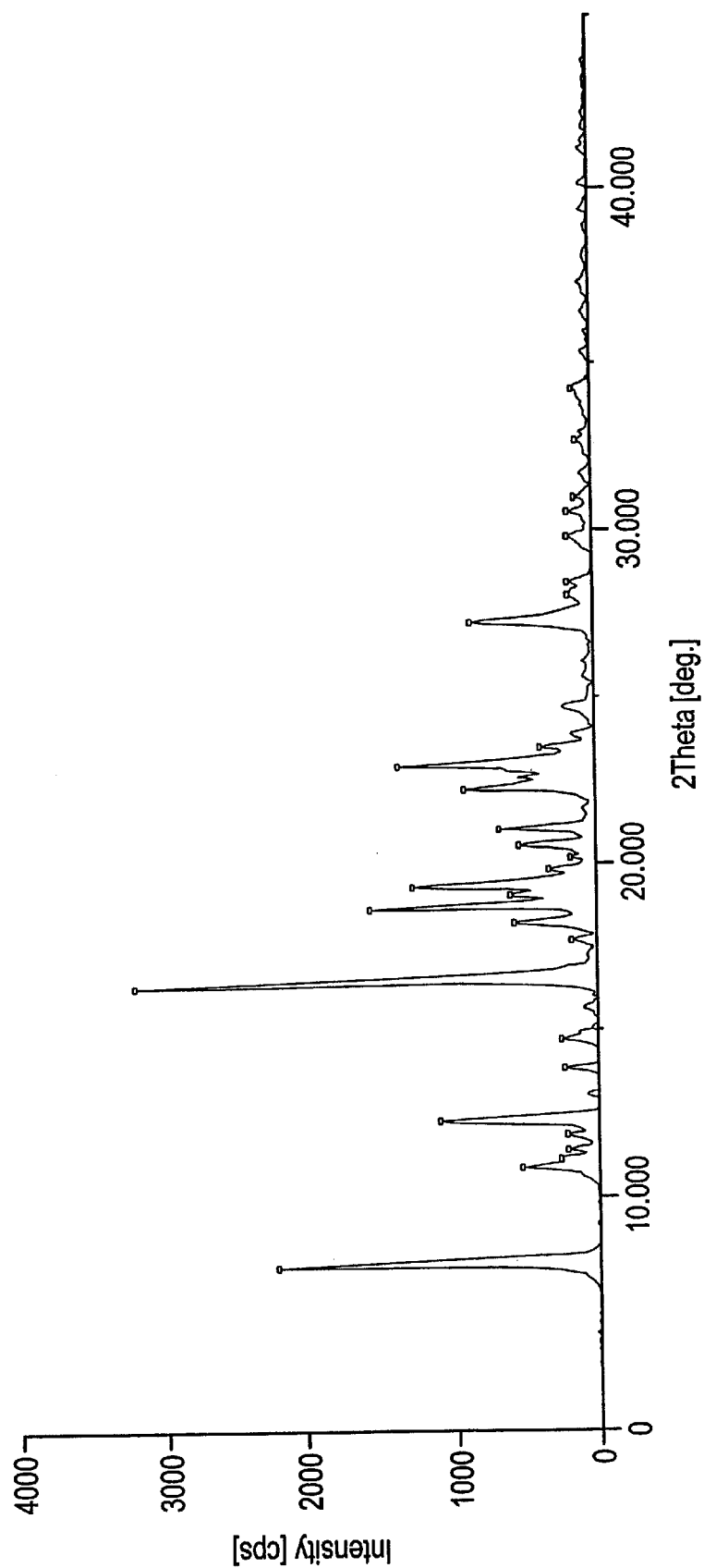
FIG. 9 is a characteristic X-ray powder diffraction pattern of Form IX.

According to yet another feature of the present invention, there is provided a novel polymorphic Form-IX of L-arginine salt of (2S) 3-[4-[2-(phenoxazin-10-yl)ethoxy]phenyl]-2-ethoxypropanoic acid, having the formula I which is characterized by the following data:

DSC: Endotherm at 176.67° C. (onset at 173.36° C.), (FIG. 21) X-ray powder diffraction (2θ): 8.20, 12.42, 16.66, 18.80, 19.44, 22.30, 23.08, 27.38, 28.48, 29.84, (FIG. 9)

Infrared absorption bands (cm$^{-1}$). 3066, 1588, 1489, 13716, 1273, 1243, 1110, 1043, 919, 805, 737, 543, (FIG. 33)

According to still another feature of the present invention, there is provided a novel polymorphic Form-X of L-arginine salt of (2S) 3-[4-[2-(phenoxazin-10-yl)ethoxy]phenyl]-2-ethoxypropanoic acid, having the formula I which is characterized by the following data:

DSC: Endotherm at 184.53° C., (FIG. 22)

Exotherm at, 162.67° C.

Figure 10:
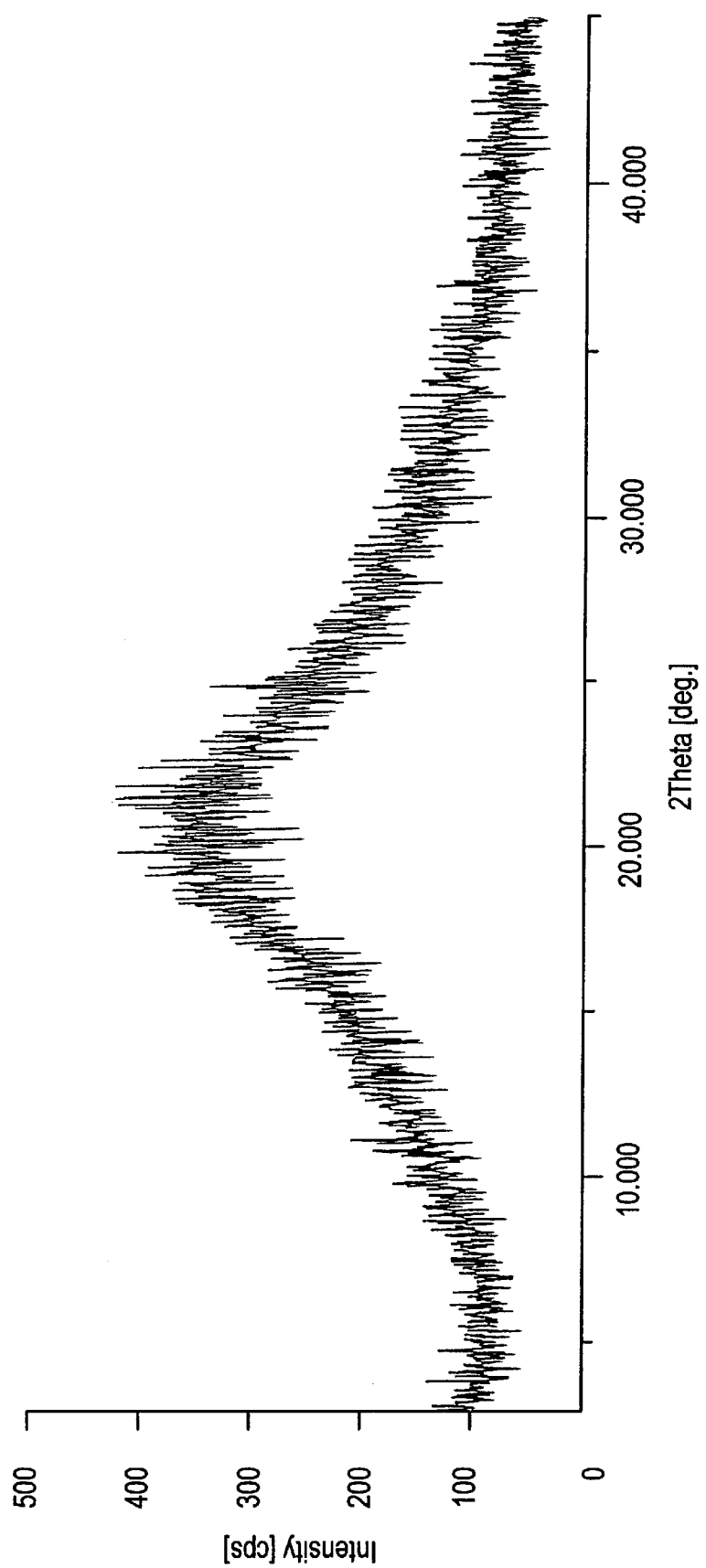
FIG. 10 is a characteristic X-ray powder diffraction pattern of Form X.

X-ray powder diffraction (2θ): No diffraction peaks due to its amorphous nature, (FIG. 10)

Infrared absorption bands (cm$^{-1}$): 3413, 1630, 1511, 1491, 1377, 1273, 1244, 1176, 1108, 741, (FIG. 34)

According to yet another feature of the present invention, there is provided a novel polymorphic Form-XI of L-arginine salt of (2S) 3-[4-[2-(phenoxazin-10-yl)ethoxy]phenyl]-2-ethoxypropanoic acid, having the formula I which is characterized by the following data:

DSC: Endotherm at 184.40° C. (onset at 177.67° C.), (FIG. 23)

Figure 11:
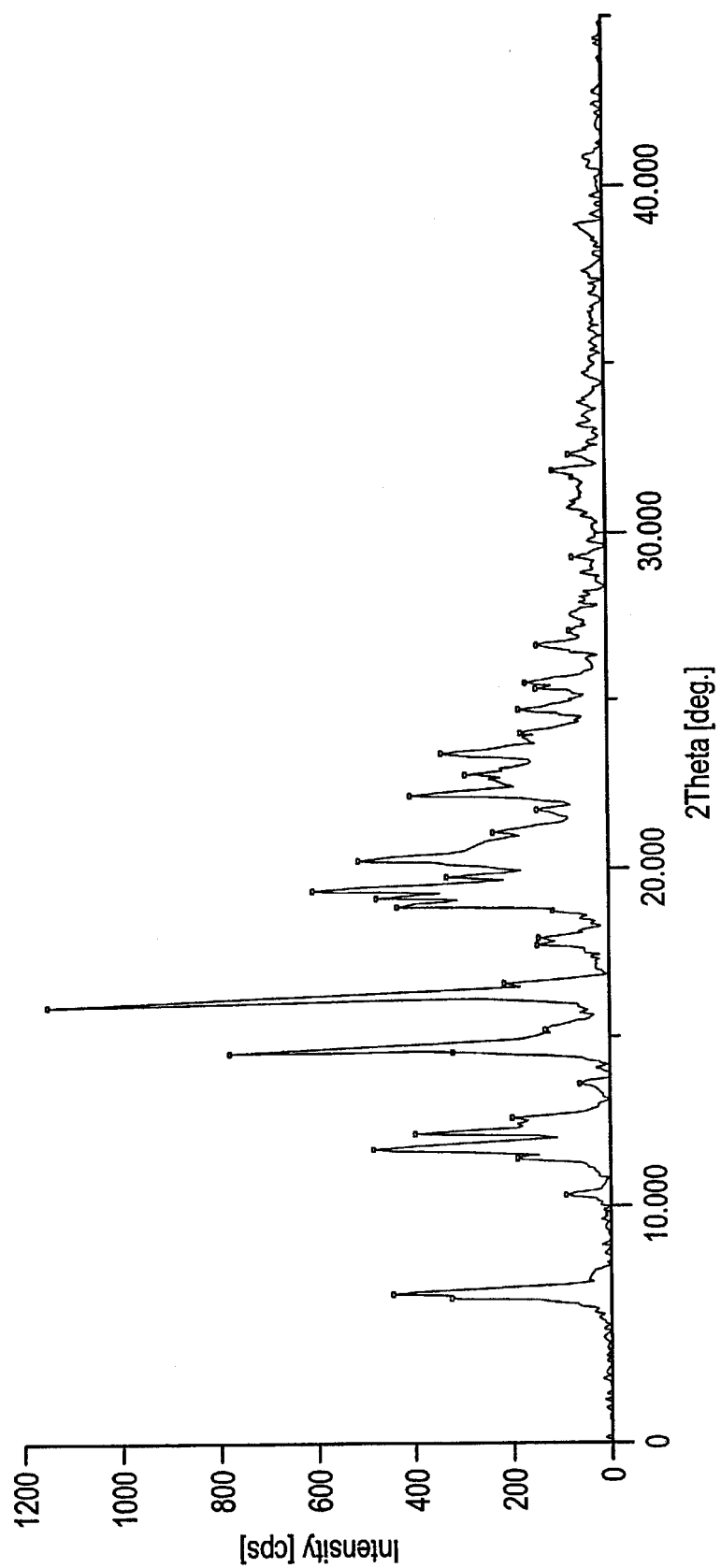
FIG. 11 is a characteristic X-ray powder diffraction pattern of Form XI.

X-ray powder diffraction (2θ): 7.38, 7.56, 11.90, 12.32, 14.80, 16.40, 19.58, 20.48, 22.34, 22.90, 23.54, (FIG. 11)

Infrared absorption bands (cm$^{-1}$): 3383, 2925, 1629, 1510, 1490, 1377, 1273, 1243, 1090, 1041, 739, 539, (FIG. 35)

According to yet another feature of the present invention, there is provided a novel mixture of polymorphic Forms I and X of L-arginine salt of (2S) 3-[4-[2-(phenoxazin-10-yl)ethoxy]phenyl]-2-ethoxypropanoic acid, having the formula I which is characterized by the following data:

DSC: Endotherms at 181.28° C., 185.31° C., (onset at 173.54° C.) (FIG. 24)

Figure 12:
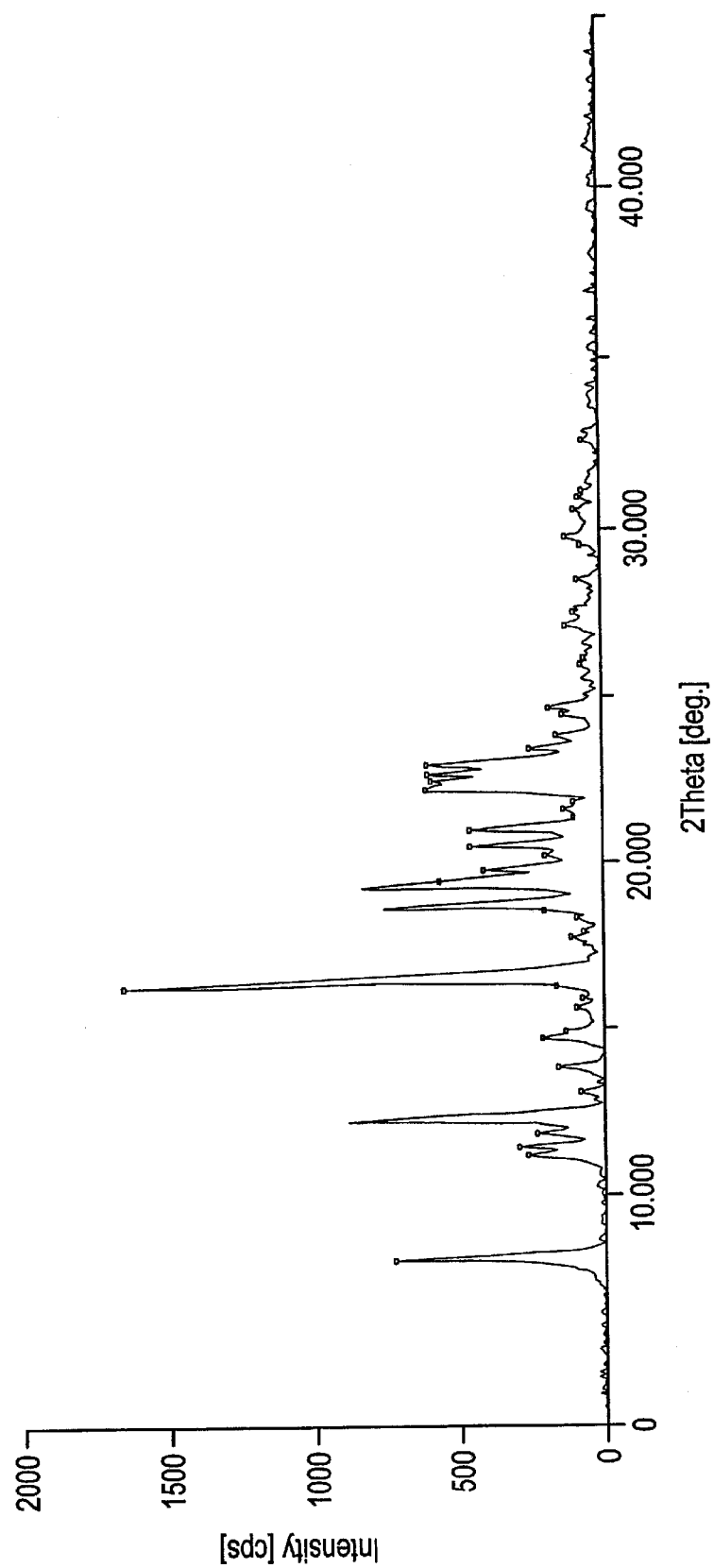
FIG. 12 is a characteristic X-ray powder diffraction pattern of polymorphic form mixture.

X-ray powder diffraction (2θ): 8.16, 12.40, 16.64, 18.78, 19.42, 22.34, 22.80, 23.08, 29.84, (FIG. 12)

Infrared absorption bands (cm$^{-1}$): 3247, 3066, 1708, 1587, 1510, 1489, 1375, 1273, 1244, 1178, 1111, 1043, 805, 737, 673, 543, (FIG. 36)

According to another feature of the present invention, there is provided a process for the preparation of novel polymorphic Form-I of L-arginine salt of (2S) 3-[4-[2-(phenoxazin-10-yl)ethoxy]phenyl]-2-ethoxypropanoic acid, of the formula I, having the characteristics described earlier, which comprises:

(i) synthesizing (2S) 3-[4-[2-(phenoxazin-10-yl)ethoxy]phenyl]-2-ethoxypropanoic acid, employing known methods and dissolving in an organic solvent, (ii) adding L-arginine dissolved in water slowly with constant stirring to the solution obtained in step (i), (iii) stirring the reaction mixture at a temperature of 40–80° C. for a period in the range of 18–30 h to obtain a white crystalline precipitate, (iv) filtering the white crystalline precipitate obtained in step (iii) above and (v) drying under vacuum at a temperature of 40–45° C. for a period in the range of 4–16 h to yield Form-I of L-arginine salt of (2S) 3-[4-[2-(phenoxazin-10-yl) ethoxy]phenyl]-2-ethoxypropanoic acid.

The temperature employed in the stirring step (iii) may be preferably 40–50° C.

According to another feature of the present invention, there is provided an alternate process for the preparation of novel polymorphic Form-I of L-arginine salt of (2S) 3-[4-[2-(phenoxazin-10-yl)ethoxy]phenyl]-2-ethoxypropanoic acid, of the formula I, having the characteristics described earlier, which comprises (i) synthesizing (2S) 3-[4-[2-(phenoxazin-10-yl)ethoxy]phenyl]-2-ethoxypropanoic acid, employing known methods and dissolving in an organic solvent, (ii) adding L-arginine dissolved in water slowly with constant stirring to the solution obtained in step (i), (iii) stirring the reaction mixture at room temperature for a period in the range of 90–100 h to obtain a white crystalline precipitate, (iv) filtering the white crystalline precipitate obtained in step (iii) above and (v) drying under vacuum at a temperature of 40–45° C. for a period in the range of 4–16 h to yield Form-I of L-arginine salt of (2S) 3-[4-[2-(phenoxazin-10-yl) ethoxy]phenyl]-2-ethoxypropanoic acid.

According to another feature of the present invention, there is provided a process for the preparation of novel polymorphic Form-II of L-arginine salt of (2S) 3-[4-[2-(phenoxazin-10-yl)ethoxy]phenyl]-2-ethoxypropanoic acid, of the formula I, having the characteristics described earlier, which comprises:

(i) synthesizing (2S) 3-[4-[2-(phenoxazin-10-yl)ethoxy] phenyl]-2-ethoxypropanoic acid, employing known methods and dissolving in acetone, (ii) adding L-arginine dissolved in water slowly with constant stirring to the solution obtained in step (i), (iii) stirring the reaction mixture at room temperature for a period in the range of 18–30 h to obtain a white crystalline precipitate (iv) filtering the white crystalline precipitate obtained in step (iii) above and (v) drying under vacuum at a temperature of 40–45° C. for a period in the range of 4–16 h to yield Form-II of L-arginine salt of (2S) 3-[4-[2-(phenoxazin-10-yl) ethoxy]phenyl]-2-ethoxypropanoic acid.

According to yet another feature of the present invention, there is provided a process for the preparation of novel polymorphic Form-III of L-arginine salt of (2S) 3-[4-[2-(phenoxazin-10-yl)ethoxy]phenyl]-2-ethoxypropanoic acid of the formula I, having the characteristics described earlier, which comprises:

(i) synthesizing (2S) 3-[4-[2-(phenoxazin-10-yl)ethoxy] phenyl]-2-ethoxypropanoic acid, employing known methods and dissolving in 1,4-dioxane, (ii) adding L-arginine dissolved in water slowly with constant stirring to the solution obtained in step (i), (iii) stirring the reaction mixture at room temperature for a period in the range of 18–30 h to obtain a white crystalline precipitate (iv) filtering the white crystalline precipitate obtained in step (iii) above and (v) drying under vacuum at a temperature of 40–45° C. for a period in the range of 4–16 h to yield Form-III of L-arginine salt of (2S) 3-[4-[2-(phenoxazin-10-yl) ethoxy]phenyl]-2-ethoxypropanoic acid.

According to yet another feature of the present invention, there is provided a process for the preparation of novel polymorphic Form-IV of L-arginine salt of (2S) 3-[4-[2-(phenoxazin-10-yl)ethoxy]phenyl]-2-ethoxypropanoic acid of the formula I, having the characteristics described earlier, which comprises:

(i) synthesizing (2S) 3-[4-[2-(phenoxazin-10-yl)ethoxy] phenyl]-2-ethoxypropanoic acid, employing known methods and dissolving in dimethyl sulfoxide, (ii) adding L-arginine dissolved in water slowly with constant stirring to the solution obtained in step (i), (iii) stirring the reaction mixture at room temperature for a period in the range of 18–30 h to obtain a white crystalline precipitate (iv) filtering the white crystalline precipitate obtained in step (iii) above and (v) drying under vacuum at a temperature of 40–45° C. for a period in the range of 4–16 h to yield Form-IV of L-arginine salt of (2S) 3-[4-[2-(phenoxazin-10-yl) ethoxy]phenyl]-2-ethoxypropanoic acid.

According to another feature of the present invention, there is provided a process for the preparation of novel polymorphic Form-V of L-arginine salt of (2S) 3-[4-[2-(phenoxazin-10-yl)ethoxy]phenyl]-2-ethoxypropanoic acid of the formula I, having the characteristics described earlier, which comprises:

(i) synthesizing (2S) 3-[4-[2-(phenoxazin-10-yl)ethoxy] phenyl]-2-ethoxypropanoic acid, employing known methods and dissolving in dimethyl formamide, (ii) adding L-arginine dissolved in water slowly with constant stirring in the solution obtained instep (i), (iii) stirring the reaction mixture at room temperature for a period in the range of 18–30 h to obtain a white crystalline precipitate, (iv) filtering the white crystalline precipitate obtained in step (iii) above and (v) drying under vacuum at a temperature of 40–45° C. for a period in the range of 4–16 h to yield Form-V of L-arginine salt of (2S) 3-[4-[2-(phenoxazin-10-yl) ethoxy]phenyl]-2-ethoxypropanoic acid.

According to another feature of the present invention, there is provided a process for the preparation of novel polymorphic Form-VI of L-arginine salt of (2S) 3-[4-[2-(phenoxazin-10-yl)ethoxy]phenyl]-2-ethoxypropanoic acid of the formula I, having the characteristics described earlier, which comprises:

(i) dissolving any of the polymorphic Forms I–V of L-arginine salt of (2S) 3-[4-[2-(phenoxazin-10-yl) ethoxy]phenyl]-2-ethoxypropanoic acid in water and (ii) freeze drying the resulting solution to yield an amorphous white powder of Form-VI of L-arginine salt of (2S) 3-[4-[2-(phenoxazin-10-yl)ethoxy]phenyl]-2-ethoxypropanoic acid.

According to another feature of the present invention, there is provided a process for the preparation of novel polymorphic Form-VII of L-arginine salt of (2S) 3-[4-[2-(phenoxazin-10-yl)ethoxy]phenyl]-2-ethoxypropanoic acid of the formula I, having the characteristics described earlier, which comprises:

(i) dissolving any of the polymorphic Forms I–V of L-arginine salt of (2S) 3-[4-[2-(phenoxazin-10-yl) ethoxy]phenyl]-2-ethoxypropanoic acid in methanol and (ii) evaporating the resulting solution under vacuum to obtain an amorphous white powder of Form-VII of L-arginine salt of (2S) 3-[4-[2-(phenoxazin-10-yl) ethoxy]phenyl]-2-ethoxypropanoic acid.

According to another feature of the present invention, there is provided a process for the preparation of novel polymorphic Form-VIII of L-arginine salt of (2S) 3-[4-[2-(phenoxazin-10-yl)ethoxy]phenyl]-2-ethoxypropanoic acid, of the formula I, having the characteristics described earlier, which comprises:

(i) synthesizing (2S) 3-[4-[2-(phenoxazin-10-yl)ethoxy] phenyl]-2-ethoxypropanoic acid, employing known methods and dissolving in an organic solvent, (ii) adding L-arginine dissolved in water slowly with constant stirring in the solution obtained in step (i), (iii) stirring the reaction mixture at a temperature of 40–80° C. for a period in the range of 18–30 h to obtain a white crystalline precipitate, (iv) filtering the white crystalline precipitate obtained in step (iii) above and (v) drying under vacuum at a temperature of 40–45° C. for a period in the range of 4–16 h to yield Form-I of L-arginine salt of (2S) 3-[4-[2-(phenoxazin-10-yl) ethoxy]phenyl]-2-ethoxypropanoic acid, (vi) refluxing the Form-I of L-arginine salt of (2S) 3-[4-[2-(phenoxazin-10-yl)ethoxy]phenyl]-2- ethoxypropanoic acid, obtained above in step (v) in 1,4-dioxane for a period in the range of 8–16 h and (vii) filtering and drying under vacuum at a temperature of 40–45° C. for a period in the range of 4–16 h to yield Form-VIII of L-arginine salt of (2S) 3-[4-[2-(phenoxazin-10-yl)ethoxy]phenyl]-2-ethoxypropanoic acid.

According to another feature of the present invention, there is provided a process for the preparation of novel polymorphic Form-IX of L-arginine salt of (2S) 3-[4-[2-(phenoxazin-10-yl)ethoxy]phenyl]-2-ethoxypropanoic acid, of the formula I, having the characteristics described earlier, which comprises:

(i) synthesizing (2S) 3-[4-[2-(phenoxazin-10-yl)ethoxy] phenyl]-2-ethoxypropanoic acid, employing known methods and dissolving in an organic solvent, (ii) adding L-arginine dissolved in water slowly with constant stirring in the solution obtained in step (i), (iii) stirring the reaction mixture at a temperature of 40–80° C. for a period in the range of 18–30 h to obtain a white crystalline precipitate, (iv) filtering the white crystalline precipitate obtained in step (iii) above and (v) drying under vacuum at a temperature of 40–45° C. for a period in the range of 4–16 h to yield Form-I of L-arginine salt of (2S) 3-[4-[2-(phenoxazin-10-yl) ethoxy]phenyl]-2-ethoxypropanoic acid, (vi) refluxing the Form-I of L-arginine salt of (2S) 3-[4-[2-(phenoxazin-10-yl)ethoxy]phenyl]-2-ethoxypropanoic acid, obtained above in step (v) in 1,4-dioxane for a period in the range of 8–16 h, (vii) filtering and drying under vacuum at a temperature of 40–45° C. for a period in the range of 4–16 h to yield Form-VIII of L-arginine salt of (2S) 3-[4-[2-(phenoxazin-10-yl)ethoxy]phenyl]-2-ethoxypropanoic acid, (viii) refluxing the Form-VIII of L-arginine salt of (2S) 3-[4-[2-(phenoxazin-10-yl)ethoxy]phenyl]-2-ethoxypropanoic acid, obtained in step (vii) above in isopropyl alcohol for a period in the range of 8–16 h and (ix) filtering and drying under vacuum at a temperature of 40–45° C. for a period in the range of 4–16 h to yield Form-IX of L-arginine salt of (2S) 3-[4-[2-(phenoxazin-10-yl)ethoxy]phenyl]-2-ethoxypropanoic acid.

According to another feature of the present invention, there is provided a process for the preparation of novel polymorphic Form-X of L-arginine salt of (2S) 3-[4-[2-(phenoxazin-10-yl)ethoxy]phenyl]-2-ethoxypropanoic acid, of the formula I, having the characteristics described earlier, which comprises:

(i) synthesizing (2S) 3-[4-[2-(phenoxazin-10-yl)ethoxy] phenyl]-2-ethoxypropanoic acid, employing known methods and dissolving in an organic solvent, (ii) adding L-arginine dissolved in water slowly with constant stirring to the solution obtained in step (i), (iii) stirring the reaction mixture at a temperature of 40–80° C. for a period in the range of 18–30 h to obtain a white crystalline precipitate, (iv) filtering the white crystalline precipitate obtained in step (iii) above and (v) drying under vacuum at a temperature of 40–45° C. for a period in the range of 4–16 h to yield Form-I of L-arginine salt of (2S) 3-[4-[2-(phenoxazin-10-yl) ethoxy]phenyl]-2-ethoxypropanoic acid and (vi) heating the polymorphic Form-I obtained in step (v) to 185° C. and cooling it to room temperature to yeild Form-X of L-arginine salt of (2S) 3-[4-[2-(phenoxazin-10-yl)ethoxy]phenyl]-2-ethoxypropanoic acid.

According to another feature of the present invention, there is provided a process for the preparation of novel polymorphic Form-XI of L-arginine salt of (2S) 3-[4-[2-(phenoxazin-10-yl)ethoxy]phenyl]-2-ethoxypropanoic acid, of the formula I, having the characteristics described earlier, which comprises:

(i) synthesizing (2S) 3-[4-[2-(phenoxazin-10-yl)ethoxy] phenyl]-2-ethoxypropanoic acid, employing known methods and dissolving in an organic solvent, (ii) adding L-arginine dissolved in water slowly with constant stirring to the solution obtained in step (i), (iii) stirring the reaction mixture at a temperature of 40–80° C. for a period in the range of 18–30 h to obtain a white crystalline precipitate, (iv) filtering the white crystalline precipitate obtained in step (iii) above and (v) drying under vacuum at a temperature of 40–45° C. for a period in the range of 4–16 h to yield Form-I of L-arginine salt of (2S) 3-[4-[2-(phenoxazin-10-yl) ethoxy]phenyl]-2-ethoxypropanoic acid, (vi) heating the polymorphic Form-I obtained in step (v) to 185° C. and cooling it to room temperature to yeild Form-X of L-arginine salt of (2S) 3-[4-[2-(phenoxazin-10-yl)ethoxy]phenyl]-2-ethoxypropanoic acid and (vii) heating the polymorphic Form-X obtained in step (vi) to 175° C. and cooling it to room temperature to yield Form-XI of L-arginine salt of (2S) 3-[4-[2-(phenoxazin-10-yl)ethoxy]phenyl]-2-ethoxypropanoic acid.

According to another feature of the present invention there is provided a process for the preparation of novel mixture of polymorphic Form of I and X of L-arginine salt of (2S) 3-[4-[2-(phenoxazin-10-yl)ethoxy]phenyl]-2-ethoxypropanoic acid, of the formula I, described earlier, which comprises:

(i) synthesizing (2S) 3-[4-[2-(phenoxazin-10-yl)ethoxy] phenyl]-2-ethoxypropanoic acid, employing known methods and dissolving in an organic solvent, (ii) adding L-arginine dissolved in water slowly with constant stirring in the solution obtained in step (i), (iii) stirring the reaction mixture at room temperature for a period in the range of 18–30 h to separate white crystalline powder, (iv) filtering the white crystalline powder obtained in step (iii) and (v) drying under vacuum at a temperature of 40–45° C. for a period in the range of 4–16 h to yield mixture of polymorphic Form of I and X of L-arginine salt of (2S) 3-[4-[2-(phenoxazin-10-yl)ethoxy]phenyl]-2-ethoxypropanoic acid.

According to another feature of the present invention, there is provided an alternate process for the preparation of novel polymorphic Form-I of L-arginine salt of (2S) 3-[4-[2-(phenoxazin-10-yl)ethoxy]phenyl]-2-ethoxypropanoic acid, of the formula I, having the characteristics described earlier, which comprises (i) suspending any of the polymorphic Form II to XI or the mixture of polymorphic Form I and X of L-arginine salt of (2S) 3-[4-[2-(phenoxazin-10-yl)ethoxy]phenyl]-2- ethoxypropanoic acid in isopropyl alcohol and stirring in dark conditions at room temperature for a period of 35–50 h, (ii) filtering and washing with isopropyl alcohol and (iii) drying under vacuum at a temperature of 40–45° C. for a period in the range of 4–16 h to yield polymorphic Form of I of L-arginine salt of (2S) 3-[4-[2-(phenoxazin-10-yl)ethoxy]phenyl]-2-ethoxypropanoic acid, The organic solvents are selected from acetonitrile, ethanol, methanol and, isopropanol.

The present invention also envisages a pharmaceutical composition comprising a polymorphic Forms I to XI of L-arginine salt of (2S) 3-[4-[2-(phenoxazin-10-yl)ethoxy] phenyl]-2-ethoxypropanoic acid, of the formula (1) or the mixture of polymorphic Form of I and X and a pharmaceutically acceptable carrier.

The present invention also envisages a pharmaceutical composition comprising a mixture of any of polymorphic Forms I to XI of L-arginine salt of (2S) 3-[4-[2-(phenoxazin-10-yl)ethoxy]phenyl]-2-ethoxypropanoic acid, of the formula (I) and a pharmaceutically acceptable carrier.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 25%, preferably 1 to 15% by weight of active ingredient, the remainder of the composition being pharmaceutically acceptable carriers, diluents or solvents.

The polymorphic forms of the formula (I) as defined above are clinically administered to mammals, including man, via either oral, nasal, pulmonary, transdermal or parenteral, rectal, depot, subcutaneous, intravenous, intraurethral, intramuscular, intranasal, ophthalmic solution or an ointment. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active ingredient will be present in such pharmaceutical compositions in the amounts sufficient to provide the desired dosage in the range as described above. Thus, for oral administration, the polymorphic form can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the polymorphic form can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. Aqueous solutions with the active ingredient dissolved in polyhydroxylated castor oil may also be used for injectable solutions. The injectable solutions prepared in this manner can then be administered intravenously, intraperitoneally, subcutaneously, or intramuscularly, with intramuscular administration being preferred in humans.

For nasal administration, the preparation may contain the polymorphic forms of the present invention dissolved or suspended in a liquid carrier, in particular an aqueous carrier, for aerosol application. The carrier may contain additives such as solubilizing agents, such as propylene glycol, surfactants, absorption enhancers such as lecithin (phosphatidylcholine) or cyclodextrin or preservatives such as parabene3.

Tablets, dragees or capsules having talc and/or a carbohydrate carried binder or the like are particularly suitable for any oral application, Preferably, carriers for tablets, dragees or capsules include lactose, corn starch and/or potato starch. A syrup or elixir can be used in cases where a sweetened vehicle can be employed.

A typical tablet production method is exemplified below:

Tablet Production Example

| a) | 1) Active ingredient | 30 g |
|---|---|---|
| | 2) Lactose | 95 g |
| | 3) Corn starch | 30 g |
| | 4) Carboxymethyl cellulose | 44 g |
| | 5) Magnesium stearate | 1 g |
| | | 200 g for 1000 tablets |

The ingredients 1 to 3 are uniformly blended with water and granulated after drying under reduced pressure. The ingredient 4 and 5 are mixed well with the granules and compressed by a tabletting machine to prepare 1000 tablets each containing 30 mg of active ingredient.

| b) | 1) Active ingredient | 30 g |
|---|---|---|
| | 2) Calcium phosphate | 90 g |
| | 3) Lactose | 40 g |
| | 4) Corn starch | 35 g |
| | 5) Polyvinyl pyrrolidone | 3.5 g |
| | 6) Magnesium stearate | 1.5 g |
| | | 200 g for 1000 tablets |

The ingredients 1–4 are uniformly moistened with an aqueous solution of 5 and granulated after drying under reduced pressure. Ingredient 6 is added and granules are compressed by a tabletting machine to prepare 1000 tablets containing 30 mg of ingredient 1.

EXAMPLES

Synthesis of (2S) 3-[4-[2-(Phenoxazin-10-yl) ethoxy]phenyl]-2-ethoxypropanoic Acid, is Described in our WO Publication No. WO 99/ 19313 and Copending PCT Application No. PCT/ IB99/00683

The present invention is described in detail in the examples given below which are provided by way of illustration only and therefore should not be construed to limit the scope of the invention.

Examples 1–4

Illustrates the Process for the Preparation of the Polymorphic Form-1 of L-arginine Salt of (2S) 3-[4-[2-(Phenoxazin-10-yl)ethoxy]phenyl]-2-ethoxypropanoic Acid

Example-1

To a solution of (2S) 3-[4-[2-(phenoxazin-10-yl)ethoxy]phenyl]-2-ethoxypropanoic acid (1 g) in ethanol (25 ml) was added L-arginine dissolved in water (1.2 ml) slowly with constant stirring. The reaction mixture was stirred at 40–50° C. for 24 h. The white crystalline precipitate formed was separated and dried under vacuum at 40–45° C. for 4 h to yield Form-I of L-arginine salt of (2S) 3-[4-[2-(phenoxazin-10-yl)ethoxy]phenyl]-2-ethoxypropanoic acid (11.5 g) which has the characteristics given earlier.

Example-2

To a solution of (2S) 3-[4-[2-(phenoxazin-10-yl)ethoxy]phenyl]-2-ethoxypropanoic acid (1 g) in isopropyl alcohol (25 ml) was added L-arginine dissolved in water (1.2 ml) slowly with constant stirring. The reaction mixture was stirred at 40–50° C. for 24 h. The white crystalline precipitate formed was separated and dried under vacuum at 40–45° C. for 4 h to yield Form-I of L-arginine salt of (2S) 3-[4-[2-(phenoxazin-10-yl)ethoxy]phenyl]-2-ethoxypropanoic acid (1.27 g) which has the characteristics given earlier.

Example-3

To a solution of (2S) 3-[4-[2-(phenoxazin-10-yl)ethoxy]phenyl]-2-ethoxypropanoic acid (1 g) in acetonitrile (25 ml) was added L-arginine dissolved in water (1.2 ml) slowly with constant stirring, The reaction mixture was stirred at 40–50° C. for 24 h. The white crystalline precipitate formed was separated and dried under vacuum at 40–45° C. for 4 h to yield Form-I L-arginine salt of (2S) 3-[4-[2-(phenoxazin-10-yl)ethoxy]phenyl]-2-ethoxypropanoic acid (1.24 g) which has the characteristics given earlier.

Example-4

To a solution of (2S) 3-[4-[2-(phenoxazin-10-yl)ethoxy]phenyl]-2-ethoxypropanoic acid (1 g) in methanol (15 ml) was added L-arginine dissolved in water (1.2 ml) slowly with constant stirring. The reaction mixture was stirred at 40–50° C. for 24 h The white crystalline precipitate formed was separated and dried under vacuum at 40–45° C. for 4 h to yield Form-I L-arginine salt of (2S) 3-[4-[2-(phenoxazin-10-yl)ethoxy]phenyl]-2-ethoxypropanoic acid (1.05 g) which has the characteristics given earlier.

Example-5

To a solution of (2S) 3-[4-[2-(phenoxazin-10-yl)ethoxy]phenyl]-2-ethoxypropanoic acid (1 g) in isopropyl alcohol (25 ml) was added L-arginine dissolved in water (1.2 ml) slowly with constant stirring. The reaction mixture was stirred at room temperature for 90–100 h. The white crystalline precipitate formed was separated and dried under vacuum at 40–45° C. for 4 h to yield Form-I L-arginine salt of (2S) 3-[4-[2-(phenoxazin-10-yl)ethoxy]phenyl]-2-ethoxypropanoic acid (1.05 g) which has the characteristics given earlier.

Example 6

Process for the Preparation of the Polymorphic Form-II of L-arginine Salt of (2S) 3-[4-[2-(Phenoxazin-10-yl)ethoxy]phenyl]-2-ethoxypropanoic Acid, To a solution of (2S) 3-[4-[2-(phenoxazin-10-yl)ethoxy]phenyl]-2-ethoxypropanoic acid (1 g) in acetone (25 ml) was added L-arginine dissolved in water (1.2 ml) slowly with constant stirring. The reaction mixture was stirred at room temperature for 24 h. The white crystalline precipitate formed was separated and dried under vacuum at 40–45° C. for 4 h to yield Form-II of L-arginine salt of (2S) 3-[4-[2-(phenoxazin-10-yl)ethoxy]phenyl]-2-ethoxypropanoic acid (1.29 g) which has the characteristics given earlier.

Example 7

Process for the Preparation of the Polymorphic Form-III of L-arginine Salt of (2S) 3-[4-[2-(Phenoxazin-10-yl)ethoxy]phenyl]-2-ethoxypropanoic Acid To a solution of (2S) 3-[4-[2-(phenoxazin-10-yl)ethoxy]phenyl]-2-ethoxypropanoic acid (1 g) in 1,4-dioxane (25 ml) was added L-arginine dissolved in water (1.2 ml) slowly with constant stirring. The reaction mixture was stirred at room temperature for 24 h. The white crystalline precipitate formed was separated and dried under vacuum at 40–45° C. for 4 h to yield Form-III of L-arginine salt of (2S) 3-[4-[2-(phenoxazin-10-yl)ethoxy]phenyl]-2-ethoxypropanoic acid (1.25 g) which has the characteristics given earlier.

Example 8

Process for the Preparation of the Polymorphic Form-IV of L-arginine Salt of (2S) 3-[4-[2-(Phenoxazin-10-yl)ethoxy]phenyl]-2-ethoxypropanoic Acid To a solution of (2S) 3-[4-[2-(phenoxazin-10-yl)ethoxy]phenyl]-2-ethoxypropanoic acid (1 g) in DMSO (20 mul) was added L-arginine dissolved in water (1.2 ml) slowly with constant stirring. The reaction mixture was stirred at room temperature for 24 h. The white crystalline precipitate formed was separated and dried under vacuum at 40–45° C. for 4 h to yield Form-III of L-arginine salt of (2S) 3-[4-[2-(phenoxazin-10-yl)ethoxy]phenyl]-2-ethoxypropanoic acid (1.3 g) which has the characteristics given earlier.

Example 9

Process for the Preparation of the Polymorphic Form-V of L-arginine Salt of (2S) 3-[4-[2-(Phenoxazin-10-yl)ethoxy]phenyl]-2-ethoxypropanoic Acid To a solution of (2S) 3-[4-[2-(phenoxazin-10-yl)ethoxy]phenyl]-2-ethoxypropanoic acid (1 g) in DMF (25 ml) was added L-arginine dissolved in water (1.2 ml) slowly with constant stirring The reaction mixture was stirred at room temperature for 24 h. The white crystalline precipitate formed was separated and dried under vacuum at 40–45° C. for 4 h to yield Form-V of L-arginine salt of (2S) 3-[4-[2-(phenoxazin-10-yl)ethoxy]phenyl]-2-ethoxypropanoic acid (1.17 g) which has the characteristics given earlier.

Example 10

Process for the Preparation of the Polymorphic Form-VI of L-arginine Salt of (2S) 3-[4-[2-(Phenoxazin-10-yl)ethoxy]phenyl]-2-ethoxypropanoic Acid Polymorphic Form-I of L-arginine salt of (2S) 3-[4-[2-phenoxazin-10-yl)ethoxy]phenyl]-2-ethoxypropanoic acid (1 g), obtained by the process described in Example-2 above was dissolved in water (10 ml) and freeze dried to yield Form-VI of L-arginine salt of (2S) 3-[4-[2-(phenoxazin-10-yl)ethoxy]phenyl]-2-ethoxypropanoic acid, as an amorphous white powder (0.95 g) which has the characteristics given earlier.

Example 11

Process for the Preparation of the Polymorphic Form-VII of L-arginine Salt of (2S) 3-[4-[2-(Phenoxazin-10-yl)ethoxy]phenyl]-2-ethoxypropanoic Acid Polymorphic Form- of L-arginine salt of (2S) 3-[4-[2-(phenoxazin-10-yl)ethoxy]phenyl]-2-ethoxypropanoic acid (1 g), obtained by the process described in Example-3 above was dissolved in methanol (25 ml) and evaporated under vacuum to yield Form-VII of L-arginine salt of (2S) 3-[4-[2-(phenoxazin-10-yl)ethoxy]phenyl]-2-ethoxypropanoic acid, as an amorphous white powder (0.9 g) which has the characteristics given earlier.

Example 12

Process for the Preparation of the Polymorphic form-VIII of L-arginine Salt of (2S) 3-[4-[2-(Phenoxazin-10-yl)ethoxy]phenyl]-2-ethoxypropanoic Acid Polymorphic Form-I of L-arginine salt of (2S) 3-[4-[2-(phenoxazin-10-yl)ethoxy]phenyl]-2-ethoxypropanoic acid (1 g), obtained by the process described in Example-2 above was refluxed in 1,4-dioxane (10 ml), filtered and dried under vacuum to yield Form-VIII of L-arginine salt of (2S) 3-[4-[2-(phenoxazin-10-yl)ethoxy]phenyl]-2-ethoxypropanoic acid which has the characteristics given earlier.

Example 13

Process for the Preparation of the Polymorphic Form-IX of L-arginine Salt of (2S) 3-[4-[2-(Phenoxazin-10-yl)ethoxy]phenyl]-2-ethoxypropanoic Acid Polymorphic Form-VIII L-arginine salt of (2S) 3-[4-[2-(phenoxazin-10-yl)ethoxy]phenyl]-2-ethoxypropanoic acid (1 g), obtained by the process described in Example-12 was refluxed in isopropanol (10 ml), filtered and dried under vacuum to yield Form-IX of L-arginine salt of (2S) 3-[4-[2-(phenoxazin-10-yl)ethoxy]phenyl]-2-ethoxypropanoic acid which has the characteristics given earlier.

Example 14

Process for the Preparation of the Polymorphic Form-X of L-arginine Salt of (2S) 3-[4-[2-(Phenoxazin-10-yl)ethoxy]phenyl]-2-ethoxypropanoic Acid Polymorphic Form-I of L-arginine salt of (2S) 3-[4-[2-(phenoxazin-10-yl)ethoxy]phenyl]-2-ethoxypropanoic acid obtained by any of the process described in Examples-1–5 was heated to 185° C. and cooled it to room temperature to yield Form-X of L-arginine salt of (2S) 3-[4-[2-(phenoxazin-10-yl)ethoxy]phenyl]-2-ethoxypropanoic acid which has the characteristics given earlier.

Example 15

Process for the Preparation of the Polymorphic Form-XI of L-arginine Salt of (2S) 3-[4-[2-(Phenoxazin-10-yl)ethoxy]phenyl]-2-ethoxypropanoic Acid Polymorphic Form-X of L-arginine salt of (2S) 3-[4-[2-(phenoxazin-10-yl)ethoxy]phenyl]-2-ethoxypropanoic acid obtained by the process described in Example 14 was heated to 175° C. and cooled it to room temperature to yield Form-XI of L-arginine salt of (2S) 3-[4-[2-(phenoxazin-10-yl)ethoxy]phenyl]-2-ethoxypropanoic acid which has the characteristics given earlier.

Example 16

Process for the Preparation of Mixture of Polymorphic Forms I and X of L-arginine Salt of (2S) 3-[4-[2-(Phenoxazin-10-yl)ethoxy]phenyl]-2-ethoxypropanoic Acid To a solution of (2S) 3-[4-[2-(phenoxazin-10-yl)ethoxy]phenyl]-2-ethoxypropanoic acid (1 g) in isopropyl alcohol (25 ml) was added L-arginine dissolved in water (1.2 ml) slowly with constant stirring. The reaction mixture was stirred at room temperature for 24 h. The white crystalline powder formed was separated and dried under vacuum at 40–45° C. for 4 h to yield a mixture of polymorphic Forms I and X of L-arginine salt of (2S) 3-[4-[2-(phenoxazin-10-yl)ethoxy]phenyl]-2-ethoxypropanoic acid (1.05 g).

Example 17

Process for the Preparation of Polymorphic Form I of L-arginine Salt of (2S) 3-[4-[2-(Phenoxazin-10-yl)ethoxy]phenyl]-2-ethoxypropanoic Acid A mixture of polymorphic Forms I and X of L-arginine salt of (2S) 3-[4-[2-(phenoxazin-10-yl)ethoxy]phenyl]-2-ethoxypropanoic acid (1.0 g) is suspended in isopropyl alcohol (10 ml) the reaction flask was covered with carbon, paper and stirred at room temperature for a period of 35–50 h. The reaction mixture was filtered, washed with little isopropyl alcohol and dried under vacuum at 40–45° C. for 4 h to yield polymorphic Form I of L-arginine salt of (2S) 3-[4-[2-(phenoxazin-10-yl)ethoxy]phenyl]-2-ethoxypropanoic acid (0.97 g).

ADVANTAGES OF THE INVENTION

The polymorphic forms of L-arginine salt of (2S) 3-[4-[2-(phenoxazin-10-yl)ethoxy]phenyl]-2-ethoxypropanoic acid, are more active/bio-available and are therefore very useful for the treatment or prophylaxis.

Ease in formulation containing these forms resulting in higher activity/bioavailability, in terms of lowering plasma blood sugar and plasma triglycerides.

We claim:

1. A polymorphic Form-I of L-arginine salt of (2S) 3-[4-[2-(phenoxazin-10-yl)ethoxy]phenyl]-2-ethoxypropanoic acid, having the formula I,

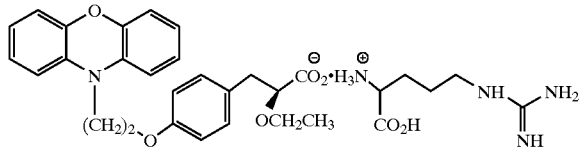

which is characterized by the data described hereunder:
DSC: Endotherm at 181.21° C. (onset at 177.70° C.)
X-ray powder diffraction (2θ): 8.18, 12.40, 16.66, 18.80, 19.44, 22.32, 22.84, 23.10, 23.50, 24.72, 29.84,
infrared absorption bands (cm$^{-1}$): 3249, 3062, 1709, 1587, 1489, 1374, 1272, 1243, 1112, 1043, 919, 737, 673, 543.

2. A polymorphic Form-II of L-arginine salt of (2S) 3-[4-[2-(phenoxazin-10-yl)ethoxy]phenyl]-2-ethoxypropanoic acid, having the formula I,

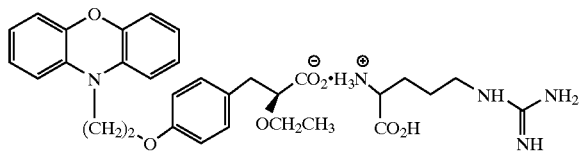

which is characterized by the data described hereunder:

DSC: Endotherms at 131° C., 166.24° C. and 178.96° C. Exotherm at 169.73° C.

X-ray powder diffraction (2θ): 6.78, 11.5, 12.08, 16.44, 19.34, 22.30, 22.72, 24.40, 26.66

Infrared absorption bands ($cm^{-1}$): 3055, 1711, 1589, 1510, 1491, 1376, 1274, 1111, 1039, 810, 730, 543.

3. A polymorphic Form-III of L-arginine salt of (2S) 3-[4-[2-(phenoxazin-10-yl)ethoxy]phenyl]-2-ethoxypropanoic acid, having the formula I,

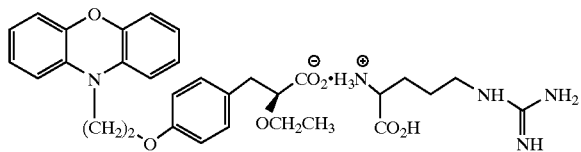

which is characterized by the data described hereunder:

DSC: Exotherm at 168.00° C.

Endotherm at 182.20° C. (onset at 171° C.),

Small endotherms at 99.66° C. and 164.38° C.

X-ray powder diffraction (2θ): 6.80, 12.10, 15.84, 17.02, 19.40, 22.32, 22.68, 24.38, 26.36, Infrared absorption bands ($cm^{-1}$): 3061, 1710, 1588, 1510, 1491, 1379, 1273, 1110, 1040, 805, 739 and 543.

4. A polymorphic Form-IV of L-arginine salt of (2S) 3-[4-[2-(phenoxazin-10-yl)ethoxy]phenyl]-2-ethoxypropanoic acid, having the formula I,

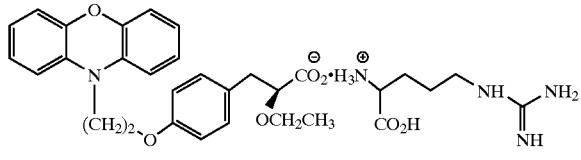

which is characterized by the data described hereunder:

DSC: Exotherm at 171.80° C.

Endotherms at 149.85° C. and 185.60° C. (onset at 147.78° C.),

Small endotherm at 164.51° C.

X-ray powderdiffraction (2θ): 6.78, 12.66, 15.96, 16.54, 19.34, 22.78, 24.42, 26.70, 31.70, Infrared absorption bands ($cm^{-1}$): 3056, 1711, 1589, 1493, 1381, 1274, 1242, 1101, 1060, 805, 743 and 543.7.

5. A polymorphic Form-V of L-arginine salt of (2S) 3-[4-[2-(phenoxazin-10-yl)ethoxy]phenyl]-2-ethoxypropanoic acid, having the formula I,

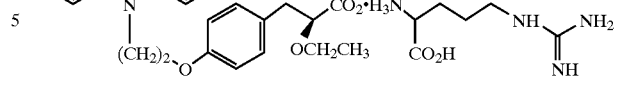

which is characterized by the data described hereunder:

DSC: Small exotherm at 173.82° C.

Endotherm at 185.95° C. (onset at 178.09° C.),

Small endotherms at 119.81° C., 164.69° C., and 172.44° C.

X-ray powder diffraction (2θ): 6.76, 12.10, 15.96, 17.00, 18.50, 19.40, 22.38, 22.44, 24.44, 26.30

Infrared absorption bands ($cm^{-1}$): 3266; 3055, 1711, 1589, 1510, 1492, 1379, 1274, 1175, 1111, 1040, 918, 819, 730, 676, 544.

6. A polymorphic Form-VI of L-arginine salt of (2S) 3-[4-[2-(phenoxazin-10-yl)ethoxy]phenyl]-2-ethoxypropanoic acid, having the formula I,

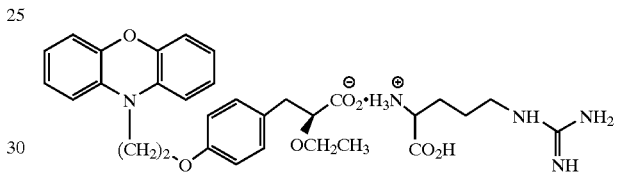

which is characterized by the data described hereunder:

DSC: Exotherm at 157.98° C.

Endotherms at 179.11° C. and 183.69° C. (onset at 157.98° C.),

Small endotherm at 77.80° C.

X-ray powder diffraction (2θ): No diffraction peaks due to its amorphous nature, Infrared absorption bands ($cm^{-1}$): 3065, 1629, 1490, 1377, 1273, 1244, 1109, 1042, 805, 740, 539.

7. A polymorphic Form-VII of L-arginine salt of (2S) 3-[4-[2-(phenoxazin-10-yl)ethoxy]phenyl]-2-ethoxypropanoic acid, having the formula I,

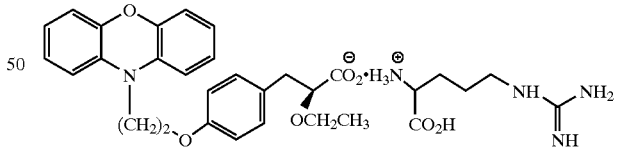

which is characterized by the data described hereunder:

DSC: Exotherm at 132.93° C.

Endotherms at 176.63° C. (onset at 169.06° C.) and 184.09° C.

X-ray powder diffraction (2θ): No diffraction due to its amorphous nature,

Infrared absorption bands ($cm^{-1}$): 3065, 1629, 1490, 1377, 1273, 1109, 1042, 740, 541.

8. A polymorphic Form-VIII of L-arginine salt of (2S) 3-[4-[2-(phenoxazin-10-yl)ethoxy]phenyl]-2-ethoxypropanoic acid, having the formula I,

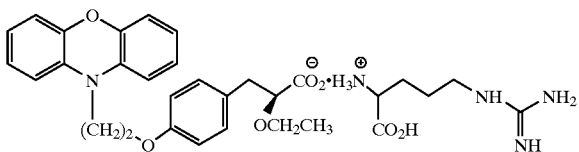

which is characterized by the data described hereunder:
  DSC: Exotherm at 158.27° C.
  Endotherm at 178.12° C. (onset at 167.15° C.),
  Small endotherm at 152.72° C.
  X-ray powder diffraction (2θ): 4.16, 11.02, 15.94, 19.50, 20.22, 22.22, 27.38,
  Infrared absorption bands (cm$^{-1}$): 3151, 1629, 1490, 1378, 1272, 1244, 1104, 1041, 742, 549.

9. A polymorphic Form-IX of L-arginine salt of (2S) 3-[4-[2-(phenoxazin-10-yl)ethoxy]phenyl]-2-ethoxypropanoic acid, having the formula I,

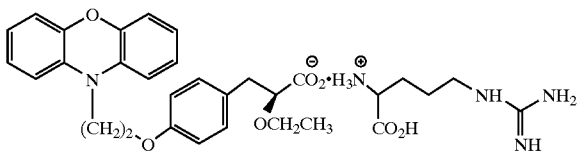

which is characterized by the data described hereunder:
  DSC: Endotherm at 176.67° C. (onset at 173.36° C.),
  X-ray powder diffraction (2θ): 8.20, 12.42, 16.66, 18.80, 19.44, 22.30, 23.08, 27.38, 28.48, 29.84,
  Infrared absorption bands (cm$^{-1}$): 3066, 1588, 1489, 1376, 1273, 1243, 1110, 1043, 919, 805, 737, 543.

10. A polymorphic Form-X of L-arginine salt of (2S) 3-[4-[2-(phenoxazin-10-yl)ethoxy]phenyl]-2-ethoxypropanoic acid, having the formula I,

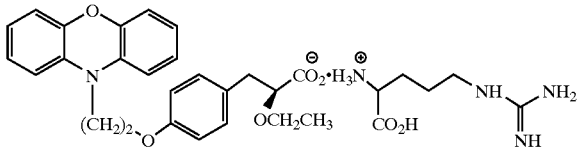

which is characterized by the data described hereunder:
  DSC: Endotherm at 184.53° C.
  Exotherm at 162.67° C.
  X-ray powder diffraction (2θ): No diffraction peaks due to its amorphous nature,
  Infrared absorption bands (cm$^{-1}$): 3413, 1630, 1511, 1491, 1377, 1273, 1244, 1176, 1108, 741.

11. A polymorphic Form-XI of L-arginine salt of (2S) 3-[4-[2-(phenoxazin-10-yl)ethoxy]phenyl]-2-ethoxypropanoic acid, having the formula I,

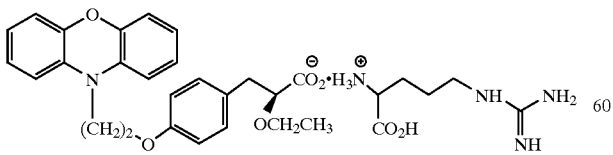

which is characterized by the data described hereunder:
  DSC: Endotherm at 184.40° C. (onset at 177.67° C.),
  X-ray powder diffraction (2θ): 7.38, 7.56, 11.90, 12.32, 14.80, 16.40, 19.58, 20.48, 22.34, 22.90, 23.54

Infrared absorption bands (cm$^{-1}$): 3383, 2925, 1629, 1510, 1490, 1377, 1273, 1243, 1090, 1041, 739, 539.

12. A process for the preparation of the polymorphic Form-I of L-arginine salt of (2S) 3-[4-[2-(phenoxazin-10-yl)ethoxy]phenyl]-2-ethoxy-propanoic acid, having the characteristics defined in claim 1 which comprises:
  (i) synthesizing (2S) 3-[4-[2-(phenoxazin-10-yl)ethoxy]phenyl]-2-ethoxypropanoic acid, employing known methods and dissolving in an organic solvent,
  (ii) adding L-arginine dissolved in water slowly with constant stirring to the solution obtained in step (i),
  (iii) stirring the reaction mixture at a temperature of 40–80° C. for a period in the range of 18–30 hours to obtain a white crystalline precipitate,
  (iv) filtering the white crystalline precipitate obtained in step (iii) above and
  (v) drying under vacuum at a temperature of 40–45° C. for a period in the range of 4–16 hours to yield Form-I of L-arginine salt of (2S) 3-[4-[2-(phenoxazin-10-yl)ethoxy]phenyl]-2-ethoxypropanoic acid.

13. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1 which comprises:
  (i) synthesizing 3-[4-[2-(phenoxazin-10-yl)ethoxy]phenyl]-2-ethoxypropanoic acid, employing known methods and dissolving in an organic solvent,
  (ii) adding L-arginine dissolved in water slowly with constant stirring to the solution obtained in step (i),
  (iii) stirring the reaction mixture at room temperature for a period in the range of 90–100 hours to obtain a white crystalline precipitate,
  (iv) filtering the white crystalline precipitate obtained in step (iii) above and
  (v) drying under vacuum at a temperature of 40–45° C. for a period in the range of 4–16 hours to yield Form-I of L-arginine salt of (2S) 3-[4-[2-(phenoxazin-10-yl)ethoxy]phenyl]-2-ethoxypropanoic acid.

14. A process for the preparation of the polymorphic Form-II of L-arginine salt of (2S) 3-[4-[2-(phenoxazin-10-yl)ethoxy]phenyl]-2-ethoxypropanoic acid, having the characteristics defined in claim 2 which comprises:
  (i) synthesizing (2S) 3-[4-[2-(phenoxazin-10-yl)ethoxy]phenyl]-2-ethoxypropanoic acid, employing known methods and dissolving in acetone,
  (ii) adding L-arginine dissolved in water slowly with constant stirring to the solution obtained in step (i),
  (iii) stirring the reaction mixture at room temperature for a period in the range of 18–30 hours to obtain a white crystalline precipitate,
  (iv) filtering the white crystalline precipitate obtained in step (iii) above and
  (v) drying under vacuum at a temperature of 40–45° C. for a period in the range of 4–16 hours to yield Form-II of L-arginine salt of (2S) 3-[4-[2-(phenoxazin-10-yl)ethoxy]phenyl]-2-ethoxypropanoic acid.

15. A process for the preparation of the polymorphic Form-III of L-arginine salt of (2S) 3-[4-[2-(phenoxazin-10-yl)ethoxy]phenyl]-2-ethoxypropanoic acid, having the characteristics defined in claim 3 which comprises:
  (i) synthesizing (2S) 3-[4-[2-(phenoxazin-10-yl)ethoxy]phenyl]-2-ethoxypropanoic acid, employing known methods and dissolving in 1,4-dioxane, (ii) adding L-arginine dissolved in water slowly with constant stirring to the solution obtained in step (i), (iii) stirring the reaction mixture at room temperature for a period in the range of 18–30 hours to obtain a white crystalline precipitate, (iv) filtering the white crystalline precipitate obtained in step (iii) above and (v) drying under vacuum at a temperature of 40–45° C. for a period in the range of 4–16 hours to yield Form-II of L-arginine salt of (2S) 3-[4-[2-(phenoxazin-10-yl)ethoxy]phenyl]-2-ethoxypropanoic acid.

16. A process for the preparation of the polymorphic Form-IV of L-arginine salt of (2S) 3-[4-[2-(phenoxazin-10-yl)ethoxy]phenyl]-2-ethoxypropanoic acid, having the characteristics defined in claim 4 which comprises:

(i) synthesizing (2S) 3-[4-[2-(phenoxazin-10-yl)ethoxy]phenyl]-2-ethoxypropanoic acid, employing known methods and dissolving in dimethyl sulfoxide, (ii) adding L-arginine dissolved in water slowly with constant stirring to the solution obtained in step (i), (iii) stirring the reaction mixture at room temperature for a period in the range of 18–30 hours to obtain a white crystalline precipitate, (iv) filtering the white crystalline precipitate obtained in step (iii) above and (v) drying under vacuum at a temperature of 40–45° C. for a period in the range of 4–16 hours to yield Form-IV of L-arginine salt of (2S) 3-[4-[2-(phenoxazin-10-yl)ethoxy]phenyl]-2-ethoxypropanoic acid.

17. A process for the preparation of the polymorphic Form-V of L-arginine salt of (2S) 3-[4-[2-(phenoxazin-10-yl)ethoxy]phenyl]-2-ethoxypropanoic acid, having the characteristics defined in claim 5 which comprises:

(i) synthesizing (2S) 3-[4-[2-(phenoxazin-10-yl)ethoxy]phenyl]-2-ethoxypropanoic acid, employing known methods and dissolving in dimethyl formamide, (ii) adding L-arginine dissolved in water slowly with constant stirring to the solution obtained in step (i), (iii) stirring the reaction mixture at room temperature for a period in the range of 18–30 hours to obtain a white crystalline precipitate, (iv) filtering the white crystalline precipitate obtained in step (iii) above and (v) drying under vacuum at a temperature of 40–45° C. for a period in the range of 4–16 hours to yield Form-V of L-arginine salt of (2S) 3-[4-[2-(phenoxazin-10-yl)ethoxy]phenyl]-2-ethoxypropanoic acid.

18. A process as claimed in claim 12 wherein the organic solvent is selected from the group consisting of acetonitrile, ethanol, methanol, 1,4-dioxane and isopropanol.

19. A process as claimed in claim 13 wherein the organic solvent is selected from the group consisting of acetonitrile, ethanol, methanol, 1,4-dioxane, and isopropanol.

20. A method for reducing plasma glucose, triglycerides, total cholesterol, LDL, VLDL or free fatty acids, or increasing HDL in the plasma comprising administering an effective amount of a polymorphic form I of L-arginine salt of (2S) 3-[4-[2-phenoxazin-10-yl)ethoxy]phenyl]-2-ethoxypropanoic acid as defined in claim 1 to a patient in need thereof.

21. A method for reducing plasma glucose, triglycerides, total cholesterol, LDL, VLDL or free fatty acids, or increasing HDL in the plasma comprising administering an effective amount of a polymorphic form II of L-arginine salt of (2S) 3-[4-[2-phenoxazin-10-yl)ethoxy]phenyl]-2-ethoxypropanoic acid as defined in claim 2 to a patient in need thereof.

22. A method for reducing plasma glucose, triglycerides, total cholesterol, LDL, VLDL or free fatty acids, or increasing HDL in the plasma comprising administering an effective amount of a polymorphic form III of L-arginine salt of (2S) 3-[4-[2-phenoxazin-10-yl)ethoxy]phenyl]-2-ethoxypropanoic acid as defined in claim 3 to a patient in need thereof.

23. A method for reducing plasma glucose, triglycerides, total cholesterol, LDL, VLDL or free fatty acids, or increasing HDL in the plasma comprising administering an effective amount of a polymorphic form IV of L-arginine salt of (2S) 3-[4-[2-phenoxazin-10-yl)ethoxy]phenyl]-2-ethoxypropanoic acid as defined in claim 4 to a patient in need thereof.

24. A method for reducing plasma glucose, triglycerides, total cholesterol, LDL, VLDL or free fatty acids, or increasing HDL in the plasma comprising administering an effective amount of a polymorphic form V of L-arginine salt of (2S) 3-[4-[2-phenoxazin-10-yl)ethoxy]phenyl]-2-ethoxypropanoic acid as defined in claim 5 to a patient in need thereof.

25. A method for reducing plasma glucose, triglycerides, total cholesterol, LDL, VLDL or free fatty acids, or increasing HDL in the plasma comprising administering an effective amount of a polymorphic form VI of L-arginine salt of (2S) 3-[4-[2-phenoxazin-10-yl)ethoxy]phenyl]-2-ethoxypropanoic acid as defined in claim 6 to a patient in need thereof.

26. A method for reducing plasma glucose, triglycerides, total cholesterol, LDL, VLDL or free fatty acids or increasing HDL in the plasma comprising administering an effective amount of a polymorphic form VII of L-arginine salt of (2S) 3-[4-[2-phenoxazin-10-yl)ethoxy]phenyl]-2-ethoxypropanoic acid as defined in claim 7 to a patient in need thereof.

27. A method for reducing plasma glucose, triglycerides, total cholesterol, LDL, VLDL or free fatty acids, or increasing HDL in the plasma comprising administering an effective amount of a polymorphic form VIII of L-arginine salt of (2S) 3-[4-[2-phenoxazin-10-yl)ethoxy]phenyl]-2-ethoxypropanoic acid as defined in claim 8 to a patient in need thereof.

28. A method for reducing plasma glucose, triglycerides, total cholesterol, LDL, VLDL or free fatty acids, or increasing HDL in the plasma comprising administering an effective amount of a polymorphic form IX of L-arginine salt of (2S) 3-[4-[2-phenoxazin-10-yl)ethoxy]phenyl]-2-ethoxypropanoic acid as defined in claim 9 to a patient in need thereof.

29. A method for reducing plasma glucose, triglycerides, total cholesterol, LDL, VLDL or free fatty acids, or increasing HDL in the plasma comprising administering an effective amount of a polymorphic form X of L-arginine salt of (2S) 3-[4-[2-phenoxazin-10-yl)ethoxy]phenyl]-2-ethoxypropanoic acid as defined in claim 10 to a patient in need thereof.

30. A method for reducing plasma glucose, triglycerides, total cholesterol, LDL, VLDL or free fatty acids, or increasing HDL in the plasma comprising administering an effective amount of a polymorphic form XI of L-arginine salt of (2S) 3-[4-[2-phenoxazin-10-yl)ethoxy]phenyl]-2-ethoxypropanoic acid as defined in claim 11 to a patient in need thereof.

31. A method for treating diabetes caused by insulin resistance or impaired glucose tolerance comprising administering an effective amount of a polymorphic form I of L-arginine salt of (2S) 3-[4-[2-phenoxazin-10-yl)ethoxy]

phenyl]-2-ethoxypropanoic acid as defined in claim 1 to a patient in need thereof.

32. A method for treating diabetes caused by insulin resistance or impaired glucose tolerance comprising administering an effective amount of a polymorphic form II of L-arginine salt of (2S) 3-[4-[2-phenoxazin-10-yl)ethoxy]phenyl]-2-ethoxypropanoic acid as defined in claim 2 to a patient in need thereof.

33. A method for treating diabetes caused by insulin resistance or impaired glucose tolerance comprising administering an effective amount of a polymorphic form III of L-arginine salt of (2S) 3-[4-[2-phenoxazin-10-yl)ethoxy]phenyl]-2-ethoxypropanoic acid as defined in claim 3 to a patient in need thereof.

34. A method for treating diabetes caused by insulin resistance or impaired glucose tolerance comprising administering comprising administering an effective amount of a polymorphic form IV of L-arginine salt of (2S) 3-[4-[2-phenoxazin-10-yl)ethoxy]phenyl]-2-ethoxypropanoic acid as defined in claim 4 to a patient in need thereof.

35. A method for treating diabetes caused by insulin resistance or impaired glucose tolerance comprising administering an effective amount of a polymorphic form V of L-arginine salt of (2S) 3-[4-[2-phenoxazin-10-yl)ethoxy]phenyl]-2-ethoxypropanoic acid as defined in claim 5 to a patient in need thereof.

36. A method for treating diabetes caused by insulin resistance or impaired glucose tolerance comprising administering an effective amount of a polymorphic form VI of L-arginine salt of (2S) 3-[4-[2-phenoxazin-10-yl)ethoxy]phenyl]-2-ethoxypropanoic acid as defined in claim 6 to a patient in need thereof.

37. A method for treating diabetes caused by insulin resistance or impaired glucose tolerance comprising administering an effective amount of a polymorphic form VII of L-arginine salt of (2S) 3-[4-[2-phenoxazin-10-yl)ethoxy]phenyl]-2-ethoxypropanoic acid as defined in claim 7 to a patient in need thereof.

38. A method for treating diabetes caused by insulin resistance or impaired glucose tolerance comprising administering an effective amount of a polymorphic form VIII of L-arginine salt of (2S) 3-[4-[2-phenoxazin-10-yl)ethoxy]phenyl]-2-ethoxypropanoic acid as defined in claim 8 to a patient in need thereof.

39. A method for treating diabetes caused by insulin resistance or impaired glucose tolerance comprising administering an effective amount of a polymorphic form IX of L-arginine salt of (2S) 3-[4-[2-phenoxazin-10-yl)ethoxy]phenyl]-2-ethoxypropanoic acid as defined in claim 9 to a patient in need thereof.

40. A method for treating diabetes caused by insulin resistance or impaired glucose tolerance comprising administering an effective amount of a polymorphic form X of L-arginine salt of (2S) 3-[4-[2-phenoxazin-10-yl)ethoxy]phenyl]-2-ethoxypropanoic acid as defined in claim 10 to a patient in need thereof.

41. A method for treating diabetes caused by insulin resistance or impaired glucose tolerance comprising administering an effective amount of a polymorphic form XI of L-arginine salt of (2S) 3-[4-[2-phenoxazin-10-yl)ethoxy]phenyl]-2-ethoxypropanoic acid as defined in claim 11 to a patient in need thereof.

42. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephroscleroris, retinopathy, or nephropathy, comprising administering an effective amount of a polymorphic form I of L-arginine salt of (2S) 3-[4-[2-phenoxazin-10-yl)ethoxy]phenyl]-2-ethoxypropanoic acid as defined in claim 1 to a patient in need thereof.

43. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephroscleroris, retinopathy, or nephropathy comprising administering an effective amount of a polymorphic form II of L-arginine salt of (2S) 3-[4-[2-phenoxazin-10-yl)ethoxy]phenyl]-2-ethoxypropanoic acid as defined in claim 2 to a patient in need thereof.

44. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephroscleroris, retinopathy, or nephropathy comprising administering an effective amount of a polymorphic form III of L-arginine salt of (2S) 3-[4-[2-phenoxazin-10-yl)ethoxy]phenyl]-2-ethoxypropanoic acid as defined in claim 3 to a patient in need thereof.

45. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephroscleroris, retinopathy, or nephropathy comprising administering an effective amount of a polymorphic form IV of L-arginine salt of (2S) 3-[4-[2-phenoxazin-10-yl)ethoxy]phenyl]-2-ethoxypropanoic acid as defined in claim 4 to a patient in need thereof.

46. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephroscleroris, retinopathy, or nephropathy comprising administering an effective amount of a polymorphic form V of L-arginine salt of (2S) 3-[4-[2-phenoxazin-10-yl)ethoxy]phenyl]-2-ethoxypropanoic acid as defined in claim 5 to a patient in need thereof.

47. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephrosclerois, retinopathy, or nephropathy comprising administering an effective amount of a polymorphic form VI of L-arginine salt of (2S) 3-[4-[2-phenoxazin-10-yl)ethoxy]phenyl]-2-ethoxypropanoic acid as defined in claim 6 to a patient in need thereof.

48. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephrosclerois, retinopathy, or nephropathy comprising administering an effective amount of a polymorphic form VII of L-arginine salt of (2S) 3-[4-[2-phenoxazin-10-yl)ethoxy]phenyl]-2-ethoxypropanoic acid as defined in claim 7 to a patient in need thereof.

49. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephrosclerois, retinopathy, or nephropathy comprising administering an effective amount of a polymorphic form VIII of L-arginine salt of (2S) 3-[4-[2-phenoxazin-10-yl)ethoxy]phenyl]-2-ethoxypropanoic acid as defined in claim 8 to a patient in need thereof.

50. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephrosclerois, retinopathy, or nephropathy comprising administering an effective amount of a polymorphic form IX of L-arginine salt of (2S) 3-[4-[2-phenoxazin-10-yl)ethoxy]phenyl]-2-ethoxypropanoic acid as defined in claim 9 to a patient in need thereof.

51. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephrosclerois, retinopathy, or nephropathy comprising administering an effective amount of a polymorphic form X of L-arginine salt of (2S) 3-[4-[2-phenoxazin-10-yl)ethoxy]phenyl]-2-ethoxypropanoic acid as defined in claim 10 to a patient in need thereof.

52. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephrosclerois, retinopathy, or nephropathy comprising administering an effective amount of a polymorphic form XI of L-arginine salt of (2S) 3-[4-[2-phenoxazin-10-yl)ethoxy]phenyl]-2-ethoxypropanoic acid as defined in claim 11 to a patient in need thereof.

53. A mixture of polymorphic Form I and X of L-arginine salt of (2S) 3-[-4-[2-(phenoxazin-10-yl)ethoxy]phenyl]-2-ethoxypropanoic acid, having the formula I,

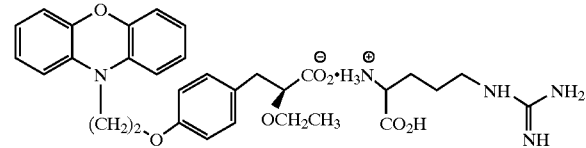

which is characterized by the data described hereunder:

DSC: Endotherms at 181.28° C., and 185.31° C., (onset at 173.54° C.)

X-ray powder diffraction (2θ); 8.16, 12.40, 16.64, 18.78, 22.34, 22.80, 23.08, 29.84, Infrared absorption bands (cm$^{-1}$); 3247, 3066, 1708, 1587, 1510, 1489, 1375, 1273, 1244, 1178, 1111, 1043, 805, 737, 673, 543.

54. A composition comprising a polymorphic Form selected from Forms I to XI of L-arginine salt of (2S) 3-[4-[2-(phenoxazin-10-yl)ethoxy]phenyl]-2-ethoxypropanoic acid as described in any one of claims 1–11 or 53 having the formula I

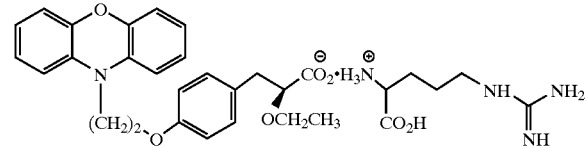

and a pharmaceutically acceptable carrier, diluent, excipient or solvate.

55. A process for the preparation of the polymorphic Form I and X of L-arginine salt of (2S) 3-[4-[2-(phenoxazin-10-yl)ethoxy]phenyl]-2-ethoxypropanoic acid, having the characteristics defined in claim 53, which comprises:

(i) synthesizing (2S) 3-[4-[2-(phenoxazin-10-yl)ethoxy]phenyl]-2-ethoxypropanoic acid, employing known methods and dissolving in an organic solvent, (ii) adding L-arginine dissolved in water slowly with constant stirring to the solution obtained in step (i), (iii) stirring the reaction mixture at room temperature for a period in the range of 18–30 hours to separate a white crystalline powder, (iv) filtering the white crystalline powder obtained in step (iii) above and (v) drying under vacuum at a temperature of 40–45° C. for a period in the range of 4–16 hours to yield Form I and X of L-arginine salt of (2S) 3-[4-[2-(phenoxazin-10-yl)ethoxy]phenyl]-2-ethoxypropanoic acid.

56. A process as claimed in 55 wherein the organic solvent is selected from the group consisting of acetonitrile, ethanol, methanol, 1,4-dioxane, and isopropanol.

57. The composition as claimed in claim 54 in the form of a tablet, capsule, powder, syrup, solution or suspension.

58. A method for reducing plasma glucose, triglycerides, total cholesterol, LDL, VLDL or free fatty acids, or increasing HDL in the plasma comprising administering an effective amount of a mixture of polymorphic form I and X of L-arginine salt of (2S) 3-[4-[2-phenoxazin-10-yl)ethoxy] phenyl]-2-ethoxypropanoic acid as defined in claim 53 to a patient in need thereof.

59. A method for treating diabetes caused by insulin resistance or impaired glucose tolerance comprising administering an effective amount of a mixture of polymorphic form I and X of L-arginine salt of (2S) 3-[4-[2-phenoxazin-10-yl)ethoxy]phenyl]-2-ethoxypropanoic acid defined in claim 53 to a patient in need thereof.

60. A method for treating a complication of type II diabetes said diabetes caused by insulin resistance or impaired glucose tolerance wherein the complication is dyslipidemia, hyperlipidemia, leptin resistance, hypercholesteremia, hyperglycemia, hypertension, coronary artery disease, cardiovascular disorders, arteriosclerosis, atherosclerosis, obesity, glomerulonephritis, glomerular sclerosis, nephrotic syndrome, hypertensive nephrosclerois, retinopathy, or nephropathy comprising administering an effective amount of a mixture of polymorphic form I and X of L-arginine salt of (2S) 3-[4-[2-phenoxazin-10-yl)ethoxy] phenyl]-2-ethoxypropanoic acid as defined in claim 53 to a patient in need thereof.

61. A process for the preparation of the polymorphic Form-VI of L-arginine salt of (2S) 3-[4-[2-(phenoxazin-10-yl)ethoxy]phenyl]-2-ethoxypropanoic acid, having the characteristics defined in claim 6 which comprises:
  (i) dissolving polymorphic Form I of L-arginine salt of (2S) 3-[4-[2-(phenoxazin-10-yl)ethoxy]phenyl]-2-ethoxypropanoic acid as defined in claim 1, in water and
  (ii) freeze drying the resulting solution to yield an amorphous white powder of Form-VI of L-arginine salt of (2S) 3-[4-[2-(phenoxazin-10-yl)ethoxy]phenyl]-2-ethoxypropanoic acid.

62. A process for the preparation of the polymorphic Form-VI of L-arginine salt of (2S) 3-[4-[2-(phenoxazin-10-yl)ethoxy]phenyl]-2-ethoxypropanoic acid, having the characteristics defined in claim 6 which comprises:
  (i) dissolving polymorphic Form II of L-arginine salt of (2S) 3-[4-[2-(phenoxazin-10-yl)ethoxy]phenyl]-2-ethoxypropanoic acid as defined in claim 2, in water and
  (ii) freeze drying the resulting solution to yield an amorphous white powder of Form-VI of L-arginine salt of (2S) 3-[4-[2-(phenoxazin-10-yl)ethoxy]phenyl]-2-ethoxypropanoic acid.

63. A process for the preparation of the polymorphic Form-VI of L-arginine salt of (2S) 3-[4-[2-(phenoxazin-10-yl)ethoxy]phenyl]-2-ethoxypropanoic acid, having the characteristics defined in claim 6, which comprises:
  (i) dissolving polymorphic form III of L-arginine salt of (2S) 3-[4-[2-(phenoxazin-10-yl)ethoxy]phenyl]-2-ethoxypropanoic acid as defined in claim 3, in water and
  (ii) freeze drying the resulting solution to yield an amorphous white powder of Form-VI of L-arginine salt of (2S) 3-[4-[2-(phenoxazin-10-yl)ethoxy]phenyl]-2-ethoxypropanoic acid.

64. A process for the preparation of the polymorphic Form-VI of L-arginine salt of (2S) 3-[4-[2-(phenoxazin-10-yl)ethoxy]phenyl]-2-ethoxypropanoic acid, having the characteristics defined in claim 7 which comprises:
  (i) dissolving a polymorphic Form IV of L-arginine salt of (2S) 3-[4-[2-(phenoxazin-10-yl)ethoxy]phenyl]-2-ethoxypropanoic acid as defined in claim 4, in water and
  (ii) freeze drying the resulting to yield an amorphous white powder of Form-VI of L-arginine salt of (2S) 3-[4-[2-(phenoxazin-10-yl)ethoxy]phenyl]-2-ethoxypropanoic acid.

65. A process for the preparation of the polymorphic Form-VI of L-arginine salt of (2S) 3-[4-[2-(phenoxazin-10-yl)ethoxy]phenyl]-2-ethoxypropanoic acid, having the characteristics defined in claim 6 which comprises:
  (i) dissolving polymorphic Form V of L-arginine salt of (2S) 3-[4-[2-(phenoxazin-10-yl)ethoxy]phenyl]-2-ethoxypropanoic acid as defined in claim 5, in water and
  (ii) freeze drying the resulting solution to yield an amorphous white powder of Form-VI of L-arginine salt of (2S) 3-[4-[2-(phenoxazin-10-yl)ethoxy]phenyl]-2-ethoxypropanoic acid.

66. A process for the preparation of the polymorphic Form-VII of L-arginine salt of (2S) 3-[4-[2-(phenoxazin-10-yl)ethoxy]phenyl]-2-ethoxypropanoic acid, having the characteristics defined in claim 7 which comprises:
  (i) dissolving a polymorphic Form I of L-arginine salt of (2S) 3-[4-[2-(phenoxazin-10-yl)ethoxy]phenyl]-2-ethoxypropanoic acid as defined in claim 1, in methanol and
  (ii) evaporating the resulting solution under vacuum to obtain an amorphous white powder of Form-VII of L-arginine salt of (2S) 3-[4-[2-(phenoxazin-10-yl)ethoxy]phenyl]-2-ethoxypropanoic acid.

67. A process for the preparation of the polymorphic Form-VII of L-arginine salt of (2S) 3-[4-[2-(phenoxazin-10-yl)ethoxy]phenyl]-2-ethoxypropanoic acid, having the characteristics defined in claim 7 which comprises:
  (i) dissolving a polymorphic Form II of L-arginine salt of (2S) 3-[4-[2-(phenoxazin-10-yl)ethoxy]phenyl]-2-ethoxypropanoic acid as defined in claim 2, in methanol and
  (ii) evaporating the resulting solution under vacuum to obtain an amorphous white powder of Form-VII of L-arginine salt of (2S) 3-[4-[2-(phenoxazin-10-yl)ethoxy]phenyl]-2-ethoxypropanoic acid.

68. A process for the preparation of the polymorphic Form-VII of L-arginine salt of (2S) 3-[4-[2-(phenoxazin-10-yl)ethoxy]phenyl]-2-ethoxypropanoic acid, having the characteristics defined in claim 7 which comprises:
  (i) dissolving a polymorphic Form III of L-arginine salt of (2S) 3-[4-[2-(phenoxazin-10-yl)ethoxy]phenyl]-2-ethoxypropanoic acid as defined in claim 3, in methanol and
  (ii) evaporating the resulting solution under vacuum to obtain an amorphous white powder of Form-VII of L-arginine salt of (2S) 3-[4-[2-(phenoxazin-10-yl)ethoxy]phenyl]-2-ethoxypropanoic acid.

69. A process for the preparation of the polymorphic Form-VII of L-arginine salt of (2S) 3-[4-[2-(phenoxazin-10-yl)ethoxy]phenyl]-2-ethoxypropanoic acid, having the characteristics defined in claim 7 which comprises:
  (i) dissolving a polymorphic Form IV of L-arginine salt of (2S) 3-[4-[2-(phenoxazin-10-yl)ethoxy]phenyl]-2-ethoxypropanoic acid as defined in claim 4, in methanol and
  (ii) evaporating the resulting solution under vacuum to obtain an amorphous white powder of Form-VII of L-arginine salt of (2S) 3-[4-[2-(phenoxazin-10-yl) ethoxy]phenyl]-2-ethoxypropanoic acid.

70. A process for the preparation of the polymorphic Form-VII of L-arginine salt of (2S) 3-[4-[2-(phenoxazin-10- yl)ethoxy]phenyl]-2-ethoxypropanoic acid, having the characteristics defined in claim 7 which comprises:
  (i) dissolving a polymorphic Form V of L-arginine salt of (2S) 3-[4-[2-(phenoxazin-10-yl)ethoxy]phenyl]-2-ethoxypropanoic acid as defined in claim 5, in methanol and
  (ii) evaporating the resulting solution under vacuum to obtain an amorphous white powder of Form-VII of L-arginine salt of (2S) 3-[4-[2-(phenoxazin-10-yl)ethoxy]phenyl]-2-ethoxypropanoic acid.

71. A process for the preparation of the polymorphic Form-VIII of L-arginine salt of (2S) 3-[4-[2-(phenoxazin-10-yl)ethoxy]phenyl]-2-ethoxypropanoic acid, having the characteristics defined in claim 8 which comprises:
  (i) synthesizing (2S) 3-[4-[2-(phenoxazin-10-yl)ethoxy] phenyl]-2-ethoxypropanoic acid, employing known methods and dissolving in an organic solvent,
  (ii) adding L-arginine dissolved in water slowly with constant stirring to the solution obtained in step (i),
  (iii) stirring the reaction mixture at a temperature of 40–80° C. for a period in the range of 18–30 hours to obtain a white crystalline precipitate,
  (iv) filtering the white crystalline precipitate obtained in step (iii) above and
  (v) drying under vacuum at a temperature of 40–45° C. for a period in the range of 4–16 hours to yield Form-I of L-arginine salt of (2S) 3-[4-[2-(phenoxazin-10-yl) ethoxy]phenyl]-2-ethoxypropanoic acid as defined in claim 1,
  (vi) refluxing the Form-I of L-arginine salt of (2S) 3-[4-[2-(phenoxazin-10-yl)ethoxy]phenyl]-2-ethoxypropanoic acid, obtained above in step (v) in 1,4-dioxane for a period in the range of 8–16 hours and
  (vii) filtering and drying under vacuum at a temperature of 40–45° C. for a period in the range of 4–16 hours to yield Form-VIII of L-arginine salt of (2S) 3-[4-[2-(phenoxazin-10-yl)ethoxy]phenyl]-2-ethoxypropanoic acid.

72. A process for the preparation of the polymorphic Form-IX of L-arginine salt of (2S) 3-[4-[2-(phenoxazin-10-yl)ethoxy]phenyl]-2-ethoxypropanoic acid, having the characteristics defined in claim 9 which comprises:
  (i) synthesizing (2S) 3-[4-[2-(phenoxazin-10-yl)ethoxy] phenyl]-2-ethoxypropanoic acid, employing known methods and dissolving in an organic solvent,
  (ii) adding L-arginine dissolved in water slowly with constant stirring to the solution obtained in step (i),
  (iii) stirring the reaction mixture at a temperature of 40–80° C. for a period in the range of 18–30 hours to obtain a white crystalline precipitate,
  (iv) filtering the white crystalline precipitate obtained in step (iii) above,
  (v) drying under vacuum at a temperature of 40–45° C. for a period in the range of 4–16 hours to yield Form-I of L-arginine salt of (2S) 3-[4-[2-(phenoxazin-10-yl) ethoxy]phenyl]-2-ethoxypropanoic acid as defined in claim 1,
  (vi) refluxing the Form-I of L-arginine salt of (2S) 3-[4-[2-(phenoxazin-10-yl)ethoxy]phenyl]-2-ethoxypropanoic acid, obtained above in step (v) in 1,4-dioxane for a period in the range of 8–16 hours,
  (vii) filtering and drying under vacuum at a temperature of 40–45° C. for a period in the range of 4–16 hours to yield Form-VIII of L-arginine salt of (2S) 3-[4-[2-(phenoxazin-10-yl)ethoxy]phenyl]-2-ethoxypropanoic acid as defined in claim 8,
  (viii) refluxing the Form-VIII of L-arginine salt of (2S) 3-[4-[2-(phenoxazin-10-yl)ethoxy]phenyl]-2-ethoxypropanoic acid, obtained in step (vii) above in isopropyl alcohol for a period in the range of 8–16 hours and
  (ix) filtering and drying under vacuum at a temperature of 40–45° C. for a period in the range of 4–16 hours to yield Form-IX of L-arginine salt of (2S) 3-[4-[2-(phenoxazin-1 0-yl)ethoxy]phenyl]-2-ethoxypropanoic acid.

73. A process for the preparation of the polymorphic Form-X of L-arginine salt of (2S) 3-[4-[2-(phenoxazin-10-yl)ethoxy]phenyl]-2-ethoxypropanoic acid, having the characteristics defined in claim 10, which comprises:
  (i) synthesizing (2S) 3-[4-[2-(phenoxazin-10-yl)ethoxy] phenyl]-2-ethoxypropanoic acid, employing known methods and dissolving in an organic solvent,
  (ii) adding L-arginine dissolved in water slowly with constant stirring to the solution obtained in step (i),
  (iii) stirring the reaction mixture at a temperature of 40–80° C. for a period in the range of 18–30 hours to obtain a white crystalline precipitate,
  (iv) filtering the white crystalline precipitate obtained in step (iii) above,
  (v) drying under vacuum at a temperature of 40–45° C. for a period in the range of 4–16 hours to yield Form-I of L-arginine salt of (2S) 3-[4-[2-(phenoxazin-10-yl) ethoxy]phenyl]-2-ethoxypropanoic acid as defined in claim 1 and
  (vi) heating the polymorphic Form-I obtained in step (v) at 185° C. and cooling it to room temperature to yield Form-X of L-arginine salt of (2S) 3-[4-[2-(phenoxazin-10-yl)ethoxy]phenyl]-2-ethoxypropanoic acid.

74. A process for the preparation of the polymorphic Form-XI of L-arginine salt of (2S) 3-[4-[2-(phenoxazin-10-yl)ethoxy]phenyl]-2-ethoxypropanoic acid, having the characteristics defined in claim 11, which comprises:
  (i) synthesizing (2S) 3-[4-[2-(phenoxazin-10-yl)ethoxy] phenyl]-2-ethoxypropanoic acid, employing known methods and dissolving in an organic solvent,
  (ii) adding L-arginine dissolved in water slowly with constant stirring to the solution obtained in step (i),
  (iii) stirring the reaction mixture at a temperature of 40–80° C. for a period in the range of 18–30 hours to obtain a white crystalline precipitate,
  (iv) filtering the white crystalline precipitate obtained in step (iii) above,
  (v) drying under vacuum at a temperature of 40–45° C. for a period in the range of 4–16 hours to yield Form-I of L-arginine salt of (2S) 3-[4-[2-(phenoxazin-10-yl) ethoxy]phenyl]-2-ethoxypropanoic acid as defined in claim 1,
  (vi) heating the polymorphic Form-I obtained in step (v) to 185° C. and cooling it to room temperature to yield Form-X of L-arginine salt of (2S) 3-[4-[2-(phenoxazin-10-yl)ethoxy]phenyl]-2-ethoxypropanoic acid as defined in claim 10,
  (vii) heating the polymorphic Form-X obtained in step (vi) to 175° C. and cooling it to room temperature to yield Form-XI of L-arginine salt of (2S) 3-[4-[2-(phenoxazin-10-yl)ethoxy]phenyl]-2-ethoxypropanoic acid.

75. A process for the preparation of the polymorphic Form-I of L-arginine salt of 2S) 3-[4-[2-(phenoxazin-10-yl)ethoxy]phenyl]-2-ethoxypropanoic acid, having the characteristics defined in claim 1, which comprises:

(i) suspending a polymorphic Form II of L-arginine salt of (2S) 3-[4-[2-(phenoxazin-10-yl)ethoxy]phenyl]-2-ethoxypropanoic acid as defined in claim 2 in isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2) 3-[4-[2-(phenoxazin-10-yl)ethoxy]phenyl]-2-ethoxypropanoic acid.

76. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1, which comprises:

(i) suspending a polymorphic Form III of L-arginine salt of (2S) 3-[4-[2-(phenoxazin-10-yl)ethoxy]phenyl]-2-ethoxypropanoic acid as defined in claim 3 in isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2S) 3-[4-[2-(phenoxazin-10-yl)ethoxy]phenyl]-2-ethoxypropanoic acid.

77. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1, which comprises:

(i) suspending a polymorphic Form IV of L-arginine salt of (2S) 3-[4-[2-(phenoxazin-10-yl)ethoxy]phenyl]-2-ethoxypropanoic acid as defined in claim 4 in isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2S) 3-[4-[2-(phenoxazin-10-yl)ethoxy]phenyl]-2-ethoxypropanoic acid.

78. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1, which comprises:

(i) suspending a polymorphic Form V of L-arginine salt of (2S) 3-[4-[2-(phenoxazin-10-yl)ethoxy]phenyl]-2-ethoxypropanoic acid as defined in claim 5 in isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2S) 3-[4-[2-(phenoxazin-10-yl)ethoxy]phenyl]-2-ethoxypropanoic acid.

79. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1, which comprises:

(i) suspending a polymorphic Form VI of L-arginine salt of (2S) 3-[4-[2-(phenoxazin-10-yl)ethoxy]phenyl]-2-ethoxypropanoic acid as defined in claim 6 isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2S) 3-[4-[2-(phenoxazin-10-yl)ethoxy]phenyl]-2-ethoxypropanoic acid.

80. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1, which comprises:

(i) suspending a polymorphic Form VII of L-arginine salt of (2S) 3-[4-[2-(phenoxazin-10-yl)ethoxy]phenyl]-2-ethoxypropanoic acid as defined in claim 7 in isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2S) 3-[4-[2-(phenoxazin-10-yl)ethoxy]phenyl]-2-ethoxypropanoic acid.

81. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1, which comprises:

(i) suspending a polymorphic Form VIII of L-arginine salt of (2S) 3-[4-[2-(phenoxazin-10-yl)ethoxy]phenyl]-2-ethoxypropanoic acid as defined in claim 8 in isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2S) 3-[4-[2-(phenoxazin-10-yl)ethoxy]phenyl]-2-ethoxypropanoic acid.

82. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1, which comprises:

(i) suspending a polymorphic Form IX of L-arginine salt of (2S) 3-[4-[2-(phenoxazin-10-yl)ethoxy]phenyl]-2-ethoxypropanoic acid as defined in claim 9 in isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2S) 3-[4-[2-(phenoxazin-10-yl)ethoxy]phenyl]-2-ethoxypropanoic acid.

83. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1, which comprises:

(i) suspending a polymorphic Form X of L-arginine salt of (2S) 3-[4-[2-(phenoxazin-10-yl)ethoxy]phenyl]-2-ethoxypropanoic acid as defined in claim 10 in isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2S) 3-[4-[2-(phenoxazin-10-yl)ethoxy]phenyl]-2-ethoxypropanoic acid.

84. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1, which comprises:

(i) suspending a polymorphic Form XI of L-arginine salt of (2S) 3-[4-[2-(phenoxazin-10-yl)ethoxy]phenyl]-2-ethoxypropanoic acid as defined in claim 11 isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2S) 3-[4-[2-(phenoxazin-10-yl)ethoxy]phenyl]-2-ethoxypropanoic acid.

85. A process for the preparation of the polymorphic Form-I of L-arginine salt of (2S) 3-[4-[2-(phenoxazin-10-yl)ethoxy]phenyl]-2-ethoxypropanoic acid, having the characteristics defined in claim 1, which comprises:

(i) suspending a polymorphic Form I and X of L-arginine salt of (2S) 3-[4-[2-(phenoxazin-10-yl)ethoxy]phenyl]-2-ethoxypropanoic acid as defined in claim 53 in isopropyl alcohol and stirring in dark conditions at room temperature for a period of 35–50 hours, (ii) filtering and washing with isopropyl alcohol and, (iii) drying under vacuum at a temperature of 40–45° C. for a period in the range of 4–16 hours to yield polymorphic Form I of L-arginine salt of (2S) 3-[4-[2-(phenoxazin-10-yl)ethoxy]phenyl]-2-ethoxypropanoic acid.

86. A process as claimed in claim 71 wherein the organic solvent is selected from the group consisting of acetonitrile, ethanol, methanol, 1,4-dioxane, and isopropanol.

87. A process as claimed in claim 72 wherein the organic solvent is selected from the group consisting of acetonitrile, ethanol, methanol, 1,4-dioxane, and isopropanol.

88. A process as claimed in claim 73 wherein the organic solvent is selected from the group consisting of acetonitrile, ethanol, methanol, 1,4-dioxane, and isopropanol.

89. A process as claimed in claim 74 wherein the organic solvent is selected from the group consisting of acetonitrile, ethanol, methanol, 1,4-dioxane, and isopropanol.

90. A method for the treatment of disorders related to Syndrome X, which comprises administering a polymorphic Form I of L-arginine salt of (2S) 3-[4-[2-(phenoxazin-10-yl)ethoxy]phenyl]-2-ethoxypropanoic acid, as defined in claim 1 to a patient in need thereof.

91. A method for the treatment of disorders related to Syndrome X, which comprises administering a polymorphic Form II of L-arginine salt of 2S) 3-[4-[2-(phenoxazin-10-yl)ethoxy]phenyl]-2-ethoxypropanoic acid, as defined in claim 2 to a patient in need thereof.

92. A method for the treatment of disorders related to Syndrome X, which comprises administering a polymorphic Form III of L-arginine salt of 2S) 3-[4-[2-(phenoxazin-10-yl)ethoxy]phenyl]-2-ethoxypropanoic acid, as defined in claim 3 to a patient in need thereof.

93. A method for the treatment of disorders related to Syndrome X, which comprises administering a polymorphic Form IV of L-arginine salt of 2S) 3-[4-[2-(phenoxazin-10-yl)ethoxy]phenyl]-2-ethoxypropanoic acid, as defined in claim 4 to a patient in need thereof.

94. A method for the treatment of disorders related to Syndrome X, which comprises administering a polymorphic Form III of L-arginine salt of 2S) 3-[4-[2-(phenoxazin-10-yl)ethoxy]phenyl]-2-ethoxypropanoic acid, as defined in claim 4 to a patient in need thereof.

95. A method for the treatment of disorders related to Syndrome X, which comprises administering a polymorphic Form VI of L-arginine salt of 2S) 3-[4-[2-(phenoxazin-10-yl)ethoxy]phenyl]-2-ethoxypropanoic acid, as defined in claim 5 to a patient in need thereof.

96. A method for the treatment of disorders related to Syndrome X, which comprises administering a polymorphic Form VII of L-arginine salt of 2S) 3-[4-[2-(phenoxazin-10-yl)ethoxy]phenyl]-2-ethoxypropanoic acid, as defined in claim 6 to a patient in need thereof.

97. A method for the treatment of disorders related to Syndrome X, which comprises administering a polymorphic Form VIII of L-arginine salt of 2S) 3-[4-[2-(phenoxazin-10-yl)ethoxy]phenyl]-2-ethoxypropanoic acid, as defined in claim 7 to a patient in need thereof.

98. A method for the treatment of disorders related to Syndrome X, which comprises administering a polymorphic Form IX of L-arginine salt of 2S) 3-[4-[2-(phenoxazin-10-yl)ethoxy]phenyl]-2-ethoxypropanoic acid, as defined in claim 8 to a patient in need thereof.

99. A method for the treatment of disorders related to Syndrome X, which comprises administering a polymorphic Form X L-arginine salt of 2S) 3-[4-[2-(phenoxazin-10-yl)ethoxy]phenyl]-2-ethoxypropanoic acid, as defined in claim 9 to a patient in need thereof.

100. A method for the treatment of disorders related to Syndrome X, which comprises administering a polymorphic Form XI of L-arginine salt of 2S) 3-[4-[2-(phenoxazin-10-yl)ethoxy]phenyl]-2-ethoxypropanoic acid, as defined in claim 10 to a patient in need thereof.

101. A method for the treatment of disorders related to Syndrome X, which comprises administering a polymorphic Form I and X of L-arginine salt of 2S) 3-[4-[2-(phenoxazin-10-yl)ethoxy]phenyl]-2-ethoxypropanoic acid, as defined in claim 53 to a patient in need thereof.

* * * * *

UNITED STATES PATENT AND TRADEMARK OFFICE
CERTIFICATE OF CORRECTION

PATENT NO. : 6,528,507 B1
DATED : March 4, 2003
INVENTOR(S) : Om Reddy Gaddam et al.

It is certified that error appears in the above-identified patent and that said Letters Patent is hereby corrected as shown below:

<u>Title page,</u>
Item [75], "Ra jender" should read -- Rajender -- and
"Ra ju" should read -- Raju --;
After "(IN)" insert -- ; Soren Ebdrup, Copenhagen, DK; Petra Christine Lugstein, Wien, Austria --
Insert -- [30] Foreign Application Priority Data April 16, 1999 (WO) .... IB99/00681 --.

Signed and Sealed this

Twenty-fourth Day of June, 2003

JAMES E. ROGAN
*Director of the United States Patent and Trademark Office*